US005693508A

United States Patent [19]

Chang

[11] Patent Number: 5,693,508
[45] Date of Patent: Dec. 2, 1997

[54] RETROVIRAL EXPRESSION VECTORS CONTAINING MOMLV/CMV-IE/HIV-TAR CHIMERIC LONG TERMINAL REPEATS

[76] Inventor: Lung-Ji Chang, 11456, 71 Avenue,, Edmonton, Alberta, Canada, T6G 0A7

[21] Appl. No.: 336,132

[22] Filed: Nov. 8, 1994

[51] Int. Cl.$^6$ .......................... C12N 15/00; C12N 15/09; C12N 15/63; C12P 21/06
[52] U.S. Cl. .................. 435/172.3; 435/69.1; 435/320.1; 536/24.1
[58] Field of Search .............................. 435/69.1, 91.4, 435/172.3, 236, 320.1; 536/23.72, 24.1

[56] References Cited

U.S. PATENT DOCUMENTS

| 4,683,195 | 7/1987 | Mullis et al. | 435/6 |
| 4,683,202 | 7/1987 | Mullis | 435/91 |

OTHER PUBLICATIONS

Brenner, M., 1994 Immunomethods 5:204–210.
Leiden, J., 1995 New Engl. J. Med. 333:871–873.
Mulligan, R., 1993 Science 260:926–932.
Watson, J.D., et al. (1992) *Recombinant DNA*, Second Edition, W.H. Freeman and Co., NY, pp. 256–263.
Yu, M., Poeschla, E. and Wong–Staal, F., "Progress Towards Gene Therapy for HIV Infection," Gene Ther. 1:13–26 (1994).
Tenth International Conference on AIDS, The Global Challenge of AIDS: Together for the Future, Yokohama, Japan, Aug. 7–11, 1994.
Cech, T.R. and Bass, B., "Biological Catalysis by RNA," Ann. Rev. Biochem. 55:599–629 (1986).
Sarver, N. et al., "Ribozymes as Potential Anti–HIV–1 Therapeutic Agents," Science 247:1222–1225 (1990).
Appendices, Human Gene Therapy 5(1):147 (1994).
Bahner, I. et al., "Comparison of trans–Dominant Inhibitory Mutant Human Immunodeficiency Virus Type I Genes Expressed by Retroviral Vectors in Human T Lymphocytes," J. Virol., 67:3199 (1993).
Appendices, "Clinical Protocol: A Molecular Genetic Intervention for AIDS–Effects of a Transdominant Negative Form of Rev", Human Gene Therapy 5:79–92 (1994).
Riddell, S.R., Human Gene Therapy 5(1):141 (1994).
Culver, K.W. et al., "Lymphocyte Gene Therapy," Human Gene Therapy 2:107–109 (1991).
Grossman, M. et al., "Successful Ex–Vivo Gene Therapy Directed to Liver in a Patient with Familial Hypercholesterolaemia", Nat. Genet. 6:335–341 (1994).
Kasid, A. et al., "Human Gene Transfer: Characterization of Human Tumor–Infiltrating Lymphocytes as Vehicles for Retroviral–Mediated Gene Transfer in Man", Proc. Natl. Acad. Sci. 87:473–477 (1990).
Rosenberg, S. A. Human Gene Therapy 5(1):140 (1994).
Gewirtz, A.M., "Oligodeoxynucleotide–Based Therapeutics for Human Leukemias", Stem Cells 11(3):96–103 (1993).
Neckers, L. and Whitesell, L., "Antisense Technology: Biological Utility and Practical Considerations", Am J. of Physiol. 265:L1–L12 (1993).

Nienhuis, A.W. et al., "Viruses as Therapeutic Gene Transfer Vectors," Hematobyt, vol. 16: *Viruses and Bone Marrow,* Young, N.S. ed, Chapter 12, pp. 353–414 (1993).
Markowitz, D. et al. "A Safe Packaging Line for Gene Transfer: Separating Viral Genes on Two Different Plasmids," J. Virol. 62(4):1120–1124 (1988).
Miller, A.D. and Buttimore, C., "Redesign of Retrovirus Packaging Cell Lines To Avoid Recombination Leading to Helper Virus Production," Mol. Cell. Biol. 6(8):2895–2902 (1986).
Miller, D.G., et al., "Gene Transfer by Retrovirus Vectors Occurs Only in Cells That Are Actively Replicating at the Time of Infection", Mol. Cell. Biol. 10(8):4239–4242 (1990).
Miller, A.D. and Rosman, G.J., "Improved Retroviral Vectors for Gene Transfer and Expression," BioTechniques, 7(9):980–990 (1989).
Miller, A.D., "Human Gene Therapy Comes of Age," Nature 357:455–460 (1992).
B.R. Glick and J.J. Pasternak, *Molecular Biotechnology*, American Society for Microbiology, 1994, p. 412.
Robinson, D., Elliott, J.F. and Chang, L.–J., "Retroviral Vector with a CMV–IE/HIV–TAR Hybrid LTR Gives High Basal Expression Levels and is Upregulated by HIV–1 Tat," Gene Therapy, in press.
Mann, et al., "Construction of a Retrovirus Packaging Mutant and Its Use to Produce Helper–Free Defective Retrovirus," Cell 33:153–159.
Bender, M.A., et al., "Evidence that the Packaging Signal of Moloney Murine Leukemia Virus Extends into the *gag* Region," J. Virol. 61(5):1639–1646 (1987).
Supplements and Appendices in *RNA Tumor Viruses, Molecular Biology of Tumor Viruses*, 2nd Ed. (1985) pp. 986–988.

(List continued on next page.)

*Primary Examiner*—Christine M. Nucker
*Assistant Examiner*—Jeffrey S. Parkin
*Attorney, Agent, or Firm*—Medlen & Carroll

[57] ABSTRACT

Novel retroviral vectors were constructed by making modifications to the Moloney murine leukemia virus (MoMLV) long terminal repeat (LTR). A portion of the U3 region of the MoMLV LTR was replaced with a hybrid regulatory element consisting of the human cytomegalovirus immediate-early enhancer/promoter (CMV-IE) together with the human immunodeficiency virus transactivation response element (HIV-TAR). Transfection of chloramphenicol acetyl transferase (CAT) reporter constructs into a variety of human cell lines showed that the CMV-IE/HIV-TAR enhancer/promoter chimeric MoMLV LTR exhibited basal expression levels which were 10- to 50-fold higher than those obtained from the wild-type MoMLV LTR enhancer/promoter. Expression from the recombinant LTR was further increased in the presence of the HIV-1 Tat protein. When stably transfected into an amphotropic packaging cell line, the modified retroviral vector containing the chimeric LTR plus an extended packaging signal consistantly gave higher titers of retrovirus than did the parental MoMLV based vector. These novel retroviral vectors provide improved means for the delivery and expression of genes in different cell types.

28 Claims, 24 Drawing Sheets

OTHER PUBLICATIONS

Sambrook, J. et al., *Molecular Cloning: A Laboratory Manual*, 2nd Ed., Cold Spring Harbor Laboratory Press, New York (1989) pp. 1.21–1.52, pp. 1.34–1.35, pp. 7.39–7.53, and pp. 16.6–16.15.

Anderson and Young, Quantitative Filter Hybridisation, in *Nucleic Acid Hybridization*, pp. 73–111 (1985).

D.L. Kacian et al., "A Replicating RNA Molecule Suitable for a Detailed Analysis of Extracellular Evolution and Replication," Proc. Natl. Acad. Sci. USA 69(10):3038–3042 (1972).

M. Chamberlin et al., "New RNA Polymerase from *Escherichia coli* infected with Bacteriophage T7," Nature 228:227–231 (1970).

D.Y. Wu and R.B. Wallace, "The Ligation Amplification Reaction (LAR)—Amplification of Specific DNA Sequences Using Sequential Rounds of Template–Dependent Ligation", Genomics 4:560–569 (1989).

*PCR Technology*, H.A. Erlich (ed.), pp. 7–16 (Stockton Press 1989).

K.B. Mullis, et al., "Specific Enzymatic Amplification of DNA In Vitro: The Polymerase Chain Reaction," Cold Spring Harbor Symposia, vol. II, pp. 263–273 (1986).

Maniatis, T. et al., "Regulation of Inducible and Tissue–Specific Gene Expression," Science 236:1237–1245 (1987).

Voss, S.D. et al., "The Role of Enhancers in the Regulation of Cell–Type–Specific Transcriptional Control", Trends Biochem. Sci., 11:287–289 (1986).

Dijkema, R. et al., "Cloning and Expression of the Chromosomal Immune Interferon Gene of the Rat," EMBO J. 4(3):761–767 (1985).

Uetsuki, T. et al., "Isolation and Characterization of the Human Chromosomal Gene for Polypeptide Chain Elongation Factor–1α," J. Biol. Chem., 264(10):5791–5798 (1989).

Kim, D.W. et al., "Use of the Human Elongation Factor 1α Promoter as a Versatile and Efficient Expression System," Gene 91:217–223 (1990).

Mizushima, S. and Nagata, S., "pEF–BOS, a Powerful Mammalian Expression Vector," Nuc. Acids. Res., 18(17):5322 (1990).

Gorman, C.M. et al., "The Rous Sarcoma Virus Long Terminal Repeat is a Strong Promoter When Introduced into a Variety of Eukaryotic Cells by DNA–Mediated Transfection," Proc. Natl. Acad. Sci. USA 79:6777–6781 (1982).

Boshart, M. et al., "A Very Strong Enhancer Is Located Upstream of an Immediate Early Gene of Human Cytomegalovirus," Cell 41:521–530 (1985).

Nakabayashi, H. et al., "Growth of Human Hepatoma Cell Lines with Differentiated Functions in Chemically Defined Medium," Cancer Res. 42:3858–3863 (1982).

Chang, L.–J. and Stoltzfus, C.M., "Gene Expression from Both Intronless and Intron–Containing Rous Sarcoma Virus Clones Is Specifically Inhibited by Anti–Sense RNA," Mol. Cell. Biol. 5(9):2341–2348 (1985).

Chang, L.–J. and Stoltzfus, C.M., "Inhibition of Rous Sarcoma Virus Replication by Antisense RNA," Virol. 61(3):921–924 (1987).

Marasco, W.A., et al., "Design, Intracellular Expression, and Activity of a Human Anti–Human Immunodeficiency Virus Type 1 gp120 Single–Chain Antibody," Proc. Natl. Acad. Sci. USA 90:7889–7893 (1993).

Kozak, M., "Point Mutations Define a Sequence Flanking the AUG Initiator Codon That Modulates Translation by Eukaryotic Ribosomes," Cell 44:283–292 (1986).

*Human Retroviruses and AIDS 1993*, I–II, Myers, G., et al. Eds. (1993) Theoretical Biology and Biophysics, Los Alamos, NM.

Graham, F.L. and van der Eb, A.J., "A New Technique for the Assay of Infectivity of Human Adenovirus 5 DNA", Virol., 52:456–467 (1973).

Peterlin, B.M. et al., "Elevated Levels of mRNA Can Account for the Trans–Activation of Human Immunodeficiency Virus", Proc. Natl. Acad. Sci. USA 83:9734–9738 (1986).

Chang, L.–J. et al., "Human Immunodeficiency Viruses Containing Heterologous Enhancer/Promoters Are Replication Competent and Exhibit Different Lymphocyte Tropisms," J. Virol. 67(3):743–752 (1993).

Vaishnav, Y.N. and Wong–Staal, F., "The Biochemistry of AIDS, " Ann. Rev. Biochem. 60:577–630 (1991).

Chaffee, S., et al., "Phenotypic Variation in the Response to the Human Immunodeficiency Virus Among Derivatives of the CEM T and WIL–2 B Cell Lines", J. Exp. Med. 168:605–621 (1988).

Ng, S.–Y. et al., "Evolution of the Functional Human β–Actin Gene and Its Multi–Pseudogene Family: Conservation of Noncoding Regions and Chromoomal Dispersion of Pseudogenes", Mol. Cell. Biol. 5(10):2720–2732 (1985).

Hunninghake, G.W. et al., "The Promoter–Regulatory Region of the Major Immediate–Early Gene of Human Cytomegalovirus Responds to T–Lymphocyte Stimulation and Contains Functional Cyclic AMP–Response Elements", J. Virol. 63(7):3026–3033 (1989).

Chen, H. et al., "Derivation of a Biologically Contained Replication System for Human Immunodeficiency Virus Type 1", Proc. Natl. Acad. Sci. USA 89:7678–7682 (1992).

Karlsson, R. et al., "A Chicken β–Actin Gene Can complement a Disruption of the *Saccharomyces cerevisiae* ACT1 Gene," Mol. Cell. Biol. 11(1):213–217 (1991).

Akagi, T. et al., "Murine Retroviral Vectors Expressing the *tax 1* Gene of Human T–Cell Leukemia Virus Type 1," Gene 106:255–259 (1991).

Miller, A.D., "Retrovirus Packaging Cells," Hum. Gene Ther. 1:5–14 (1990).

Miller, A.D. et al., "Use of Retroviral Vectors for Gene Transfer and Expression", Methods in Enzymology 217:581–591 (1993).

Sullenger, B.A. and Cech, T.R., "Tethering Ribozymes to a Retroviral Packaging Signal for Destruction of Viral RNA," Science 262:1566–1569 (1993).

Landau, N.R. and Littman, D.R., "Packaging System for Rapid Production of Murine Leukemia Virus Vectors with Variable Tropism," J. Virol. 66(8):5110–5113 (1992).

Adachi, A. et al., "Production of Acquired Immunodeficiency Syndrome–Associated Retrovirus in Human and Nonhuman Cells Transfected with an Infectious Molecular Clone," J. Virol. 59(2):284–291.

Chesebro, B. et al., "Failure of Human Immunodeficiency Virus Entry and Infection in CD4–Positive Human Brain and Skin Cells", J. Virol. 64(1):215–221 (1990).

A. Aldovini and R.A. Young, "Mutations of RNA and Protein Sequences Involved in Human Immunodeficiency Virus Type 1 Packaging Result in Production of Noninfectious Virus," J. Virol. 64(5):1920–1926 (1990).

A. Lever, et al., "Identification of a Sequence Required for Efficient Packaging of Human Immunodeficiency Virus Type 1 RNA into Virons," J. Virol. 63(9):4085–4087 (1989).

Selection of High Titer Packaging Cell Clones (RT Dot–Blot of Culture Supernatant)

RETROVIRAL EXPRESSION VECTORS CONTAINING MOMLV/CMV-IE/HIV-TAR CHIMERIC LONG TERMINAL REPEATS

FIELD OF THE INVENTION

The present invention relates to improved viral vectors useful for the expression of genes at high levels in human cells. These vectors also find use in anti-vital, anti-tumor and/or gene therapy. The improved vectors contain novel long terminal repeats which provide efficient promoters which function in a wide variety of human cell types. The improved vectors also contain additional packaging sequences which results in increased efficiency of packaging the recombinant vital genome.

BACKGROUND OF THE INVENTION

Viral vectors have been used as vehicles for the transfer of genes into many different cell types including whole embryos, fertilized eggs, isolated tissue samples and cultured cell lines. The ability to introduce and express a foreign gene in a cell is useful for the study of gene expression and the elucidation of cell lineages [Watson, J. D., et al. (1992) *Recombinant DNA*, Second Edition, W. H Freeman and Co., N.Y., pp. 256–263]. Retroviral vectors, which integrate into the cellular chromosome, have also been used for the identification of developmentally important genes via insertional mutagenesis [Watson, J. D., et al. (1992), supra, p. 261]. Viral vectors, in particular, retroviral vectors are also used in therapeutic applications (e.g., gene therapy), in which a gene (or genes) is added to a cell to replace a missing or defective gene or to inactivate a pathogen such as a virus.

1. Gene Therapy Strategies For AIDS

Gene therapy has also been proposed for the treatment of chronic infectious diseases such as acquired immunodeficiency syndrome (AIDS). Infection with the human immunodeficiency virus (HIV), a retrovirus, almost always leads to the development of AIDS in humans. Conventional therapeutic treatments, including anti-viral drugs such as reverse transcriptase inhibitors and soluble CD4 have failed to produce a cure for AIDS.

In the absence of any effective long-term therapeutic compounds, alternate strategies for anti-HIV therapy are needed. Recently suggested gene therapy approaches for the treatment of AIDS include: genetic decoy systems (trans-dominant mutants), soluble CD4 binding, toxin-targeting, anti-HIV ribozymes, antisense oligonucleotides, antisense RNA, anti-HIV intracellular antibodies, anti-HIV antigen-specific T cell transfer, etc. [For review see, Yu, M., Poeschla, E. and Wong-Staal, F. (1994) Gene Ther. 1:13)].

Antisense RNA inhibits gene expression by complementary binding to the target RNA. Antisense RNA transcripts have been used to inhibit replication of retroviruses. For example, antisense RNA was shown to inhibit replication of Rous sarcoma virus in transfected quail cells [Chang, L.-J. and Stoltzfus, C. M. (1985) Mol. Cell. Biol. 5:2341 and Chang, L.-J. and Stoltzfus, C. M. (1987) J. Virol. 61:921]. Since these initial studies, antisense regulation was applied extensively in basic and clinical studies. For example, the anti-HIV antisense oligonucleotide GEM91 is currently being tested in clinical trials in France and the U.S. [reported at the Xth International AIDS Meeting, Yokohama, Japan, Aug. 7-11, 1994].

A drawback to the use of antisense transcripts for therapeutic treatment of retroviral-induced disease is the need to produce large amounts of the antisense transcript in the infected cell. The recent development of trans-cleaving RNA enzymes (ribozymes) has perhaps superseded the antisense strategy by overcoming the stoichiometric limit of the antisense molecules involving RNA-RNA hybrids [Cech, T. R. and Bass, B. (1986) Ann. Rev. Biochem. 55:599]. A ribozyme of the "hammerhead" motif has been shown to act as an anti-HIV agent [Sarver, N. et al., (1990) Science 247:1222]. Human cells stably expressing a hammerhead ribozyme which specifically cleaves the HIV-1 gag transcript were shown to substantially reduce the amount of gag RNA produced upon infection of these cells with HIV-1. These results suggest that the use of hammerhead ribozymes specific for HIV transcripts may be an effective therapeutic agent provided an efficient means of delivering genes encoding the ribozyme to the cells of an infected individual is developed.

Recently, a ribozyme of the "hairpin" motif has been shown to act as an anti-HIV agent and has gained approval from the NIH Recombinant DNA Advisory Committee as a clinical protocol [Appendices, Human Gene Therapy (1994) 5:147]. In addition to the ribozyme approach, a handful of other genetic approaches including the use of retroviral vectors expressing gp160 [Yu, M., Poeschla, E. and Wong-Staal, F. (1994) Gene Ther. 1:13] or a trans-dominant HIV mutant Rev M10 [Bahner, L et al. (1993) J. Virol. 67:3199 and Appendices, Human Gene Therapy (1994) 5: 79], and adoptive transfer of gene-marked CD8[+] T cell clones into patients [Riddell, S. R., Human Gene Therapy (1994) 5:141] have also gained approval for clinical trials.

2. Gene Therapy Strategies For Inborn Errors Of Metabolism

In a few cases, gene therapy has been used to successfully correct inborn errors of metabolism using existing vector systems. For example, the adenosine deaminase gene has been introduced into peripheral blood lymphocytes and cord blood stem cells via retroviral vectors in order to treat patients with severe combined immunodeficiency due to a lack of functional adenosine deaminase [Culver, K. W. et al., (1991) Human Gene Therapy 2:107]. Partial correction of familial hypercholesterolemia has been achieved using existing retroviral vectors to transfer the receptor for low density lipoproteins (LDL) into hepatocytes. However, it was estimated that only 5% of the liver cells exposed to the recombinant virus incorporated the LDL receptor gene with the vector utilized [Grossman, M. et al., (1994) Nat. Genet. 6:335].

A number of single-gene disorders have been targeted for correction using gene therapy. These disorders include hemophilia (lack of Factor VIII or Factor IX), cystic fibrosis (lack of cystic fibrosis transmembrane regulator), emphysema (defective α-1-antitrypsin), thalassemia and sickle cell anemia (defective synthesis of β-globin), phenylketonuria (deficient phenylalanine hydroxylase) and muscular dystrophy (defective dystrophin) [See for review, Miller, A. D. (1992) Nature 357:455]. Human gene transfer trials have been approved for a number of these diseases.

3. Gene Therapy Strategies For Cancer

In addition to replacement of defective genes, it has been proposed that viral vectors could be used to deliver genes designed to stimulate immunity against or to otherwise destroy tumor cells. Retroviral vectors containing genes encoding tumor necrosis factor (TNF) or interleukin-2 (IL-2) have been transferred into tumor-infiltrating lymphocytes in patients [Kasid, A. et al. Proc. Natl. Acad. Sci. (1990) and Rosenberg, S. A. Human Gene Therapy 5: 140 (1994)]. It is postulated that the secretion of TNF or IL-2 will stimulate a tumor-specific immune response resulting in the destruction of the tumor or the recruitment of effective tumor infiltrating lymphocytes from nearby lymph nodes. Other proposed anti-tumor gene therapy strategies include the delivery of toxin genes to the tumor cell.

Applications of antisense genes or antisense oligonucleotides in inhibition of oncogenes and modulation of growth factors have the potential to reduce the mortality of cancer, in particular, human leukemia [For review see, Gewirtz A. M. (1993) Stem Cells 3:96 and Neckers, L. and Whitesell, L. (1993) Am. J. of Physiol. 265:L1].

4. Current Viral Vector Systems

In view of the wide variety of potential anti-HIV genes available for therapy, it is clear that an efficient means of delivering these genes is sorely needed in order to fulfill the promise of gene therapy as a means of treating HIV infection. Several viral systems including murine retrovirus, adenovirus, parvovirus (adeno-associated virus), vaccinia virus, and herpes virus have been developed as therapeutic gene transfer vectors [For review see, Nienhuis, A. W. et al. (1993) Hematology, Vol. 16: *Viruses and Bone Marrow*, Young, N. S. ed, Chapter 12, pp. 353–414]. Viral vectors provide a more efficient means of transferring genes into cells as compared to other techniques such as calcium phosphate or DEAE-dextran-mediated transfection, electroporation or microinjection. It is believed that the efficiency of viral transfer is due to the fact that the transfer of DNA is a receptor-mediated process (i.e., the virus binds to a specific receptor protein on the surface of the cell to be infected).

While many viral vector systems are available, virtually all of the current human gene therapy trials use retroviral vectors derived from the amphotropic Moloney murine leukemia virus (M-MuLV) for gene transfer [Miller, A. D. and Buttimore, C. (1986) Mol. Cell. Biol. 6:2895]. The M-MuLV system has several advantages: 1) this specific retrovirus can infect many different cell types, 2) established packaging cell lines are available for the production of recombinant M-MuLV viral particles and 3) the transferred genes are permanently integrated into the target cell chromosome. The established M-MuLV vector systems comprise a DNA vector containing a small portion of the retroviral sequence (the viral long terminal repeat or "LTR" and the packaging or "psi" signal) and a packaging cell line. The gene to be transferred is inserted into the DNA vector. The viral sequences present on the DNA vector provide the signals necessary for the insertion or packaging of the vector RNA into the viral particle and for the expression of the inserted gene. The packaging cell line provides the viral proteins required for particle assembly [Markowitz, D. et al. (1988) J. Virol. 62:1120].

The vector DNA is introduced into the packaging cell by any of a variety of techniques (e.g., calcium phosphate coprecipitation, electroporation, etc.). The viral proteins produced by the packaging cell mediate the insertion of the vector sequences in the form of RNA into viral particles which are shed into the culture supernatant. The M-MuLV system has been designed to prevent the production of replication-competent virus as a safety measure. The recombinant viral particles produced in these systems can infect and integrate into the target cell but cannot spread to other cells. These safeguards are necessary to prevent the spread of the recombinant virus from the treated patient and to avoid the possibility of helper virus-induced disease [Miller, A. D. and Buttimore, C. (1986) Mol. Cell. Biol. 6:2895 and Markowitz, D. et al., supra].

Despite these advantages, existing retroviral vectors are limited by several intrinsic problems: 1) they do not infect non-dividing cells [Miller, D.C., et al., (1990) Mol. Cell. Biol. 10:4239], 2) they produce only low titers of the recombinant virus [Miller, A. D. and Rosman G. J. (1989) BioTechniques 7:980 and Miller, A. D. (1992) Nature 357: 455], and 3) they express foreign proteins at low levels and often get turned-off or inactivated after integration [Miller, A. D. (1992) Nature 357: 455]. The low production of recombinant virus produced by the M-MuLV system (e.g., $10^6$/ml) compared to the adenoviral system (up to $10^2$/ml) means that human cells are infected at a very low efficiency. This low efficiency is particularly problematic when the target cell type is represented at very low numbers in the tissue to be infected. Although the hematopoietic stem cell is a preferred target for gene therapy in a large number of disorders, these cells are present at very low frequencies. For example, totipotent embryonic stem cells have been reported to occur at a frequency of $10^{-4}$ to $10^{-6}$ in bone marrow [B. R. Glick and J. J. Pasternak, *Molecular Biotechnology*, American Society for Microbiology, 1994, p. 412]. Thus, the low titer produced by existing M-MuLV vector systems is problematic for stem cell infection.

In addition, the promoter present in the M-MuLV LTR is quite weak compared with other viral promoters such as the human cytomegalovirus immediate early (CMV-IE) enhancer/promoter. In order to increase expression of the genes carried on the retroviral vector, internal promoters possessing stronger activities than the M-MuLV promoter have been utilized. However, the inclusion of an internal promoter to drive the expression of the inserted gene does not always lead to increased levels of expression [Robinson, D., Elliott, J. F. and Chang, L.-J. (1994) Gene Therapy in Press]. Apparently, the activity of the internal promoter is significantly decreased because of interference from the upstream M-MuLV promoter (i.e., transcriptional read-through interference). The dual transcription-unit construct is, however, a common feature in almost all M-MuLV vectors. Given these limitations, it is clear that improved vector systems are urgently needed to provide a means of delivering and expressing genes efficiently in mammalian cells, particularly human cells. Improved vectors will aid the study of gene expression and development and are necessary if the promise of gene therapy is to be realized.

SUMMARY OF THE INVENTION

The present invention contemplates improved viral vectors useful for the expression of genes at high levels in human cells. These vectors also find use in anti-viral, anti-tumor and/or gene therapy. The improved vectors contain novel long terminal repeats which provide efficient promoters which function in a wide variety of human cell types. The improved vectors also contain additional packaging sequences which result in increased efficiency of packaging the recombinant viral genome.

In one embodiment, the invention comprises a recombinant Moloney murine leukemia virus long terminal repeat which is activated by the human immunodeficiency virus 1 Tat protein, wherein the recombinant long terminal repeat has increased promoter activity relative to the wild type Moloney murine leukemia virus long terminal repeat in human cells. This increased activity can be readily assayed in a side-by-side comparison with both the recombinant LTR and the wild type LTR in a vector in host cells (e.g., human). In a preferred embodiment, the recombinant long terminal repeat contains the human cytomegalovirus immediate early enhancer/promoter and the HIV-1 TATA and TAR elements in place of the Moloney murine leukemia virus promoter element in the U3 region of the long terminal repeat. An example of such a construct is given having the sequence shown in SEQ ID NO:17.

In one embodiment, the recombinant long terminal repeat of this invention is contained on a recombinant murine amphotropic retroviral vector. This retroviral vector comprises in operable order: a) a first long terminal repeat; b) a packaging signal joined to this first long terminal repeat; and c) a second long terminal repeat joined to the packaging signal. In a preferred embodiment, the vector further comprises an oligonucleotide having a nucleotide sequence encoding a selectable marker gene, wherein the selectable marker gene is operably linked between the packaging signal and second long terminal repeat. It is contemplated that the selectable marker gene be a dominant selectable marker gene. In a preferred embodiment, the dominant selectable marker gene is the neomycin phosphoribosyltransferase gene. An example of such a preferred embodiment is given by the vector pLCTSN (deposited with the American Type Culture Collection).

In another embodiment, the recombinant long terminal repeat of the present invention includes a packaging signal comprising an extended Moloney murine leukemia virus packaging signal, wherein this extended packaging signal results in an increased packaging efficiency of the recombinant vector. An example of such a preferred embodiment is given by the vector pLGCTSN (deposited with the American Type Culture Collection). In an alternative preferred embodiment, the packaging signal comprises a human immunodeficiency virus packaging signal. It is contemplated that this human immunodeficiency virus packaging signal consist of the sequence listed in SEQ ID NO:10 or the sequence listed in SEQ ID NO:11.

In an alternative embodiment of the present invention, the recombinant murine amphotropic retroviral vector contains the following elements in operable order: a) a first long terminal repeat; b) a packaging signal joined to this first long terminal repeat; c) a polylinker joined to the packaging signal; and d) a second long terminal repeat consisting of the sequence listed in SEQ ID NO:17 joined to the polylinker.

In a further embodiment, the recombinant vector further comprises a selectable marker inserted into the polylinker. In a preferred embodiment, the selectable marker is a dominant selectable marker. It is contemplated that the dominant selectable marker is the neomycin phosphoribosyltransferase gene.

In one embodiment, the recombinant vector contains a packaging signal comprising an extended Moloney murine leukemia virus packaging signal. In a preferred embodiment, this packaging signal comprises a packaging signal derived from human immunodeficiency virus 1 (HIV-1). It is contemplated that the HIV-1 packaging signal consist of SEQ ID NO:10 or SEQ ID NO:11.

The present invention contemplates improving existing vectors. For example, the clinically approved retroviral vector pLNL6 was modified to generate pLLL (deposited with the ATCC). The present invention contemplates modification of the pLLL vector to generate other preferred vectors.

As noted above, the present invention contemplates that the improved viral vectors can be used for the expression of genes at high levels in human cells. Specifically, the present invention contemplates a method for expressing a gene in a human cell line, comprising the steps of a) providing a human cell line, and a retroviral vector containing the recombinant long terminal repeat of SEQ ID NO:17 and a gene of interest; and b) introducing the retroviral vector into the human cell line under conditions which allow the expression of the gene of interest.

In one embodiment of this method, the vector further contains a selectable marker. In a preferred embodiment, the selectable marker is a dominant selectable marker. It is contemplated that the dominant selectable marker is the neomycin phosphoribosyltransferase gene.

An alternative embodiment of this method comprises the further step of: c) exposing the human cell line to conditions, wherein the conditions allow only those human cells expressing the selectable marker to grow. In a preferred embodiment, the conditions comprise a selective medium. In a particularly preferred embodiment, the selective medium contains the antibiotic G418.

DEFINITIONS

Figure 1:
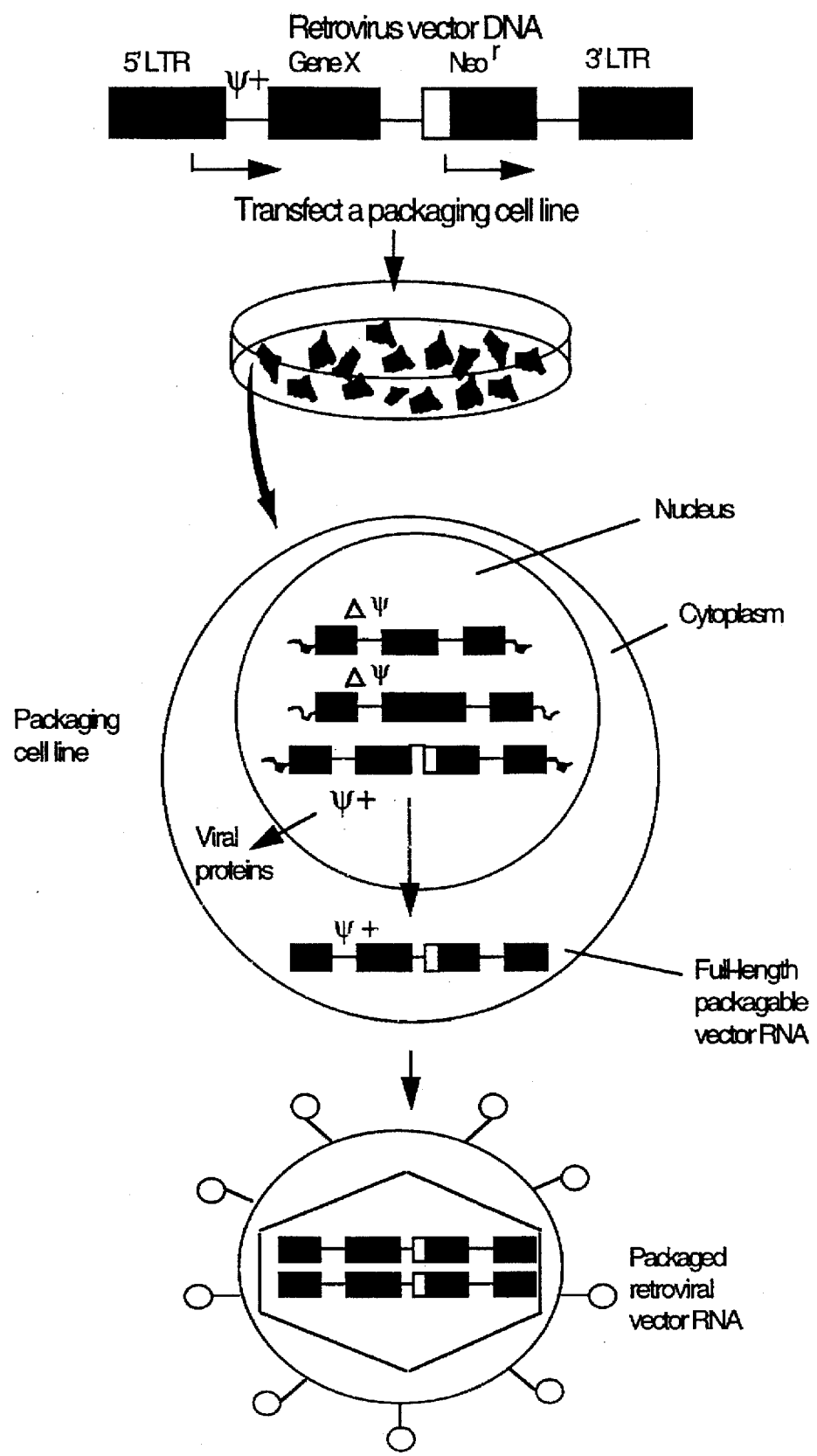
FIG. 1 is a simplified schematic illustration showing the production of packaged retrovirus vector RNA in a packaging cell line.

To facilitate understanding of the invention, a number of terms are defined below.

As used herein, the term "antisense" is used in reference to RNA sequences which are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter which permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

As used herein, the term "polyA$^+$ RNA" refers to RNA molecules having a stretch of adenine nucleotides at the 3' end. this polyadenine stretch is also referred to as a "poly-A tail". Eucaryotic mRNA molecules contain poly-A tails and are referred to as polyA$^+$ RNA.

As used herein, the term "ribozyme" is used in reference to RNA molecules with catalytic activity. It is intended that this term will encompass any catalytic RNA molecule, including, but not limited to, ribonuclease P, and pre-rRNA molecules.

As used herein, the terms "self-trimming" and "self-cleavage" refer to the ability of ribozymes and other molecules to cleave their own structures or sequences.

As used herein, the term "trans" is used in reference to the positioning of genes of interest on the different strands of nucleic acid (e.g., alleles present on the two chromosomes of a chromosomal pair). The term "trans-acting" is used in reference to the controlling effect of a regulatory gene on a gene present on a different chromosome. In contrast to promoters, repressors are not limited in their binding to the DNA molecule that includes their genetic information. Therefore, repressors are sometimes referred to as trans-acting control elements.

The term "trans-activation" as used herein refers to the activation of gene sequences by factors encoded by a regulatory gene which is not necessarily contiguous with the gene sequences which it binds to and activates. For example, the HIV-1 regulatory protein Tat is encoded by the tat gene and binds to and activates (i.e., trans-activates) expression from the HIV LTR.

As used herein, the term "cis" is used in reference to the presence of genes on the same chromosome. The term "cis-acting" is used in reference to the controlling effect of a regulatory gene on a gene present on the same chromosome. For example, promoters, which affect the synthesis of downstream mRNA are cis-acting control elements.

As used herein, the term "retrovirus" is used in reference to RNA viruses which utilize reverse transcriptase during their replication cycle. The retroviral genomic RNA is converted into double-stranded DNA by reverse transcriptase. This double-stranded DNA form of the virus integrates into the chromosome of the infected cell and is referred to as a "provirus." The provirus serves as a template for RNA polymerase II and directs the expression of RNA molecules which encode the structural proteins and enzymes needed to produce new viral particles. At each end of the provirus are structures called "long terminal repeats" or "LTRs". The LTR contains numerous regulatory signals including transcriptional control elements, polyadenylation signals and sequences needed for replication and integration of the viral genome. The vital LTR is divided into three regions called U3, R and U5.

The U3 region contains the enhancer and promoter elements. The U5 region contains the polyadenylation signals. The R (repeat) region separates the U3 and U5 regions and transcribed sequences of the R region appear at both the 5' and 3' ends of the viral RNA.

As used herein, the term "endogenous virus" is used in reference to an inactive virus which is integrated into the chromosome of its host cell (often in multiple copies), and can thereby exhibit vertical transmission. Endogenous viruses can spontaneously express themselves and may result in malignancies.

As used herein, the terms "amphotrope" and "amphotropic" are used in reference to endogenous viruses that readily multiply in cells of the species in which they were induced, as well as cells of other species.

As used herein, the term "ecotrope" and "ecotropic" are used in reference to endogenous viruses that multiply readily in cells of the species in which they were induced, but cannot multiply in cells of other species.

As used herein, the term "xenotrope" and "xenotropic" are used in reference to endogenous viruses that cannot infect cells of the species in which they were induced, but can infect and multiply in cells of other species.

As used herein, the term "provirus" is used in reference to a virus that is integrated into a host cell chromosome (or genome), and is transmitted from one cell generation to the next, without causing lysis or destruction of the host cell. The term is also used in reference to a duplex DNA sequence present in an eucaryotic chromosome, which corresponds to the genome of an RNA retrovirus.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

The term "T25 flask" refers to a tissue culture flask having a growth surface area of 25 square centimeters.

As used herein, the term "packaging signal" or "packaging sequence" refers to sequences located within the retroviral genome which are required for insertion of the viral RNA into the viral capsid or particle. Several retroviral vectors use the minimal packaging signal (also referred to as the psi sequence) needed for encapsidation of the viral genome. This minimal packaging signal encompasses bases 212 to 563 of the Mo-MuLV genome [Mann et al. (1983) Cell 33:153].

As used herein, the term "extended packaging signal" or "extended packaging sequence" refers to the use of sequences around the psi sequence with further extension into the gag gene. In Mo-MuLV this extended packaging sequence corresponds to the region encompassing base 1039 to base 1906 [Akagi, T. et al. (1991) Gene 106:255]. The frequently used M-MuLV vector, pLNL6 [Bender, M. A., et al. (1987) J. Virol. 61:1639], contains the entire 5' region of the genome including an extended packaging signal from bases 206 to 1039 of the Moloney murine sarcoma virus genome [numbering from Supplements and Appendices in *RNA Tumor Viruses*, 2nd Ed. (1985) pp. 986–988]. The inclusion of these additional packaging sequences increases the efficiency of insertion of vector RNA into viral particles.

As used herein, the term "packaging cell lines" is used in reference to cell lines that express viral structural proteins (e.g., gag, pol and env), but do not contain a packaging signal. For example, a cell line has been genetically engineered to carry at one chromosomal site within its genome, a 5'-LTR-gag-pol3'-LTR fragment that lacks a functional $psi^+$ sequence (designated as $\Delta psi$), and a 5'-LTR-env-3'-LTR fragment which is also $\Delta psi$ located at another chromosomal site. While both of these segments are transcribed constitutively, because the $psi^+$ region is missing and the viral RNA molecules produced are less than full-size, empty viral particles are formed.

When retroviral vector DNA is transfected into the cells, it becomes integrated into the chromosomal DNA and is transcribed, thereby producing full-length retroviral vector RNA that has a $psi^+$ sequence. Under these conditions, only the vector RNA is packaged into the viral capsid structures These complete, yet replication-defective, virus particles can then be used to deliver the retroviral vector to target cells with relatively high efficiency.

FIG. 1 is a simplified schematic showing the production of packaged retrovirus vector RNA in a packaging cell line. In this figure, the released viral particles carry a remedial gene (Gene X) and a selectable marker gene for resistance to neomycin ($Neo^r$).

As used herein, the term "remedial gene" refers to a gene whose expression is desired in a cell to correct an error in cellular metabolism, to inactivate a pathogen or to kill a cancerous cell. For example, the adenosine deaminase (ADA) gene is the remedial gene when carried on a retroviral vector used to correct ADA deficiency in a patient.

As used herein, the term "selectable marker" refers to the use of a gene which encodes an enzymatic activity that confers resistance to an antibiotic or drug upon the cell in which the selectable marker is expressed. Selectable markers may be "dominant"; a dominant selectable marker encodes an enzymatic activity which can be detected in any eucaryotic cell line. Examples of dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin and the bacterial xanthine-guanine phosphoribosyl transferase gene (also referred to as the gpt gene) which confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene which is used in conjunction with $tk^-$ cell lines, the CAD gene which is used in conjunction with CAD-deficient cells and the mammalian hypoxanthine-guanine phosphoribosyl transferase (hprt) gene which is used in conjunction with $hprt^-$ cell lines. A review of the use of selectable markers in mammalian cell lines is provided in Sambrook, J. et al., *Molecular Cloning: A Laboratory Manual* 2nd ed., Cold Spring Harbor Laboratory Press, New York (1989) pp.16.9–16.15.

As used herein, the terms "packaging sequence," "packaging signal," and "psi" are used in reference to the non-coding sequence required for encapsidation of retroviral RNA strands during viral particle formation.

As used herein, the term "retroviral vector" is used in reference to retroviruses which have been modified so as to serve as vectors for introduction of nucleic acid into cells.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in procaryotes usually include a promoter, an operator (optional), and a ribosome binding site, often along with other sequences. Eucaryotic cells are known to utilize promoters, enhancers, and termination and polyadenylation signals.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "genetic cassette" as used herein refers to a fragment or segment of DNA containing a particular grouping of genetic elements. The cassette can be removed and inserted into a vector or plasmid as a single unit.

The term "transfection" as used herein refers to the introduction of foreign DNA into eucaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

As used herein, the term "transduction" refers to the delivery of a gene(s) using a retroviral vector by means of infection rather than by transfection. For example, an anti-HIV gene carried by a retroviral vector can be transduced into a host cell through infection and provirus integration.

As used herein, the term "TATA element" or "TATA box" is used in reference to a segment of DNA, located approximately 19–27 base pairs upstream from the start point of eucaryotic structural genes, to which RNA polymerase binds. The TATA box is approximately 7 base pairs in length, often comprising the sequence "TATAAAA." The TATA box is also sometimes referred to as the "Hogness box."

The term "CAAT box" or "CAAT element" refers to a conserved DNA sequence located approximately 75 bp upstream from the start point of eucaryotic structural genes, to which RNA polymerase binds.

As used herein, the term "tat" is used in reference to the HIV gene which encodes "Tat," a protein which induces high-level expression of HIV genes.

As used herein, the term "long terminal repeat (LTR)" is used in reference to domains of base pairs located at the ends of retroviral DNA's. These LTRs may be several hundred base pairs in length. LTR's often provide functions fundamental to the expression of most eucaryotic genes (e.g., promotion, initiation and polyadenylation of transcripts).

As used herein, the term "TAR" is used in reference to the "trans-activation response" genetic element located in the U5 region of the HIV LTR. This element mediates the action of tat, by physically binding to the viral trans-activator tat.

As used herein, the term "adoptive transfer" is used in reference to the transfer of one function to another cell or organism. For example, in "adoptive immunity," transfer of an immune function is made from one organism to another through the transfer of immunologically competent cells.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\%\ G+C)$, when a nucleic acid is in aqueous solution at 1M NaCl (see e.g., Anderson and Young, Quantitative Filter Hybridization, in *Nucleic Acid Hybridization* (1985). Other references include more sophisticated computations which take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of "target" (defined below). In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, which is capable of hybridizing to another oligonucleotide of interest. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is further contemplated that the oligonucleotide of interest (i.e., to be detected) will be labelled with a reporter molecule. It is also contemplated that both the probe and oligonucleotide of interest will be labelled. It is not intended that the present invention be limited to any particular detection system or label.

As used herein, the term "target" refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195 and 4,683,202, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase [D. L. Kacian et al., Proc. Nat. Acad. Sci USA 69:3038 (1972)]. Other nucleic acid will not be replicated by this amplification enzyme. Similarly, in the case of T7 RNA polymerase, this amplification enzyme has a stringent specificity for its own promoters [M. Chamberlin et al, Nature 228:227 (1970)]. In the case of T4 DNA ligase, the enzyme will not ligate the two oligonucleotides where there is a mismatch between the oligonucleotide substrate and the template at the ligation junction [D. Y. Wu and R. B. Wallace, Genomics 4:560 (1989)]. Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences [*PCR Technology*, H. A. Erlich (ed.) (Stockton Press 1989)].

Some amplification techniques take the approach of amplifying and then detecting target; others detect target and then amplify probe. Regardless of the approach, nucleic acid must be free of inhibitors for amplification to occur at high efficiency.

As used herein, the terms "PCR product" and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "nested primers" refers to primers that anneal to the target sequence in an area that is inside the annealing boundaries used to start PCR [K. B. Mullis, et al., Cold Spring Harbor Symposia, Vol. II, pp.263–273 (1986)]. Because the nested primers anneal to the target inside the annealing boundaries of the starting primers, the predominant PCR-amplified product of the starting primers is necessarily a longer sequence, than that defined by the annealing boundaries of the nested primers. The PCR-amplified product of the nested primers is an amplified segment of the target sequence that cannot, therefore, anneal with the starting primers. Advantages to the use of nested primers include the large degree of specificity, as well as the fact that a smaller sample portion may be used and yet obtain specific and efficient amplification.

As used herein, the term "amplification reagents" refers to those reagents (deoxyribonucleoside triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule which is comprised of segments of DNA joined together by means of molecular biological techniques.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term "an oligonucleotide having a nucleotide sequence encoding a gene" means a DNA sequence comprising the coding region of a gene or in other words the DNA sequence which encodes a gene product. The coding region may be present in either a cDNA or genomic DNA form. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "transcription unit" refers to the segment of DNA between the sites of initiation and termination of transcription and the regulatory elements necessary for the efficient initiation and termination. For example, a segment of DNA comprising an enhancer/promoter, a coding region and a termination and polyadenylation sequence comprises a transcription unit.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. (defined infra).

Transcriptional control signals in eucaryotes comprise "promoter" and "enhancer" elements. Promoters and enhancers consist of short arrays of DNA sequences that interact specifically with cellular proteins involved in transcription [Maniatis, T. et al., Science 236:1237 (1987)]. Promoter and enhancer elements have been isolated from a variety of eucaryotic sources including genes in yeast, insect and mammalian cells and viruses (analogous control elements, i.e., promoters, are also found in procaryotes). The selection of a particular promoter and enhancer depends on what cell type is to be used to express the protein of interest. Some eucaryotic promoters and enhancers have a broad host range while others are functional in a limited subset of cell types [for review see Voss, S. D. et al., Trends Biochem. Sci., 11:287 (1986) and Maniatis, T. et al., supra (1987)]. For example, the SV40 early gene enhancer is very active in a wide variety of cell types from many mammalian species and has been widely used for the expression of proteins in mammalian cells [Dijkema, R. et al., EMBO J. 4:761 (1985)]. Two other examples of promoter/enhancer elements active in a broad range of mammalian cell types are those from the human elongation factor 1α gene [Uetsuki, T. et al., J. Biol. Chem., 264:5791 (1989), Kim, D. W. et al., Gene 91:217 (1990) and Mizushima, S. and Nagata, S., Nuc. Acids. Res., 18:5322 (1990)] and the long terminal repeats of the Rous sarcoma virus [Gorman, C. M. et al., Proc. Natl. Acad. Sci. USA 79:6777 (1982)] and the human cytomegalovirus [Boshart, M. et al., Cell 41:521 (1985)].

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

The term "factor" refers to a protein or group of proteins necessary for the transcription or replication of a DNA sequence. For example, SV40 T antigen is a replication factor which is necessary for the replication of DNA sequences containing the SV40 origin of replication. Transcription factors are proteins which bind to regulatory elements such as promoters and enhancers and facilitate the initiation of transcription of a gene.

Promoters and enhancers may bind to specific factors which increase the rate of activity from the promoter or enhancer. These factors may be present in all cell types or may be expressed in a tissue-specific manner or in virus infected cells. In the absence of such a factor the promoter may be inactive or may produce a low level of transcriptional activity. Such a low level of activity is referred to as a baseline or "basal" rate of activity. Additionally, viral promoter and enhancers may bind to factors encoded by the virus such that the viral promoter or enhancer is "activated" in the presence of the viral factor (in a virus infected cell or in a cell expressing the viral factor). The level of activity in the presence of the factor (i.e., activity "induced" by the factor) will be higher than the basal rate.

Different promoters may have different levels of basal activity in the same or different cell types. When two different promoters are compared in a given cell type in the absence of any inducing factors, if one promoter expresses at a higher level than the other it is said to have a higher basal activity.

The activity of a promoter and/or enhancer is measured by detecting directly or indirectly the level of transcription from the element(s). Direct detection involves quantitating the level of the RNA transcripts produced from that promoter and/or enhancer. Indirect detection involves quantitation of the level of a protein, often an enzyme, produced from RNA transcribed from the promoter and/or enhancer. A commonly employed assay for promoter or enhancer activity utilizes the chloramphenicol acetyltransferase (CAT) gene. A promoter and/or enhancer is inserted upstream from the coding region for the CAT gene on a plasmid; the plasmid is introduced into a cell line. The levels of CAT enzyme are measured. The level of enzymatic activity is proportional to the amount of CAT RNA transcribed by the cell line. This CAT assay therefore allows a comparison to be made of the relative strength of different promoters or enhancers in a given cell line. When a promoter is said to express at "high" or "low" levels in a cell line this refers to the level of activity relative to another promoter which is used as a reference or standard of promoter activity.

The improved recombinant vectors of the invention contain recombinant long terminal repeats (LTRs) in which the M-MuLV U3 region is replaced by the CMV-IE enhancer/promoter and the HIV TATA and TAR elements. This novel LTR (SEQ ID NO:17) exhibits increased promoter activity in most human cell lines than does the parental M-MuLV LTR. The recombinant LTR has a higher basal promoter activity in human cells as compared to the parental or wild type M-MuLV LTR. Furthermore, the recombinant LTR is inducible by the Tat protein such that in cells expressing the HIV Tat protein, the activity of the recombinant LTR is enhanced.

When it is said that the recombinant LTR exhibits stronger or increased promoter activity than the parental M-MuLV LTR this means that, relative to the value obtained for the activity of the M-MuLV promoter, the recombinant LTR (present in pMCT; SEQ ID NO:17) exhibits a value at least 2 fold higher (typically 2 to 10 fold higher values obtained when promoter activity is measured by determining the percent conversion of chloramphenicol to acetylated chloramphenicol) than that obtained using the M-MuLV LTR in the HeLa, HepG2 and HUH-7 cell lines. The promoter activity may be measured by placing a reporter gene, such as the CAT gene, under the control of either the M-MuLV LTR or the pMCT LTR. Human cell lines are transfected with the DNAs and CAT activity is assayed. A comparison between the activity levels (judged by the conversion of chloramphenicol to acetylated chloramphenicol) is made by obtaining reproducible mean values from at least three independent transfection experiments; the values are normalized to the expression of an internal control gene to account for difference in uptake of DNA or cell viability between experiments and within an experiment.

The recombinant LTR of SEQ ID NO:17 is further characterized by its ability to be up-regulated in the presence of the HIV Tat protein. The promoter activity of the recombinant LTR is said to be inducible by Tat. This means that the level of activity from the recombinant LTR increases at least 2 fold (typically 2 to 16 fold higher values obtained when promoter activity is measured by determining the percent conversion of chloramphenicol to acetylated chloramphenicol) in the presence of the Tat protein in a human cell line when compared to the activity in the same human cell line in the absence of Tat. The ability of a promoter to be activated by Tat is measured by placing a reporter gene (e.g., CAT gene) under the direction of the promoter (i.e., downstream of the promoter sequences) and introducing the DNA construct into a human cell in the presence and the absence of a construct directing the expression of the Tat protein. The activity of the reporter gene is measured using a suitable assay (such as the CAT assay). A comparison between the activity levels (judged by the conversion of chloramphenicol to acetylated chloramphenicol when the CAT assay is employed) is made by obtaining reproducible mean values from at least three independent transfection experiments; the values are normalized to the expression of an internal control gene to account for difference in uptake of DNA or cell viability between experiments and within an experiment.

The presence of "splicing signals" on an expression vector often results in higher levels of expression of the recombinant transcript. Splicing signals mediate the removal of introns from the primary RNA transcript and consist of a splice donor and acceptor site [Sambrook, J. et al., *Molecular Cloning: A Laboratory Manual*, 2nd ed., Cold Spring Harbor Laboratory Press, New York (1989) pp. 16.7–16.8]. A commonly used splice donor and acceptor site is the splice junction from the 16S RNA of SV40.

Efficient expression of recombinant DNA sequences in eucaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is one which is isolated from one gene and placed 3' of another gene. A commonly used heterologous poly A signal is the SV40 poly A signal. The SV40 poly A signal is contained on a 237 bp Bam HI/Bcl I restriction fragment and directs both termination and polyadenylation [Sambrook, J., supra, at 16.6–16.7].

Eucaryotic expression vectors may also contain "viral replicons" or "viral origins of replication." Viral replicons are viral DNA sequences which allow for the extrachromosomal replication of a vector in a host cell expressing the appropriate replication factors. Vectors which contain either the SV40 or polyoma virus origin of replication replicate to high copy number (up to $10^4$ copies/cell) in cells that express the appropriate viral T antigen. Vectors which contain the replicons from bovine papillomavirus or Epstein-Barr virus replicate extrachromosomally at low copy number (~100 copies/cell).

The term "stable transfection" or "stably transfected" refers to the introduction and integration of foreign DNA into the genome of the transfected cell. The term "stable transfectant" refers to a cell which has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells which have taken up foreign DNA but have failed to integrate this DNA.

As used herein, the term "gene of interest" refers to the gene inserted into the polylinker of an expression vector. When the gene of interest encodes a gene which provides a therapeutic function (such as an anti-HIV gene), the gene of interest may be alternatively called a remedial gene.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The PAK sequences derived from the HIV-1, when present on a retroviral vector in a cell which also expresses the HIV-1 genome, is "capable of inhibiting the insertion" of said HIV-1 genome into HIV-1 particles. This inhibition or interference in the packaging of the HIV-1 genome is detected by a drop in the amount of infectious HIV-1 particles in the cell expressing both the PAK sequences and HIV. The art knows of several ways to measure the titer or number of infectious HIV-1 particles. An inhibition of at least two-fold in the titer of infectious HIV particles is considered significant.

The term "lipofection" refers to a technique for the introduction of nucleic acids into a cell. Lipofection utilizes a liposome formulation of cationic lipids such as N-[1-(2, 3-dioleyloxy)propyl]-N,N,N-trimethylammonium chloride or the polycationic lipid 2,3 -dioleyloxy-N-[2 (sperminecarboxamido)ethyl]-N,N-dimethyl-1-propanaminiumtrifluoroacetate and a neutral lipid such as dioleoyl phosphatidylethanolamine. The liposomes complex with nucleic acids and the liposome-nucleic acid complex is used to facilitate the introduction of the nucleic acids into cells. Lipofectin™ Reagent and LipofectAMINE™ Reagent are commercially available from Life Technologies, Inc., Gaithersburg, Md. Lipofection is carried using either of these reagents according to the manufacturer's protocols.

The term "calcium phosphate co-precipitation" refers to a technique for the introduction of nucleic acids into a cell.

The uptake of nucleic acids by cells is enhanced when the nucleic acid is presented as a calcium phosphate-nucleic acid coprecipitate. The original technique of Graham and van der Eb (1973) Virol. 52:456 has been modified by several groups to optimize conditions for particular types of cells. The art is well aware of these numerous modifications. The experimental section herein describes a modification of this technique in Example 1 which is suitable for the introduction of DNA into adherent human cell lines.

The term "Northern Blot" as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (Sambrook, J. et al., *Molecular Cloning: A Laboratory Manual*, Cold Spring Harbor Press, Cold Spring Harbor, N.Y., pp 7.39–7.52)

The term "dot blot" as used herein refers to spotting a sample of containing protein or nucleic acid onto a solid support. The solid support is then probed with a labeled nucleic acid or antibody probe to detect the protein or nucleic acid species of interest (For example, see Sambrook, supra at 7.53 for RNA dot blots). Alternatively the reaction products of an assay containing a radioactive substrate can be spotted onto a solid support and the unincorporated substrate washed prior to exposure of the support to X-ray film.

DESCRIPTION OF THE INVENTION

The invention provides novel retroviral vectors having improved promoter function, increased expression from inserted genes and increased packaging efficiency. These novel vectors are suitable for the introduction and expression of genes at high levels in human cells as well as for anti-HIV therapy and general gene therapy applications.

Improved Retroviral Vectors

Most of the currently approved gene therapy protocols utilize amphotropic M-MuLV-based vectors, such as pLNL6 [SEQ ID NO:1; Bender, M. A., et al. (1987) J. Virol. 61:1639]. Accumulated experience with this vector has led to the realization that the activity of the M-MuLV LTR is not very strong. In addition, the activity of this LTR in different cell types is unpredictable.

To create an improved retroviral vector suitable for a wide variety of gene expression studies and gene therapy applications, the clinically approved gene therapy vector pLNL6 was modified. The improved vector contains a recombinant LTR which comprises M-MuLV and CMV enhancer elements, two TATA promoters (from HIV and M-MuLV) and the HIV-1 TAR element. The upstream TATA box derived from HIV-1, directs the synthesis of TAR-containing mRNAs. TAR-containing mRNA is responsive to the HIV-1 Tat protein. The downstream TATA box is derived from the M-MuLV, and functions to direct the synthesis of mRNAs lacking the TAR element. This dual-promoter design allows high basal levels of mRNA to be synthesized from the vector sequences in the absence of the Tat protein (i.e., for general gene therapy applications). In the presence of the Tat protein (i.e., in HIV infected cells), this dual promoter is induced and directs the production of high levels of mRNA. This improved vector, termed pLCTSN, directs higher levels of expression from inserted genes than does the parental pLNL6 vector. Therefore, the pLCTSN vector is useful for the delivery of a wide variety of genes, including anti-HIV genes.

To improve the packaging efficacy of these vectors, extended packaging signals and a 3' splice acceptor sequence from the M-MuLV genome were added creating the pLGCTSN vector. These modifications increase the efficiency of packaging the vector RNA into viral particles allowing the production of high-titer recombinant virus stocks. High-titer stocks are needed when the target cells are present in low frequency in the tissue being infected (i.e., bone marrow stem cells). Addition of the extended packaging signal provides for competition between the anti-HIV genomes (provided by the vector) and the HIV genome (present in the infected cell).

These newly engineered retroviral vectors are useful as vectors to allow the introduction and study of genes in human cells. These vectors find utility in the area of the study of mammalian gene expression as well as in general gene therapy applications. For example, the pLCTSN and the pLGCTSN vectors exhibited higher promoter activities in hepatoma cell lines [HepG2 (ATCC HB 8065) and HUH-7 (Nakabayashi, H. et al. (1982) Cancer Res. 42:3858)] than the conventional pLNL6 vector. Most importantly, the vector pLCTSN has demonstrated prolonged stability in the hepatoma cells and epithelioid cells [HeLa cells (ATCC CCL 2)]. Some of the obstacles faced by the current gene therapy vectors lie in the poor expression level and the lack of long-term performance. It is contemplated that the vectors of the present invention will be used in therapeutic gene therapy.

Improved Vectors For The Study Of Gene Expression In HIV-Infected Cells

In addition to their use as delivery vehicles of genes for general gene expression studies, the improved vectors, pLCTSN and pLGCTSN are useful for the delivery of genes, including anti-HIV agents, to HIV-infected cells. As discussed above, the novel LTR contained on these vectors contains the HIV-1 TATA box which directs the synthesis of TAR-containing mRNAs. TAR-containing mRNAs are responsive to the HIV-1 Tat protein (present in HIV-infected cells). The novel LTRs direct high levels of mRNAs in the presence of Tat in infected cells. Therefore, the pLCTSN vector is useful for the delivery of genes, including anti-HIV genes, to HIV-infected cells.

Examples of anti-HIV genes include anti-HIV ribozymes [Chang, L.-J. and Stoltzfus, C. M. (1985) Mol. Cell. Biol. 5:2341; Chang, L.-J. and Stoltzfus, C. M. (1987) J. Virol. 61:921; and Sarver, N. E. M. et al. (1990) Science 247:1222] and intracellular single chain antibody genes [Marasco, W. A. et al. (1993) Proc. Natl. Acad. Sci. USA 90:7889]. Gene sequences encoding anti-HIV genes are inserted into the improved retroviral vectors to yield anti-HIV vectors.

To further improve the therapeutic efficacy of these vectors, packaging sequences from the HIV-1 genome were added. The addition of the HIV-1 packaging signal provides for competition between the anti-HIV genomes (provided by the vector) and the HIV genome (present in the HIV infected cell). This in vivo competition results in decreased HIV production by infected cells, as many of the virus particles will contain the anti-HIV genome (e.g., pseudotype particles) rather than the HIV-1 genome. In addition to reducing HIV production, vectors containing HIV-1 packaging signals allow for the access of the therapeutic anti-HIV vector to the target HIV genome.

DETAILED DESCRIPTION OF THE INVENTION

The invention provides novel long terminal repeat (LTR) constructs and improved retroviral vectors. The improved vectors contain novel LTRs which results in vectors having improved promoter function, increased expression of inserted genes and increased packaging efficiency. It is contemplated that these novel vectors will be useful for anti-HIV therapy, as well as other gene therapy applications. Here, the detailed description involves construction of novel vectors through reconstruction of LTRs from approved vectors and various assays utilized to assess their functions.

Reconstruction Of The M-MuLV LTR Using A Clinically Approved Gene Therapy Vector To improve the expression of genes from existing M-MuLV-based gene therapy vectors, the M-MuLV LTR was modified to include a truncated CMV-IE enhancer element and the HIV-1 TAR element. This modification produces a hybrid promoter which exhibits high basal activity and which is inducible by Tat to higher levels.

The clinically approved retroviral vector pLNL6 was used as a starting point. The retroviral vector pLNL6 is 6145 bp in length, and contains a M-MuLV promoter in the 3' LTR and a murine sarcoma virus (MSV) promoter in the 5' LTR [Bender, M. A., et al. (1987), supra]. For ease in subsequent cloning steps, the few cloning sites and the internal SV-neo gene in pLNL6 were replaced with the synthetic polylinker shown below to generate pLLL. pLNL6 was digested with ClaI and BclI. The digested vector was purified and a double stranded insert containing the polylinker site was inserted. This double stranded insert was made by annealing the following two oligonucleotides together. 5'-GATCTAAGCTTGCGGCCGCAGATCTCGAGCCA TGGATCCTAGGCCTGATCACGCGTCGACTCGCGAT-3' (SEQ ID NO:2) and 5' CGATCGCGAGTCGACGCGT- GATCAGGCCTAGGATCCATGGCTCGAGATC TGCGGCCGCAAGCTTA-3' (SEQ ID NO:3).

After annealing the above oligonucleotides, the resulting DNA fragment contains restriction sites for HindIII, NotI, BglII, XhoI, NcoI, BamHI, AvrII, StuI, BclI, MluI, SalI, NruI, and ClaI. The digestion of pLNL6 followed by the insertion of the annealed oligonucleotides resulted in the deletion of the sequences present from BclI (nt 1625) to ClaI (nt 3049) in pLNL6 (SEQ ID NO:1).

To obtain a vector carrying a selective marker for cell selection, pLSN was constructed by inserting a fragment from BamHI to StuI of pLNSX containing the SV40 promoter into the BamHI and StuI sites of pLLL to obtain pLLLSV40. The amplified neo gene was isolated by amplifying the neo gene using the polymerase chain reaction (PCR). pLNSX was used as the template and the following oligonucleotides were used to amplify the neo gene: 5'-AAGCTTGATCACCACCAT GATTGAACAAGATGG-3' (SEQ ID NO:4) and 5'-CCGGATCCGTCGACCCCAGA GTCCCGCTCAGAAG-3' (SEQ ID NO:5). The amplification products were then digested with BclI and BamHI and cloned into BclI-digested pLLLSV40 to generate pLSN. The primers used to amplify the neo gene contained the modified translation initiation control sequence -CCACCATG- [Kozak, M. (1986) Cell 44:283]. The use of this modified translation initiation control sequence greatly increased the strength of the neomycin resistance gene in tissue culture cells (e.g., HeLa, 3T3, and HepG2, data not shown).

To create a vector containing a modified M-MuLV LTR only the 3' LTR was reconstructed, since it would replace the 5' LTR after one round of reverse transcription. Sequences upstream of the M-MuLV TATA box in the U3 of the 3' LTR were modified to include a genetic cassette containing both the CMV-IE enhancer/promoter and the TAR sequence, or the TAR sequence alone.

To achieve this, the 3' LTR from pLSN was isolated by ClaI and NdeI digestion (corresponds to nucleotides 3049–4082 of pLNL6) and cloned into the pSP72 vector (Promega) between the ClaI and NdeI sites thus generating a subclone containing only one M-MuLV LTR (pSP72-3'LTR). To pSP72-3'LTR, fragments containing the HIV-1 TAR and a CMV-TAR DNA fragment were inserted by the following series of steps. First, the SacI site near the M-MuLV LTR TATA box (nucleotide 3604 of the pLNL6 numbering system) was changed to an EcoRI site by annealing an EcoRI adapter (5'-GAATTCAGCT-3'). The HIV-1 TAR fragment (~200 bp) was made by PCR using pU3-R-CAT [Chang, et al. J. Virol. 67:743 (1993)] and the following primer pair: 5'-GCATCTAGAGTACTTCAAGAACTGC-3' (SEQ ID NO:6) (this primer corresponds to sequences near the HIV-1 TATA box and provides an XbaI site) and 5'-GGGAATTCGAGGCTTAAGCAGTGGGTTCC-3' (SEQ ID NO:7) (corresponds to sequences 3' to the HIV TAR and provides an EcoRI site).

The CMV-TAR fragment (~343 bp) was made by PCR using dl.kB/Sp1 CMV-IEa U3-R-CAT as the template and a primer pair consisting of: 5'-CCGGAGTAGCT AGCTGGAGTTCCGC-3' (SEQ ID NO:8) (corresponds to sequences located 5' to the CMV-IEa element and provides an NheI site) and SEQ ID NO:6 (listed above; i.e., the same 3' primer used to generate the TAR fragment). The two amplified fragments were digested with XbaI (for the TAR construct) or NheI (for CMV-TAR) and EcoRI, and cloned into the XbaI-EcoRI digested modified pSP72-3'LTR (contains an EcoRI site in place of the SacI site).

The identities of the two final products pMT and pMCT, were confirmed by restriction enzyme digestion and sequencing. To make the CAT reporter constructs, the cat-SV40 polyA fragment (~1631 bp) was obtained by digesting 5 μg of the pU3-R-CAT with HindIII and BamHI. The cat-SV40 polyA fragment was gel-purified and the ends were made blunt using T4 polymerase. An Asp718 linker [5'-GCTAGCGGT ACC-3' (SEQ ID NO:9)] was ligated to the blunt ends and the fragment was cloned into the Asp718-digested pMT or pMCT to generate pMT-cat and pMCT-cat.

Generation Of Retroviral Vectors Comprising Recombinant 3'LTRs

Both pMT and pMCT are single LTR plasmids. A four-fragment ligation procedure was used to construct the two-LTR packaging vectors pLCTSN and pLTSN. The vector was pLSN digested with SacII and KpnI. The three fragments inserted sequentially were SacII to XhoI of pLSN, XhoI to NheI of pLSN, and NheI to KpnI of pMCT or pMT.

Further modification of the gene therapy vector included generation of packaging and splicing-signal modified retroviral vectors by insertion of a fragment containing an extended packaging signal (from the gag gene) and a 3' splice site (from the env gene) from the M-MuLV genome. To accomplish this, a SpeI-BamHI fragment of pDGLtax/rex [Akagi, T. et al. Gene 106:255 (1991)] was cloned into pLCTSN digested with the same set of enzymes as used to generate pLGCTSN above.

Improved Efficiency of Promoter Activity in Human Cells

Promoter activities of the modified LTR in the presence or absence of the HIV-1 Tat were tested by transfecting the CAT reporter constructs described above into a panel of human cell lines. The level of CAT enzyme activity produced in the transfected cell lines is used to compare the relative strength of different promoter constructs. These cell lines included hepatoma cell lines, T and B lymphoid cell lines and an epithelioid cell line. The pMCT construct exhibited high promoter activity in the absence of Tat. In the presence of Tat, the pMCT LTR was trans-activated significantly (2 to 16-fold increase in activity seen in the presence of Tat).

On the other hand, the M-MuLV-TAR (pMT) construct was not found to be ideal because it demonstrated low basal activity (i.e., activity in the absence of Tat) and was not responsive to Tat. As shown in Example 4 (Table 1), in comparison with an already strong CMV-IE promoter, the MuLV-CMV-TAR (pMCT) promoter exhibited a 2-fold higher basal activity and was further activated 4-5 times when Tat was present as judged by the amount of CAT activity present in the transfected cell lines.

These results indicate that the M-MuLV LTR and HIV TAR combination (pMT) is not sufficient to make the M-MuLV LTR Tat-responsive, but Tat can trans-activate the pMCT promoter. Significantly, the CMV-TAR modification renders the M-MuLV promoter responsive to the HIV-1 Tat.

This conclusion was yet further supported by assays using a T-lymphoid cell line CEM-TART [Chen, H. et al. (1992) Proc. Natl. Acad. Sci. USA 89:7678] in which the Tat protein is expressed constitutively. CEM-TART cells were electroporated with a series of plasmid DNAs and the CAT reporter gene expression was determined. The result of this study indicated that the pMCT promoter exhibited the highest activity among the M-MuLV LTR, CMV-IE and HIV-1 LTR promoters in the human cell lines tested. Therefore, for the purpose of targeting HIV-infected cells, the pMCT construct appears to be ideal, since it exhibits high activity in the absence of Tat, and is strongly activated when Tat is present (i.e., during HIV infection).

In summary, pMCT was found to exhibit promoter activity at levels higher than the pLLL (M-MuLV promoter itself) in most of the human cell lines tested and much better than the pLLL in some hepatoma (HepG2, HuH-7) and lymphoid cell lines (H9, CEM, AA2, CEM-TART). The pMCT promoter was trans-activated by HIV-1 Tat in all the human cell types tested. Thus, the newly designed vector appears to be very useful for anti-HIV and general gene therapy applications as well as for the expression of genes in human cell lines.

Determination Of The Transcription Initiation Sites In The Modified LTR

Preliminary studies indicated that the modified CMV/TAR M-MuLV LTR, which worked well in human cells, is less active than the native M-MuLV LTR in mouse cells (e.g., 3T3). It is possible that the double TATA-box feature does not work well in mouse cells. In general, for the selection of packaging producer cell clones, ecotropic virus infection is preferred to DNA transfection. The poor expression level of the recombinant CMV/TAR M-MuLV LTR in mouse cells limits the use of the ecotropic infection method because the modified 3' LTR, which is to be reverse transcribed and relocated to the 5' end, would not be active in mouse cells. Nonetheless, long-term producer cells (PA317) have been generated by DNA transfection and have not had problems with stability (producing virus having average liters of 104 to 105 per ml, see Example 7, Table. 3).

Because the CMV/TAR M-MuLV LTR construct contains both the MuLV TATA box and the HIV TATA box, it is possible that both direct transcription initiation. To determine the transcription initiation sites of the new vector, the initiation sites of mRNA from HepG2 cells transfected with pMCT-cat plasmid were analyzed by RNase mapping. Cytoplasmic polyA$^+$ RNA from transfected HepG2 cells was harvested and analyzed by Northern blotting and RNA protection. As discussed in Example 5, the results indicated that both HIV and M-MuLV transcription initiation sites were used, but the upstream HIV transcription initiation site was preferred to the downstream M-MuLV initiation site. In addition, quantitation of the relative amounts of RNA produced from the pMCT promoter in the presence or absence of Tat confirmed that the pMCT transcription was trans-activated by Tat (See Example 5, FIGS. 14 and 15).

Improved Packaging Efficiency

In addition to the generation of improved promoters, the ability to increase the vector titer of the packaging cells is yet another key issue in retroviral gene therapy. Most clinical gene transfer studies involve infection of hematopoietic stem cells and therefore require high titers of recombinant virus. Efficient stem cell transduction requires the use of viral stocks having a titer of at least $10^6$ viral particles/ml.

To improve the packaging efficiency of the traditional vector, an additional M-MuLV packaging signal was cloned into the vector. Along with the extra packaging signal, a 3' splice site was also included. This modification stabilized transcripts expressed by the vector and enhance its packaging efficiency. The packaging efficiencies of these new vectors, including pLSN, pLCTSN and pLGCTSN, were studied using the PA317 packaging Cells (Example 7). Vector DNA was introduced into PA317 cells using lipofectamine (BRL). Culture supernatant containing the packaged vector RNA from the transfected cells was removed and used to infect HeLa or Huh7 cells. The infected cells were cultured in medium containing the antibiotic G418 (all three vectors contain the neo gene and therefore confer resistance to G418 upon the infected cell). The number of G418-resistant colonies produced per ml of culture supernatant used gives the titer or packaging efficiency of the vector in PA317 cells. The results showed that the packaging efficiency of pLGCTSN, which contained an additional packaging signal, increased about 3-5 fold over the others (pLNL6, pLSN, or pLCTSN). In addition, expression of the new vector (pLGCTSN) was consistently 3-10 times better than the pLCTSN or the pLSN constructs as judged by CAT assays [All three vectors contain the CAT gene; therefore, the level of CAT activity produced from a vector can be used to determine the activity of the LTR on a given vector relative to another vector(s) in CAT assays].

Long-Term Stability Of Gene Expression From The Novel Vectors

The long term stability of the modified vector was studied in HeLa and HepG2 cells. Cells infected with pLSN, pLCTSN, or pLGCTSN were selected by growth in the presence of G418 (resistant colonies took about two weeks to establish). Selected [i.e., G418-resistant (G418$^r$)] cells were then assayed for CAT activity. Results of this study showed that CAT expression from pLCTSN was more stable than CAT expression from pLGCTSN in HeLa and HepG2 cells. In addition, the level of CAT expression of pLCTSN was also 2-3 fold higher than the parental construct pLSN as judged by CAT assays on HeLa cells 1 to 2 months after transduction with these vectors. Stable expression of CAT from the pLGCTSN vector was achieved in stably transduced HeLa cells two months after transduction. The pLGCTSN vector also remained responsive to Tat trans-activation two months after introduction of the vector into HeLa cells. Thus, both the pLCTSN and pLGCTSN vectors permit the long term expression of inserted genes in human cells; furthermore this expression remains responsive to induction by the Tat protein.

Addition of HIV-1 Packaging Sequences to the Improved Vectors

Traditional gene therapy vectors can only infect the target cell once because of the lack of M-MuLV structural proteins in the target cells. To further modify the gene therapy vector for anti-HIV purposes, sequences in HIV that are essential to genome packaging were cloned into pLLLgpt (described in Example 2, infra). Two synthetic packaging sequences were designed based upon the consensus sequence derived from several HIV-1 isolates [sequences of the isolates and the consensus sequence were from *Human Retroviruses and AIDS* 1993, I–II, Myers, G., et al. eds. (1993) Theoretical Biology and Biophysics, Los Alamos, N. Mex.]. PAK 100 (SEQ ID NO:10) contains approximately 100 nucleotides derived from HIV-1 and a restriction recognition site for BamHI at the 3' end and a cohesive overhang at the 5' end for SalI. PAK 140 (SEQ ID NO:11) contains approximately 140 nucleotides derived from HIV-1 and overhanging ends compatible with BamHI and SalI.

The presence of PAK140 sequences on vector RNA reduces the production of infectious HIV particles in a cell expressing both the HIV genome and the PAK-containing vector genome.

The sequences contained in either PAK100 or PAK140 do not appear in any isolate of HIV-1; they contain mutated splice donor sequences and PAK140 replaces sequences near the ATG of the gag gene with sequences not found in known HIV isolates. These sequences are derived from but are not identical to the consensus sequence derived from a comparison of several HIV-1 isolates.

Upon transduction, expression of HIV packaging proteins in the target cells (HIV-infected) would allow packaging of the M-MuLV vector containing the HIV-1 packaging sequences (PAK100 or PAK140) into HIV particles. This design can potentially expand the therapeutic efficacy of the anti-HIV antisense and ribozyme vectors by both reducing the amount of viral particles containing the HIV genome produced by the infected cell and by allowing access of the therapeutic anti-HIV vector to the target HIV genome. These packaging sequences are cloned into the vector pLCTSN, which is then transfected into HIV-infected cells to determine if the vector sequences are packaged into HIV particles.

EXPERIMENTAL

The following examples serve to illustrate certain preferred embodiments and aspects of the present invention and are not to be construed as limiting the scope thereof.

In the experimental disclosure which follows, the following abbreviations apply: M (molar); mM (millimolar); μM (micromolar); mol (moles); mmol (millimoles); μmol (micromoles); nmol (nanomoles); g (gravity); gm (grams); mg (milligrams); μg (micrograms); pg (picograms); L (liters); ml (milliliters); μl (microliters); cm (centimeters); mm (millimeters); μm (micrometers); nm (nanometers); hr (hour); min (minute); msec (millisecond); °C. (degrees Centigrade); AMP (adenosine 5'-monophosphate); cDNA (copy or complimentary DNA); DTT (dithiotheritol); $ddH_2O$ (double distilled water); dNTP (deoxyribonucleotide triphosphate); rNTP (ribonucleotide triphosphate); ddNTP (dideoxyribonucleotide triphosphate); bp (base pair); kb (kilo base pair); TLC (thin layer chromatography); tRNA (transfer RNA); nt (nucleotide); VRC (vanadyl ribonucleoside complex); RNase (ribonuclease); DNase (deoxyribonuclease); poly A (polyriboadenylic acid); PBS (phosphate buffered saline); OD (optical density); HEPES (N-[2-Hydroxyethyl]piperazine-N-[2-ethanesulfonic acid]); HBS (HEPES buffered saline); SDS (sodium dodecyl sulfate); Tris-HCl (tris[Hydroxymethyl] aminomethanehydrochloride); rpm (revolutions per minute); ligation buffer (50 mM Tris-HCl, 10 mM $MgCl_2$, 10 mM dithiothreitol, 25 μg/ml bovine serum albumin, and 26 μM NAD+, and pH 7.8); EGTA (ethylene glycol-bis(β-aminoethyl ether) N,N,N',N'-tetraacetic acid); EDTA (ethylenediaminetetracetic acid); ELISA (enzyme linked immunosorbant assay); LB (Luria-Bertani broth: 10 g tryptone, 5 g yeast extract, and 10 g NaCl per liter, pH adjusted to 7.5 with 1N NaOH); superbroth (12 g tryptone, 24 g yeast extract, 5 g glycerol, 3.8 g $KH_2PO_4$ and 12.5 g, $K_2HPO_4$ per liter); DMEM (Dulbecco's modified Eagle's medium); ABI (Applied Biosystems Inc., Foster City, Calif.); Amersham (Amersham Corporation, Arlington Heights, Ill.); ATCC (American Type Culture Collection, Rockville, N.Y.); Beckman (Beckman Instruments Inc., Fullerton Calif.); BM (Boehringer Mannheim Biochemicals, Indianapolis, Ind.); Bio-101 (Bio-101, Vista, Calif.); BioRad (BioRad, Richmond, Calif.); Brinkmann (Brinkmann Instruments Inc. Wesbury, N.Y.); BRL, Gibco BRL and Life Technologies (Bethesda Research Laboratories, Life Technologies Inc., Gaithersburg, Md.); CRI (Collaborative Research Inc. Bedford, Mass.); Eastman Kodak (Eastman Kodak Co., Rochester, N.Y.); Eppendorf (Eppendorf, Eppendorf Noah America, Inc., Madison, Wis.); Falcon (Becton Dickenson Labware, Lincoln Park, N.J.); IBI (International Biotechnologies, Inc., New Haven, Conn.); ICN (ICN Biomedicals, Inc., Costa Mesa, Calif.); Invitrogen (Invitrogen, San Diego, Calif.); New Brunswick (New Brunswick Scientific Co. Inc., Edison, N.J.); NEB (New England BioLabs Inc., Beverly, Mass.); NEN (Du Pont NEN Products, Boston, Mass.); Nichols Institute Diagnostics (Nichols Institute Diagnostics, San Juan Capistrano, Calif.); Pharmacia (Pharmacia LKB Gaithersburg, Md.); Promega (Promega Corporation, Madison, Wis.); Stratagene (Stratagene Cloning Systems, La Jolla, Calif.); UVP (UVP, Inc., San Gabreil, Calif.); USB (United States Biochemical Corp., Cleveland, Ohio); and Whatman (Whatman Lab. Products Inc, Clifton, N.J.). Unless otherwise indicated, all restriction enzymes were obtained from New England Biolabs and used according to the manufacturers directions. Unless otherwise indicated, synthetic oligonucleotides were synthesized using an ABI DNA synthesizer, Model No. 391.

EXAMPLE 1

The Wild Type MuMLV LTR Promoter is a Relatively Weak Promoter in Human Cells Most of the currently approved gene therapy protocols utilize the amphotropic M-MuLV vector, pLNL6. Accumulated experience with this vector has led to the realization that the activity of the M-MuLV LTR is weak compared to other enhancer/promoters or LTRs. In addition, the activity of this LTR in different cell types was found to be unpredictable. In order to design an improved retroviral vector, the relative strengths of several promoters were examined.

In this example, the M-MuLV LTR, CMV-IE and the activated HIV-1 LTR promoters were tested for their activities using a CAT reporter gene assay. Plasmids containing each of these three promoters directing the CAT gene were transfected into the human HeLa cell line (ATCC CCL 2). CAT activity was measured in order to determine the relative strength of these three promoters. CAT activity is expressed as the percentage of chloramphenicol converted to acetylated forms of chloramphenicol.

Plasmid DNA containing M-MuLV LTR directing the expression of the CAT gene (M-MuLV LTR-cat) was constructed by ligating the vector, pSP72-3'LTR digested with Asp718 (BM), to a DNA fragment containing the cat-SV40 polyadenylation site. To achieve this, the 3' LTR from pLNSX was isolated by ClaI and NdeI digestion (corresponds to nucleotides 3049 to 4082 in pLNL6). This fragment was inserted into pSP72 (Promega) digested with ClaI and NdeI thereby generating a subclone containing only one M-MuLV LTR (pSP72-3'LTR). The cat-SV40 DNA fragment was prepared by digesting pU3-R-CAT [Chang, L.-J. et al., (1993) J. Virol. 76:743] with HindIII and BamHI. The ends of the molecule were then filled in using T4 polymerase (NEB). An Asp718 linker [5'-GCTAGCGGT ACC-3' (SEQ ID NO:9)] was ligated to the blunt ends using T4 DNA ligase (IBI) according to the manufacture's protocols.

The plasmid pCMV-cat contains the CMV-IE promoter directing the expression of the CAT gene [Hunninghake, G. W. et al. (1989) J. Virol. 63:3026]. The plasmid pU3-R-CAT [Chang, L.-J. et al., J. Virol. 76:743 (1993)] contains the HIV-1 LTR directing the expression of the CAT gene.

Plasmid DNA was purified using an alkaline-SDS, cesium chloride gradient protocol [Sambrook, J. et al. (1989) Molecular Cloning: A Laboratory Manual, Vol. 2, pp. 1.21–1.52]. Briefly, bacteria [typically DH5α cells (BRL)] containing the desired plasmid were grown in 150 ml of superbroth in 250 ml flasks overnight in a 37° C. environment shaker (New Brunswick). The bacteria were pelleted by spinning at 5,000 rpm for 10 min using a JA10 or JA14 rotor (Beckman). The pellet was resuspend in 5 ml of lysis buffer [50 mM glucose or 15% sucrose W/V, 25 mM Tris (pH 8.0), 10 mM EDTA with 5 mg/ml lysozyme at 4° C.] and then incubated on ice for 10 to 20 min. To this mixture, 10 ml of freshly made 0.2N NaOH, 1% SDS (in ddH$_2$O) was added and mixed immediately by swirling and rotating the bottle. The bottle was then incubated at room temperature for 5 min. Then, 7.5 ml of cold 7.5M NH$_4$OAc (pH 7.5) was added and mixed by swirling the bottle. The mixture was incubated on ice for 5 min. The lysate was then centrifuged in a Beckman JA10 rotor at 8000 rpm for 10 min. The supernatant was transferred into a 50 ml polypropylene tube containing 25 μl of RNase A (10 mg/ml), mixed and incubated at 37° C. water bath for 1 hr. The mixture was extracted with a half volume of ddH$_2$O-saturated phenol (approximately 10 ml) and a half volume of chloroform by shaking vigorously for 1–2 min. The aqueous and organic phases were then separated by centrifugation at 800×g for 5 min in a table top centrifuge (Beckman). The top layer was mixed with 0.6–1 volume of cold 2-propanol and incubated at −20° C. for at least 30 min.

The plasmid DNA was pelleted by centrifugation at 10,000 rpm in a JA20 rotor (Beckman) for 20 min. The pellet was then dried in a vacuum. The pellet was resuspended in 1.5 ml of TE (10 mM Tris, pH 8.0, 1 mM EDTA), then mixed with 3 ml of CsCl solution (1.2 g/ml, ref. index 1.4155, prepared with autoclaved ddH$_2$O and filtered through a 0.45μ filter) and transferred into a Beckman VTi 65 tube. One hundred microliters of EtBr stock (5 mg/ml) was then added. The tube was filled to the sub-neck level with CsCl:ddH$_2$O (2:1). The weight of the tube was approximately 9.5 grams. The tube was sealed and centrifuged in a Beckman VTi 80 rotor at 60,000 rpm for at least 4 hr at 19° C.

The plasmid DNA (the lower band in the gradient) was drawn off using a 21 gauge needle attached to a 1 ml syringe. The plasmid band was extracted three times with 1 ml of 5M NaCl-saturated 2-propanol, and 4 ml of ddH$_2$O and 5 ml of cold iso-propanol were added. The plasmid DNA was precipitated at −20° C. overnight. The DNA was pelleted by centrifugation at 10,000 rpm using a Beckman JS13 rotor for 30 min. The pellet was rinsed with 70% ethanol carefully and dried under vacuum. The DNA was resuspended in 400 μl of ddH$_2$O. The DNA concentration was determined by measuring the absorption at 260 nm in a spectrophotometer.

The concentration of the plasmid DNA was also confirmed by running an aliquot on a 1% agarose gel followed by staining with 0.05 mg/ml of EtBr.

Plasmids containing the M-MuLV LTR, the HIV-1 LTR, and the CMV-IE enhancer/promoter were used to transfect HeLa cells in 6-well plates (Falcon) using a modification of the original Ca$_3$(PO$_4$)2-DNA coprecipitation procedure (Graham, F. L. and van der Eb, A. J., Virol., 52:456 [1973]). Briefly, approximately 4×10$^5$ HeLa cells were plated onto 6 well plates 20 hours prior to the addition of the DNA precipitate. The HeLa cells were at approximately 80–90% confluency when the DNA was added. HeLa cells were grown in DMEM (BRL) containing 10% FBS (BRL) and penicillin and streptomycin (BRL) and were fed with 2 ml of fresh DMEM containing 10% FBS and antibiotics 1 hour before addition of the DNA precipitate.

The DNA precipitates were made by mixing 90 μl of ddH$_2$O containing 2 μg of the desired CAT reporter plasmid [0.2 μg of pCEPtat (described in Example 2) was also added to the tube containing pU3-R-CAT in order to activate the HIV-1 promoter], 10 μl of 2.5M CaCl$_2$, and 100 μl of 2× BES buffer (50 mM N,N-bis[2-hydroxyethyl]-2-aminoethanesulfonic acid, 280 mM NaCl, 1.5 mM Na$_2$HPO$_4$, pH 6.95). Each well contained 2 ml of media and 200 μl of the DNA precipitates and was incubated in an atmosphere containing 5% CO$_2$ overnight at 37° C. The next day, the cells were washed once with growth medium (DMEM with 10% FBS) and fed with 2 ml of fresh media. Cell lysates were prepared 48 hr after changing the medium and CAT enzyme assays were performed.

Each transfection included 0.1 μg of the pXGH5 plasmid (Nichols Institute Diagnostics) which allows the transfected cells to express human growth hormone into the culture supernatant. Quantitation of the human growth hormone was performed using the commercially available ELISA kit provided by Nichols Institute Diagnostics. This provided an internal control for transfection experiments.

CAT assays were performed as described [Chang, L.-J. et al., (1993) J. Virol. 76:743]. Briefly, the HeLa cells were harvested 60 hr after the addition of the DNA, washed three times in PBS and subjected to three cycles of freeze-thawing in a 37° C. water bath and a dry-ice ethanol bath. The protein concentration in the cell lysates was determined by using a DC protein assay kit (BioRad). To obtain results within the linear kinetic range of CAT activity, the amount of cell lysate used in each reaction was adjusted to give a detectable signal within 1 hr and less than 60% consumption of the input substrate [$^{14}$C]chloramphenicol (0.5 μCi; 55 mCi/mmol; ICN). The enzyme concentration was determined by a serial dilution for lysates with high levels of CAT activity.

Following the incubation of the cell lysate and the substrate, the reaction products were spotted onto a TLC plate and chromatographed in a solution containing 95% chloroform and 5% methanol for 45 min. The plates were allowed to dry and then were autoradiographed by exposing the plates to photographic film for 12 hr at room temperature. The amount of chloramphenicol present in acetylated or non-acetylated forms was quantitated by exposing the TLC plates to an imaging plate for 2 hr and scanning with a phosphoimager (Model BAS 1000, Fuji Medical Systems, USA Inc.).

Figure 2:
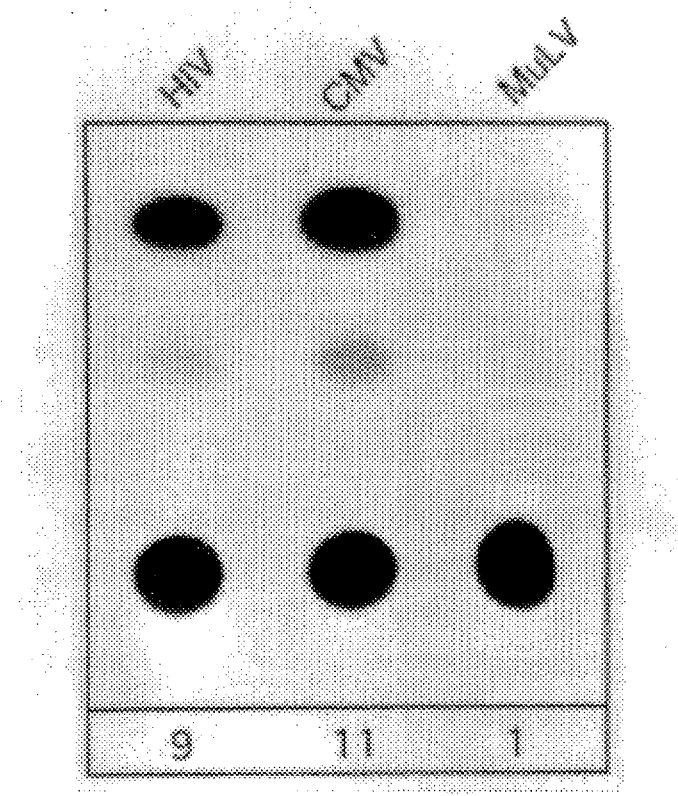
FIG. 2 shows an autoradiograph of a chloramphenicol acetyltransferase (CAT) assay showing the relative promoter strengths of HIV, CMV-IE and MLV in HeLa cells.

FIG. 2 shows the conversion of chloramphenicol to acetylated forms of chloramphenicol by the CAT enzyme produced by plasmids containing the HIV, CME-IE and MLV promoters. The amount of CAT enzyme present in the transiently transfected HeLa cells is a function of the strength of the enhancer/promoter which drives the expression of the CAT gene. FIG. 2 shows that the M-MuLV LTR is 9 times less active than the HIV LTR and 11 times less active than the CMV-IE enhancer promoter in HeLa cells. Clearly the M-MuLV LTR is not the optimal control signal when the target cell is of human origin (as will be the case for all gene therapy applications).

EXAMPLE 2

The Use of Internal Promoters in Retroviral Vectors is Disadvantageous

The results shown in FIG. 2 indicate that the M-MuLV LTR is not a strong promoter in human cells. In an attempt to achieve higher levels of expression of genes carried on a M-MuLV vector internal promoters have been utilized. The internal promoter is placed downstream of the viral LTR and is used to drive the expression of the inserted gene(s). However, as shown below, the activity of the internal promoter is often significantly reduced due to interference from the upstream M-MuLV promoter.

The strength of an internal promoter was compared with several heterologous promoters using a Tat trans-activation assay. HeLa cells were transfected with a series of plasmids which contains the tat gene driven by a given enhancer/promoter as shown schematically at the bottom of FIG. 8. In these constructs, the tat gene is driven by either no promoter (pSP72tat), the SV40 promoter (pSV-tat), the M-MuLV LTR driving the gpt gene followed by an internal SV40 promoter driving the tat gene (pLLLgptSVtat), the CMV-IE promoter (pCEP-tat) or the RSV LTR (pREP-tat). All cells are co-transfected with a second plasmid containing the HIV LTR (pU3-R-cat) driving the CAT gene. The HIV LTR is induced or trans-activated by the Tat protein. Thus the strength of the various promoters can be measured by determining the amount of CAT enzyme produce by the activated HIV LTR.

Figure 3:
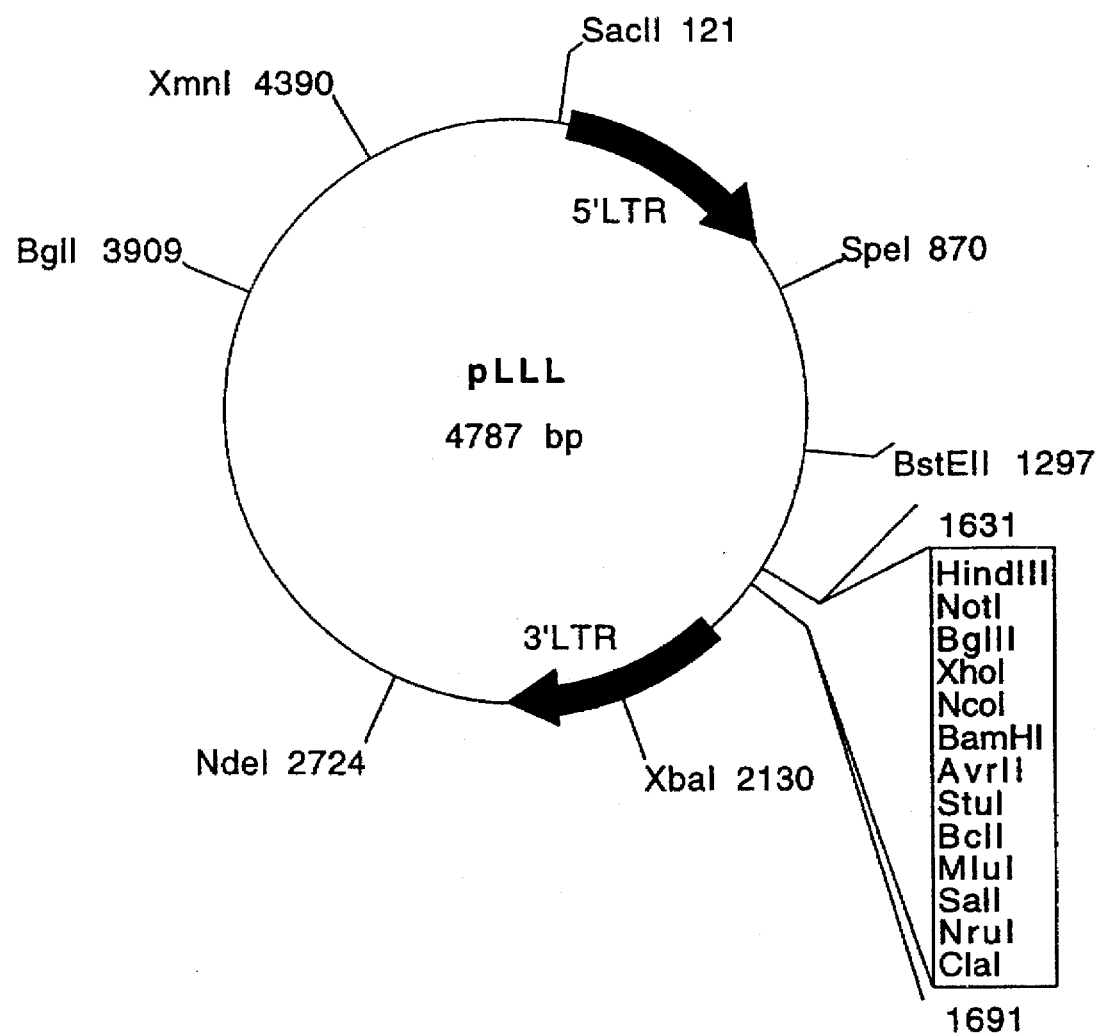
FIG. 3 shows the map of the retroviral vector pLLL. Selected restriction enzyme sites are indicated.
Figure 4:
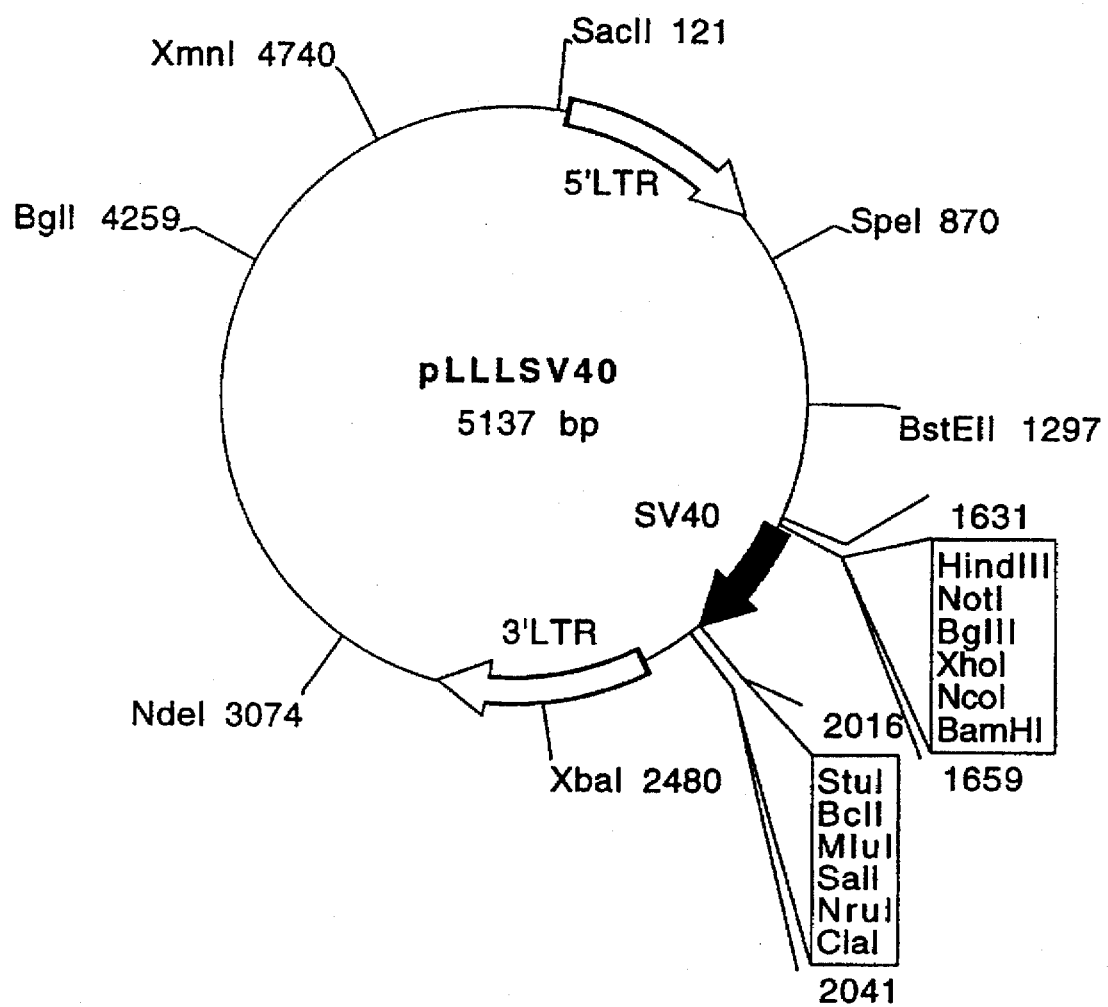
FIG. 4 shows the map of the retroviral vector pLLLSV40. Selected restriction enzyme sites are indicated.

The no promoter control plasmid (pSP72tat) was made by cloning the tat gene into pSP72 (Promega). The tat gene was isolated using PCR from the plasmid pSV-tat [Peterlin, B. M. et al. Proc. Natl. Acad. Sci. USA 83:9734 (1986)]. The primers used to amplify the tat gene were 5'-AAGGATCCTCGAGCCACCATGGAGCCAGT AGATCCT-3' (SEQ ID NO:12) and 5'-CAAGATCTGCATGCTAATCGAACGGATC TGTC-3' (SEQ ID NO:13). Reaction conditions were as described [Chang, L.-J. et al. (1993) J. Virol. 67:743]. Briefly, Pfu polymerase (Stratagene) was used according to the manufacturer's instructions in a 50 µl reaction containing 0.5 µg of each primer, 0.01 µg of pSVtat [Peterlin, B. M. et al. (1986) Proc. Natl. Acad. Sci. USA 83:9734] for 30 cycles under the following conditions: step 1: 94° C. for 5 min; step 2: 50° C. for 1 min; step 3: 72° C. for 1 min; step 4: 92° C. for 1 min and step 5: repeat steps 2–4 for 30 cycles. The tat gene was recovered from the PCR products by digestion with BamHI and BglII and inserted into pSP72 (Promega) digested with BamHI and BglII to generate pSP72tat.

pCEP-tat (contains the CMV-IE promoter driving the tat gene) and pREP-tat (contains the RSV LTR driving the tat gene) were constructed as follows. pSP72tat was digested with XhoI and BamHI to isolate the tat gene. This XhoI/BamHI fragment was then inserted into either the eucaryotic expression vector pCEP4 or pREP4 (Invitrogen) to generate pCEP-tat and pREP-tat, respectively. Pfu polymerase (Stratagene) was used in place of Taq DNA polymerase in the PCR because of its lower error rate. PCR conditions were as described above.

pLLLgptSVtat (the M-MuLV/SV40 construct) was made as follows. pLLL was constructed by digestion of pLNL6 with ClaI and BclII. The digested vector was purified and a double stranded insert containing a polylinker site was inserted. This double stranded insert was made by annealing the following two oligonucleotides together. 5'GATCTAAGCTTGCGGCCGCAGATCTC-GAGCCATGGATCCTAGGCC TGATCACGCGTCGACTCGCGAT-3' (SEQ ID NO:2) and 5'-CGATCGCGAGTCGA CGCGTGATCAGGCCTAGGATCCATGGCTCGAGATC-TGCGGCCGCAAGCTTA-3' (SEQ ID NO:3). After annealing the above oligonucleotides, the resulting DNA fragment contains restriction sites for HindIII, NotI, BglII, XhoI, NcoI, BamHI, AvrII, StuI, BclI, MluI, SalI, NruI and ClaI. The digestion of pLNL6 followed by the insertion of the annealed oligonucleotides resulted in the deletion of the sequences located between nucleotides 1625 (BclI site) and 3049 (ClaI site) in pLNL6. pLLL is shown schematically in FIG. 3.

pLLLSV40 was then constructed by inserting a fragment containing the SV40 promoter (isolated by digesting pLNSX with BamHI and StuI) into pLLL digested with BamHI and StuI. This generated pLLLSV40 (shown schematically in FIG. 4).

Figure 5:
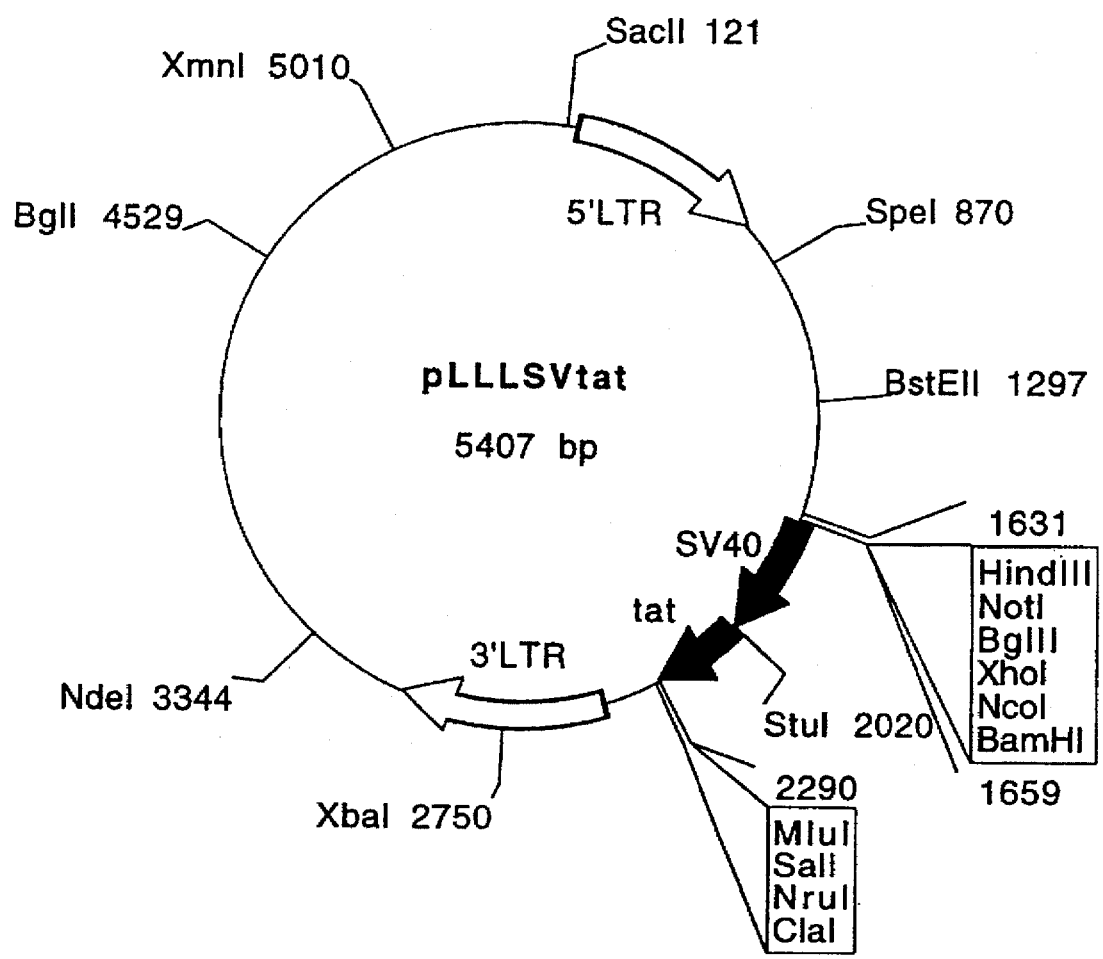
FIG. 5 shows the map of the retroviral vector pLLLSVtat. Selected restriction enzyme sites are indicated.

The tat gene was amplified as described above, digested with BamHI and BglII, and cloned into the BclI site of pLLLSV40 to generate pLLLSVtat (pLLLSVtat is shown schematically in FIG. 5).

Figure 6:
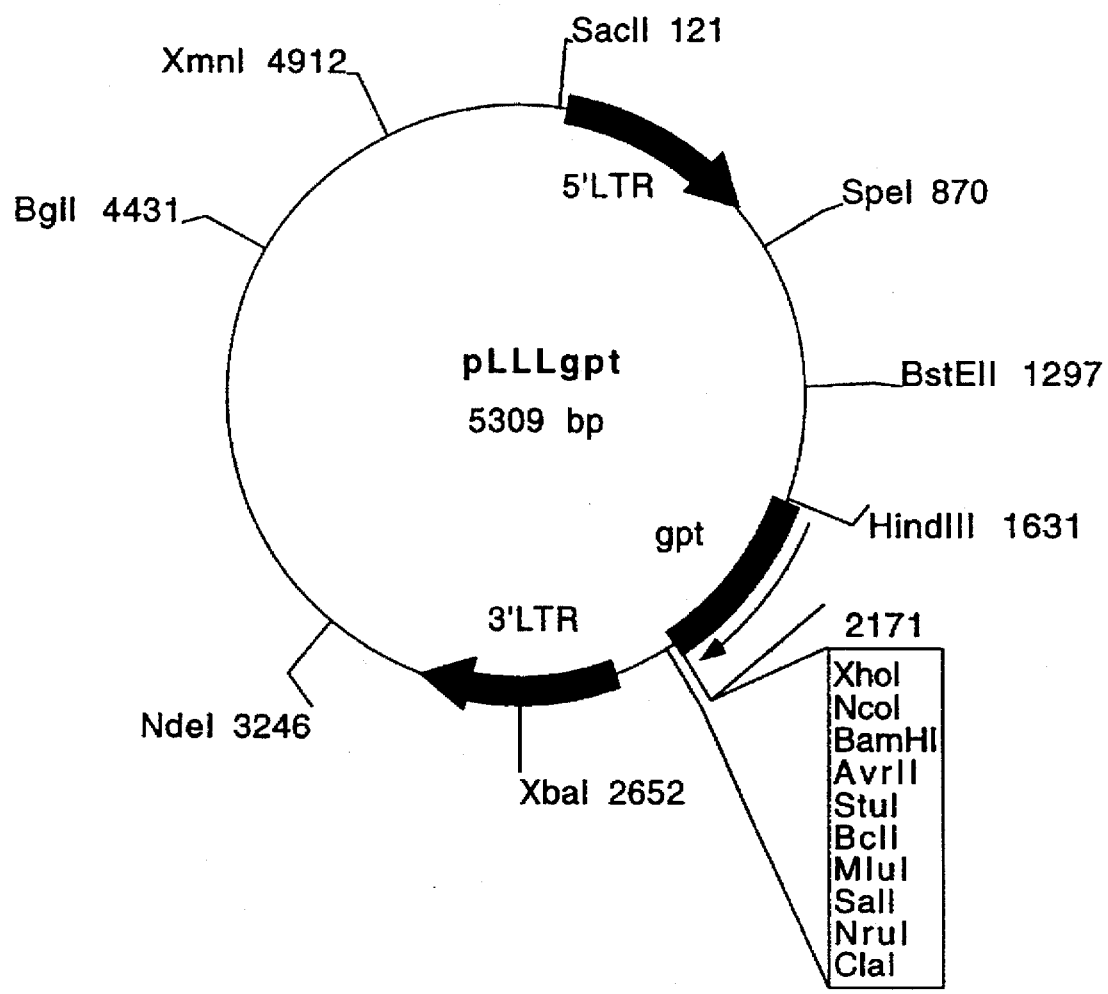
FIG. 6 shows the map of the retroviral vector pLLLgpt. Selected restriction enzyme sites are indicated.
Figure 7:
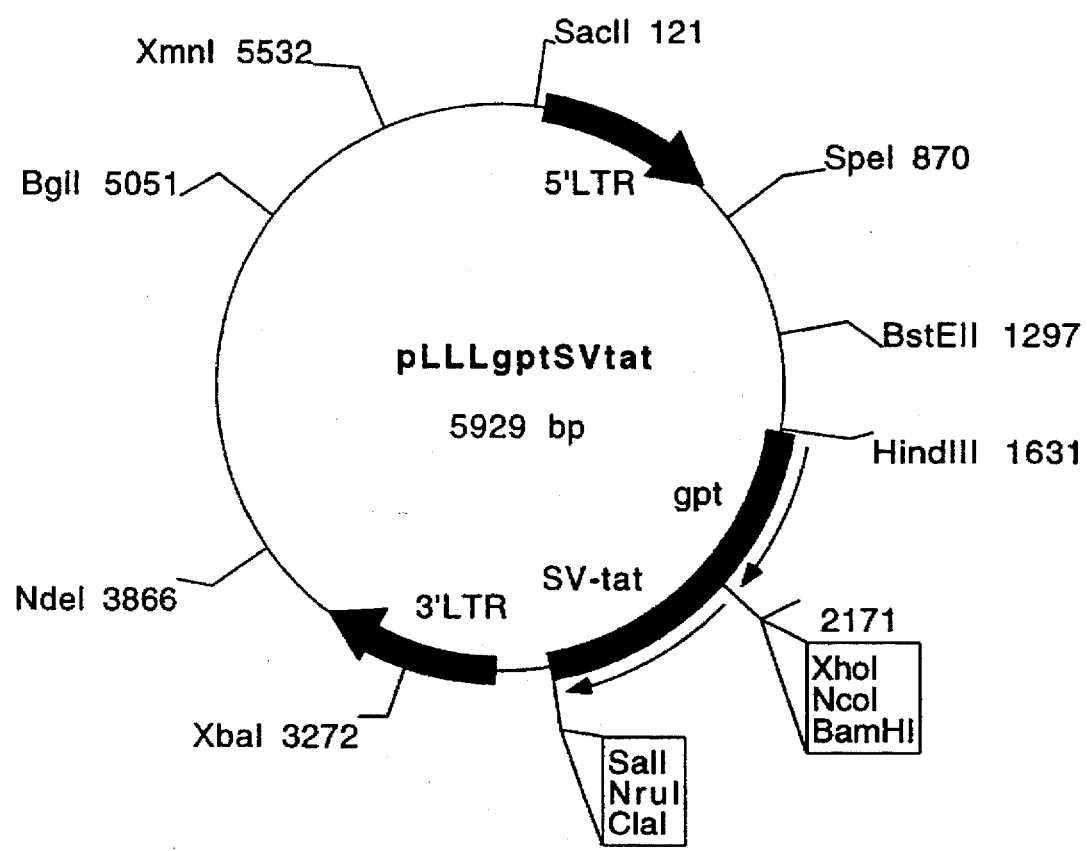
FIG. 7 shows the map of the retroviral vector pLLLgptS-Vtat. Selected restriction enzyme sites are indicated.

The gpt gene was amplified by PCR from pMSG (Pharmacia) using primers comprising sequences 5'-ATCTAGAAGCTTAGTGCGCCAGATCTCTATAATC-3' (SEQ ID NO:14) and 5'-ATCTAGACTCGAGTTAGCGACCGGAGATTGGC-3' (SEQ ID NO:15). The PCR products were digested with HindIII and XhoI and cloned into pSP72 (Promega) digested with HindIII and XhoI to generate pSP72gpt.

pLLLgpt (shown schematically in FIG. 6) was generated by cloning the gpt from pSP72gpt (HindIII to XhoI) into HindIII and XhoI digested pLLL. Then, the SVtat fragment was isolated from pLLLSVtat by digestion with BamHI and SalI; this fragment was inserted into pLLLgpt digested with BamHI and SalI to generate pLLLgptSVtat (pLLLgptSVtat is shown schematically in FIG. 7).

Figure 8:
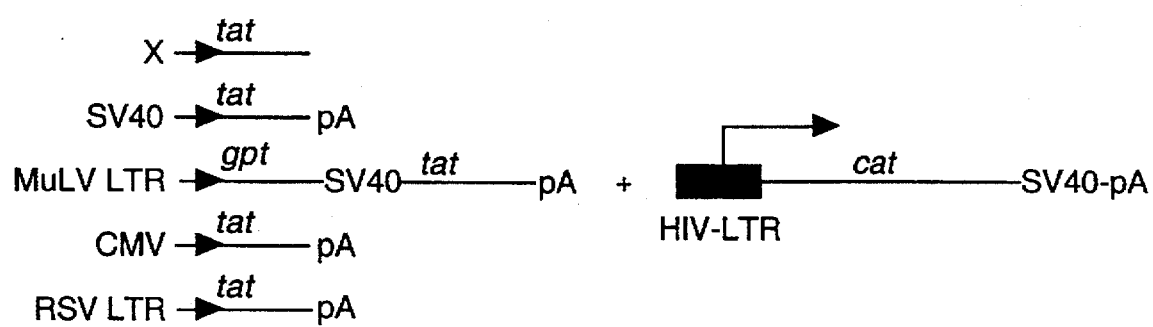
FIG. 8 is a simple schematic of the organization of the plasmids used in the experiment depicted in FIG. 9.

HeLa cells were transfected with 0.1 µg of a heterologous promoter plasmid driving the tat gene and 2 µg of the pU3-R-cat plasmid which contains the HIV LTR driving the CAT gene (the reporter gene). Plasmid purification, transfections and CAT assays were performed as described in Example 1. FIG. 8 is a simple schematic of the organization of the plasmids used in this Example. The following abbreviations are used in FIG. 8: X, pSP72tat (the no promoter control plasmid); SV40, pSVtat; M-MuLV/SV40, pLLLgptSVtat; CMV, pCEP-tat and RSV, pREP-tat.

Figure 9:
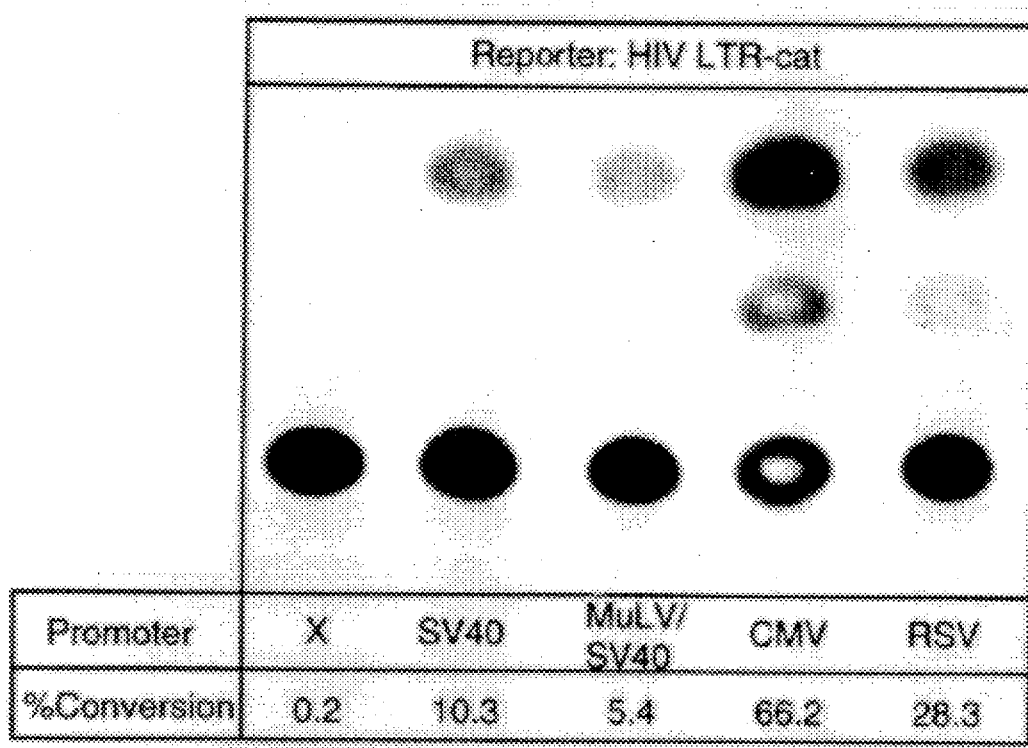
FIG. 9 shows an autoradiograph of a CAT assay depicting promoter activities in the presence of Tat. Percent conversion is shown.

FIG. 9 depicts the results of CAT assays performed on extracts made from HeLa cells transfected with either pSP72tat, pSVtat, pLLLgptSVtat, pCEP-tat or pREP-tat. As shown by the percentage conversion data in FIG. 9, the presence of the M-MuLV LTR upstream of the SV40 enhancer/promoter reduced the activity of the SV40 promoter approximately two-fold (compare lanes 2 and 3; 10.3% conversion of chloramphenicol when only the SV40 promoter is present on the tat plasmid compared to 5.4% conversion when the M-MuLV LTR is present upstream of the SV40 promoter). FIG. 9 also shows that the SV40 promoter is 6–13 fold less active than the CMV promoter in human cells (compare lanes 2,3 and 4). The RSV LTR (lane 5) was about 50% as strong as the CMV promoter in HeLa cells.

The results shown in FIGS. 2 and 9 indicate that the promoter activity of the M-MuLV LTR is not comparable in strength to an activated HIV-1 LTR or to the CMV-IE promoter. Furthermore, these results demonstrate that the use of an internal promoter in the M-MuLV vector is disadvantageous, as the activity of the downstream promoter is reduced. Therefore an improved LTR was designed to overcome the inherent limitations of the M-MuLV LTR without the use of an internal promoter.

EXAMPLE 3

Reconstruction of the M-MuLV LTR to Increase Promoter Activity

The HIV-1 LTR contains a very strong promoter which is active in almost all human cell types when the viral trans-activator Tat is present. The genetic element in HIV which mediates Tat activation is termed TAR (Tat-activation response). The TAR element is located in the U5 region of the HIV LTR. The TAR RNA physically binds to the viral trans-activator Tat to mediate the trans-activation function of Tat [Vaishnav, Y. N. and Wong-Staal, F. (1991) Ann. Rev. Biochem. 60:577].

A series of heterologous enhancer/promoter hybrids in the HIV-1 LTR in connection with TAR were previously constructed [Chang, L.-J. et al., (1993) J. Virol. 67:743]. These studies revealed that the combination of the CMV-IE enhancer/promoter and the HIV-1 TAR element creates a hybrid promoter which exhibits high basal activity (i.e., the activity of the hybrid promoter in the absence of Tat is higher than that of the wild type HIV-1 LTR) and which is inducible by Tat to higher levels (i.e., the hybrid promoter is activated or induced by Tat). These results showed that the activity of the HIV-1 LTR could be increased by substituting the CMV-IE enhancer/promoter for a portion of the HIV-1 LTR (the portion containing the NF-kB and Sp1 binding sites) while maintaining Tat responsiveness.

In order to create a novel LTR which is much stronger than the endogenous M-MuLV LTR and is responsive to Tat, the M-MuLV LTR was modified to include a truncated CMV-IE enhancer element and the HIV-1 TAR element (This recombinant M-MuLV LTR is present in the pMCT-cat construct described below).

Figure 10:
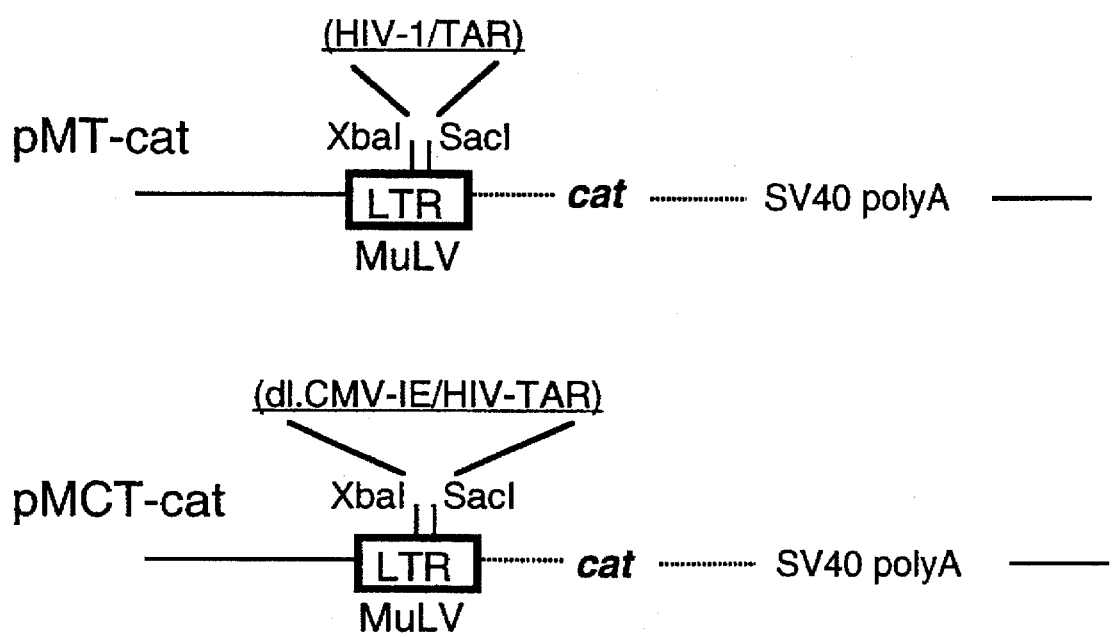
FIG. 10 is a schematic showing the pMT-cat and pMCT-cat constructs.

To reconstruct the MuLV LTR, a reporter plasmid, pSP72-3'LTRcat, was generated. pSP72-3'LTRcat contains the 3' LTR from the pLNL6 vector [Miller, A. D. and Buttimore, C. Mol. Cell. Biol. 6:2895 (1986); Bender, M. A. et al., J. Virol. 61:1639 (1987) and Miller, A. D. and Rosman, G. J. BioTechniques 7:980 (1989)], the CAT gene and a SV40 polyadenylation site. pSP72-3'LTRcat was constructed as follows. The 3' LTR from pLLL was isolated by ClaI and NdeI digestion (corresponds to nucleotides 3049–4086 in pLNL6). The 3' LTR fragment was then cloned into pSP72 (Promega) digested with ClaI and NdeI to generate pSP72-3'LTR. pSP72-3'LTR contains only one M-MuLV LTR.

pSP72-3'LTRcat was then further modified to create pMT-cat and pMCT-cat. The LTR present in pMT-cat replaces the CAAT box upstream of the M-MuLV TATA box with the HIV-1 TATA/TAR. The LTR present in pMCT-cat replaces the CAAT box upstream of the M-MuLV TATA box with the CMV-IE enhancer plus the HIV-1 TATA/TAR. These constructs are depicted schematically in FIG. 10.

To generate pMT-cat and pMCT-cat, fragments containing the HIV-1 TAR and a CMV-TAR DNA fragment were inserted into pSP72-3'LTR as follows. First, the SacI site near the M-MuLV LTR TATA box (corresponds to nucleotide 3604 in the pLNL6 numbering system) was changed to a EcoRI site by annealing an EcoRI adapter (5'-GAATTCAGCT-3') to the SacI ends. The HIV-1 TAR fragment (approx. 200 bp) was isolated from pU3-R-CAT using the PCR and the following primer pair: 5'-GCATCTAGAGTACTTCAAGAACTGC-3' (SEQ ID NO:6) (this primer corresponds to sequences near the HIV-1 TATA box and provides an XbaI site) and 5'-GGGAATTCGAGGCTTAAGCAGTGGGTTCC-3' (SEQ ID NO:7) (corresponds to sequences 3' of the HIV-1 TAR and provides an EcoRI site).

The CMV-TAR fragment (approx. 343 bp) was isolated from dl.kB/Sp1 CMV-IEaU3-R-CAT using the PCR and a primer pair consisting of: 5'-CCGGAGTAGCTA GCTGGAGTTCCGC-3' (SEQ ID NO:8) (corresponds to sequences located 5' to the CMV-IEa element and provides a NheI site) and SEQ ID NO:7 (listed above; i.e., the same primer used to generate the TAR fragment). The two amplified fragments were digested with XbaI (for the TAR construct) or NheI (for CMV-TAR) and EcoRI and cloned into the modified pSP72-3'LTR (contains an EcoRI site in place of the SacI site) digested with XbaI and EcoRI.

The identities of the two final products, pMT and pMCT, were confirmed by restriction enzyme digestion and DNA sequencing. To make the CAT reporter constructs, an approximately 1631 bp fragment containing the cat-SV40 polyA sequences was isolated by digestion of pU3-R-CAT with HindIII and BamHI. The cat-SV40 polyA fragment was gel-purified and the ends were made blunt using T4 polymerase. An Asp2718 linker [5'-GCTAGCGGTACC-3' (SEQ ID NO:9)] was ligated to the blunt ends and the fragment was cloned into Asp718 digested pSP72-3'LTR, pMT or pMCT to generate pSP72-3'LTRcat, pMT-cat and pMCT-cat, respectively.

The entire sequence of the recombinant M-MuLV LTR present in pMT-cat is: 5'-AATG- AAAGACCCCACCTG-TAGGTTTGGCAAGCTAGCTTAAGTAACGCCATT TTGCAAGGCATGGAAAAATACATAACT-GAGAATAGAGAAGTTCAGATCAAG GTCAGGAA-CAGATGGAACAGCTGAATATGGGCCAAA-C A G G A T A T C T G T G G T A AGCAGTTCCTGCCCCGGCTCAGGGCCAA-GAACAGATGGAACAGCTGAATATG GGCCAAACAG-GATATCTGTGGTAAGCAGTTCCTGC-C C C G G C T C A G G G C C A A G AACAGATGGTCCCCAGATGCGGTCCAGC-CCTCAGCAGTTTCTAGAGTACTTCA AGAACTGCT-GACATCGAGCTTGCTACAAGGGACTTTC-C G C T G G G G A C T T T C C AGGGAGGCGTGGCCTGGGCGGGACTGGG-GAGTGGCGAGCCCTCAGATGCTG CATATAAG-C A G C T G C T T T T T G C C T G - TACTGGGTCTCTCTGGTTAGACCAGATC TGAGCCTGGGAGCTCTCTGGCTAAC-TAGGGAACCCACTGCTTAAGCCTCGAA TTCAGCT-C A A T A A A A G A G C C C A C A A C C C C T - C A C T C G G G G C G C C A G T C C T C C G ATTGACTGAGTCGCCCGGGTACCCGTG-TATCCAATAAACCCTCTTGCAGTTGC ATCCGACT-T G T G G T C T C G C T G T T C C T T G G - GAGGGTCTCCTCTGAGTGATTGAC TACCCGTCAGCGGGGGTCTTTCATT-3' (SEQ ID NO:16).

The entire sequence of the recombinant M-MuLV LTR present in pMCT-cat is: 5'-AATGAAA- GACCCCACCTG- TAGGTTTGGCAAGCTAGCTTAAGTAACGCCATT
TTGCAAGGCATGGAAAAATACATAACT-
GAGAATAGAGAAGTTCAGATCAAG GTCAGGAA-
CAGATGGAACAGCTGAATATGGGCCAAA-
C A G G A T A T C T G T G G T A
AGCAGTTCCTGCCCCGGCTCAGGGCCAA-
GAACAGATGGAACAGCTGAATATG GGCCAAACAG-
GATATCTGTGGTAAGCAGTTCCTGC-
C C C G G C T C A G G G C C A A G
AACAGATGGTCCCCAGATGCGGTCCAGC-
CCTCAGCAGTTTCTAGCTGGAGTTC CGCGTTACAT-
AACTTACGGTAAATGGCCCGCCTGGCT-
G A C C G C C C A A C G A C C
CCCGCCCATTGACGTCAATAATGACG-
TATGTTCCCATAGTAACGCCAATAGG GACTTTCCAT-
TGACGTCAATGGGAGTTTGTTTTGGCAC-
C A A A A T C A A C G G G A C
TTTCCAAAATGTCGTAATAACCCCGC-
CCCGTTGACGCAAATGGGCGGTAGGC GTG-
TACTCTAGATGCTACATATAAGCAGCT-
GCTTTTTGCCTGTACTGGGTCTC
TCTGGTTAGACCAGATCTGAGCCTGG-
GAGCTCTCTGGCTAACTAGGGAACCC ACTGCT-
TAAGCCTCGAATTCAGCTCAATAAAA-
GAGCCCACAACCCCTCACTC
GGGGCGCCAGTCCTCCGATTGACT-
GAGTCGCCCGGGTACCCGTGTATCCAAT AAAC-
CCTCTTGCAGTTGCATCCGACTTGTG-
GTCTCGCTGTTCCTTGGGAGGGT
CTCCTCTGAGTGATTGACTACCCGTCAGCGGGGGT-
CTTTCATT-3' (SEQ ID NO:17).

The promoter activities of pMT-cat and pMCT-cat were compared with a wild type M-MuLV LTR, the HIV-1 LTR and the CMV-IE promoter in the presence or absence of HIV-1 Tat in DNA transfection experiments as described below.

EXAMPLE 4

The Modified M-MuLV LTR Promoter Functions Efficiently in A Wide Variety of Human Cell Types and is Trans-Activated by Tat Promoter activities of the modified M-MuLV LTRs in the presence or absence of the HIV-1 Tat protein were tested by transfecting a series of CAT reporter constructs into a panel of human cell lines.

A. Expression of the pMCT and pMT Promoters in a Panel of Human Cell Lines

The promoter activities of the modified M-MuLV LTRs (pMT-cat and pMCT-cat constructs) were compared with the wild type M-MuLV LTR, the HIV-1 LTR and the CMV-IE promoter in a variety of human cell lines. The ability of the promoters to be trans-activated by the Tat protein was also examined.

The following cell lines were used. HeLa, a human epithelioid carcinoma (ATCC CCL 2); HepG2, a human hepatoma line (ATCC HB 8065); HuH-7, a human hepatoma cell line [Nakabayashi, H. et al. (1982) Cancer Res. 42:3858]; CCRF-CEM (CEM), a human lymphoblastic cell line (ATCC CCL 119); and H9, a human T-cell lymphoma (ATCC HTB 176).

The following plasmids were used. pMLV LTR-cat (wild type M-MuLV LTR), pMT-cat (modified M-MuLV LTR containing the TAR element), pMCT-cat (modified M-MuLV LTR containing the CMV-IE promoter and the TAR element), pHIV LTR-cat (wild type HIV LTR) and pCMV-cat (CMV-IE promoter). The Tat expressing plasmid, pCEPtat, was co-transfected with each reporter plasmid to examine the ability of the Tat protein to trans-activate a given promoter. The ratio of reporter plasmid DNA to Tat plasmid DNA was 10:1. Plasmid DNA was prepared as described in Example 1.

Plasmid DNA was introduced by electroporation into the suspension lines, CEM and H9, and by calcium phosphate precipitation into the monolayer cell lines, HeLa, HepG2 and HuH-7.

Electroporations were performed as follows. Prior to electroporation, the CEM and H9 cells were grown in RMPI 1640 medium (Gibco-BRL) containing 10% fetal bovine serum (FBS, Gibco-BRL) and penicillin and streptomycin in an atmosphere containing 5% $CO_2$ at 37° C. Approximately $10 \times 10^6$ cells (0.4 ml) were placed in a 0.4 cm cuvette (BioRad), and plasmid DNA containing the desired CAT reporter gene (10 µg) was added. When the Tat protein was to be expressed 10 µg of reporter plasmid and 1 µg of Tat plasmid were used in the electroporation. The cells were then electroporated using a Gene Pulser (BioRad) at 960 µF and 300 V (with a time constant of 7.5–11 msec). The cells were then transferred into a T25 flask (Falcon) containing 10 ml of RPMI-1640 medium containing 20% FBS.

Following a 48 hr incubation, the cells were centrifuged at 600 X g for 5 minutes and then washed once in cold phosphate buffered saline. The cell pellet was resuspended in 100 µl Tris (25 mM, pH 7.8), and then freeze-thawed three times using a 37° C. water bath and a dry-ice bath. The cell pellet was vortexed after each thaw. The lysate was recovered by centrifugation at full speed (approximately 14,000 rpm) in a microcentrifuge (Brinkmann, Model 5415C) for 2 minutes.

The HeLa, HepG2 and HuH-7 cell lines were transfected using the calcium phosphate precipitation method described in Example 1. The transfected cells were harvested 48 hours after the addition of DNA. Cell lysates were prepared as described in Example 1.

Cell lysates were assayed for CAT activity as follows. Approximately 20 µl of the lysate was mixed with 75 µl Tris (1M, pH 7.8), 5 p,1 acetyl coenzyme A (3.5 mg/ml) and 3 µl of $^{14}C$-chloramphenicol. This reaction mixture was incubated at 37° C. for 45 minutes, then vortexed with 1 ml ethyl acetate. The top layer was transferred to a 1.5 ml microcentrifuge tube (Eppendorf) and dried under vacuum for 1 hour. The dried product was resuspended in 30 µl ethyl acetate, spotted onto a TLC plate (Whatman) and developed with 95% chloroform and 5% methanol in a closed glass tank. The developed TLC plate was analyzed by autoradiography or using a phosphoimager as described in Example 1.

The efficiency of the transfections was controlled for by co-transfecting an internal control plasmid (human growth hormone). Levels of CAT activity were normalized to this internal control. Each transfection included 0.1 µg of pXGH5 plasmid (Nichols Institute Diagnostics) which expresses human growth hormone into the culture supernatant. Quantitation of the human growth hormone was done using the ELISA kit provided by Nichols Institute Diagnostics.

Table 1 summarizes the results of these transfection experiments. The relative level of CAT expression is shown for each construct in the absence (–Tat) or the presence of Tat (+Tat).

TABLE 1

Relative Levels Of CAT Expression (−Tat/+Tat)*

| Cells: | pMLV LTR-cat | pMT-cat | pMCT-cat | pHIV LTR-cat | pCMV-cat |
|---|---|---|---|---|---|
| HeLa | 3.3/4.0 | 3.5/2.2 | 9.0/36.3 | 1.0/34.7 | 45.2/19.9 |
| HepG2 | 0.6/0.5 | 0.2/0.2 | 5.4/11.5 | 1.0/10.7 | 12.1/14.2 |
| HuH-7 | 0.7/1.0 | 0.4/0.5 | 7/7/19.0 | 1.0/22.0 | 18.6/— |
| CEM | 24.0/28.0 | 2.9/10.0 | 2.2/35.0 | 1.0/30.0 | 52.8/48.1 |
| H9 | 13.0/— | 0.2/0.2 | 5.6/63.0 | 1.0/42.0 | 43.0/— |

*For each cell type, results are reported relative to the level of CAT activity generated by pHIV LTR-cat in the absence of Tat (this level is arbitrarily assigned the value of 1.0). The CAT activities represent reproducible mean values from at least three independent experiments and were normalized to the expression of a human growth hormone plasmid construct as described. b"—", undetermined.

As shown in Table 1, in the absence of Tat, the pMCT promoter (pMCT-cat) exhibited activities 2–5 fold lower than the CMV-IE promoter (pCMV-cat), but considerably higher than the wild type M-MuLV LTR (pMLV LTR-cat). However in the presence of Tat, the pMCT-cat construct generally exhibited equal or higher activity than did pCMV-cat. On the other hand, the pMT-cat construct exhibited poor activity which was similar to pMLV LTR-cat. Furthermore, pMT-cat was not responsive to Tat, despite the fact that it contains the HIV-1 TAR element. This experiment shows that the modified M-MuLV LTR present in pMCT is a strong promoter in both hepatoma cells and T lymphocytes, whereas the wild type M-MuLV LTR is moderately active only in lymphocytes. These results also demonstrate that the enhancer element of the CMV-IE gene is essential to permit Tat trans-activation (pMT lacks this CMV element and is not capable of responding to Tat).

B. Expression of the pMCT Promoter in a Human B Lymphoblastoid Cell Line

As shown above, promoter activity clearly varies depending upon the cell type. To characterize the pMT and pMCT promoters further, the activity of these promoters was examined in the human B-lymphoblastoid cell line AA2 [Chaffee, S. et al., J. Exp. Med. 168:605 (1988); AA2 cells are available from the AIDS Research and Reference Reagent Program, NIH, Bethseda, Md., catalog no. 135]. In these experiments, a cellular β-actin promoter construct [pβactin-cat; Ng, S.-Y. et al. (1985) Mol. Cell. Biol. 5:2720] as well as the CMV-IE promoter [pCMV-cat; Hunninghake, G. W. et al. (1989) J. Virol. 63:3026] were included for comparison. All promoters were assayed either in the presence or absence of Tat.

Plasmid DNA was introduced into AA2 cells by electroporation as described above with the exception that AA2 cells were grown in RMPI 1640 medium (Gibco-BRL) containing 10% fetal bovine serum (FBS, Gibco-BRL), 1X non-essential amino acids (Gibco-BRL) and 1 mM pyruvate (Gibco-BRL) and penicillin (50 units/ml; Gibco-BRL) and streptomycin (50 µg/ml; Gibco-BRL) in an atmosphere containing 5% $CO_2$ at 37° C. The AA2 cells were electroporated at 250 µF and 300 V (with a time constant of 7.5–11 msec). Cell lysates were prepared 48 hours after the addition of DNA. Cell lysates were prepared and assayed for CAT activity as described above.

Figure 11:
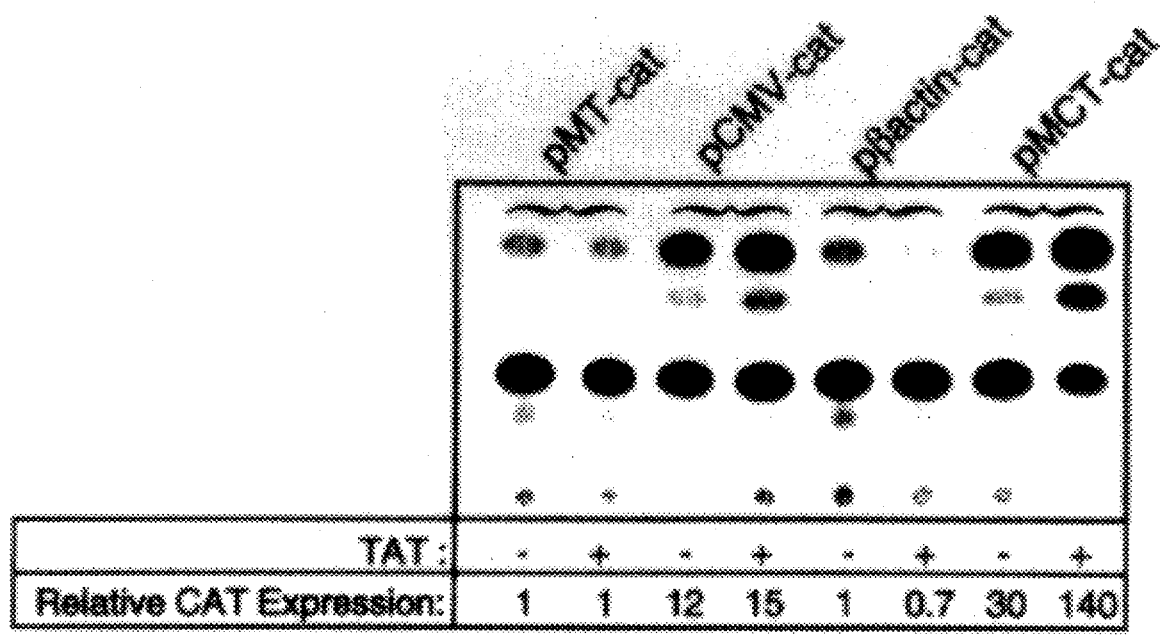
FIG. 11 shows an autoradiograph of a CAT assay depicting the basal and Tat-induced promoter activity in AA2 cells.

FIG. 11 shows the results of these transfection experiments. As shown in lane 7 of FIG. 11, the M-MuLV-CMV-TAR (pMCT) construct exhibited high promoter activity in the absence of Tat. As shown in lane 8 of FIG. 11, in the presence of Tat, the pMCT promoter was trans-activated significantly. Thus, in AA2 cells, the pMCT promoter gave the highest level of expression among the promoters examined, whether or not Tat was present. It is possible that the high levels of CAT expression induced by pMCT were due to the existence of a heterologous viral trans-activator in AA2 cells (the AA2 cell was established by EBV-transformation). The pMCT construct may have the added advantage that it expresses at higher levels in cells which are infected with or transformed by a number of different viruses (i.e., in addition to HIV).

In contrast, the M-MuLV-TAR (pMT) construct showed low basal activity and was not responsive to Tat (see lanes 1 and 2 of FIG. 11). In comparison to the strong CMV-IE promoter, the M-MuLV-CMV-TAR (pMCT) promoter exhibited 2-fold higher basal activity (i.e., in the absence of Tat). The M-MuLV-CMV-TAR (pMCT) promoter was responsive to Tat as shown by the 4–5 fold increase in activity (relative to the basal activity) seen in the presence of Tat.

These results indicate that the M-MuLV LTR and HIV TAR combination (present in pMT) is not sufficient to confer Tat-responsiveness upon the M-MuLV LTR. In contrast the CMV-TAR modification (present in pMCT-tat) allows for the transactivation of the pMCT promoter and further provides a hybrid promoter having a high basal level of activity in human cells.

C. Expression of the Modified M-MuLV LTR in a Human Cell Line Constitutively Expressing Tat Expression levels from pMCT-cat in the presence of Tat were further assessed using a human T lymphoma cell line, CEM-TART [Chen, H. et al. (1992) Proc. Natl. Acad. Sci. USA 89:7678; CEM-TART cells are available from the AIDS Research and Reference Reagent Program, NIH, Bethseda, Md.]. CEM-TART cells constitutively express the HIV-1 Tat protein. The following CAT reporter constructs were electroporated into CEM-TART cells: pCMV-cat, pLLL-cat (contains the wild type MuLV LTR), pMCT-cat and pHIV LTR cat.

CEM-TART cells were grown and electroporated as described above for CEM and H9 cells in Example 4A. Plasmid DNA was purified as described in Example 1. Cell lysates were prepared 48 hours after the addition of the DNA and CAT assays were performed as described above in Example 1.

Figure 12:
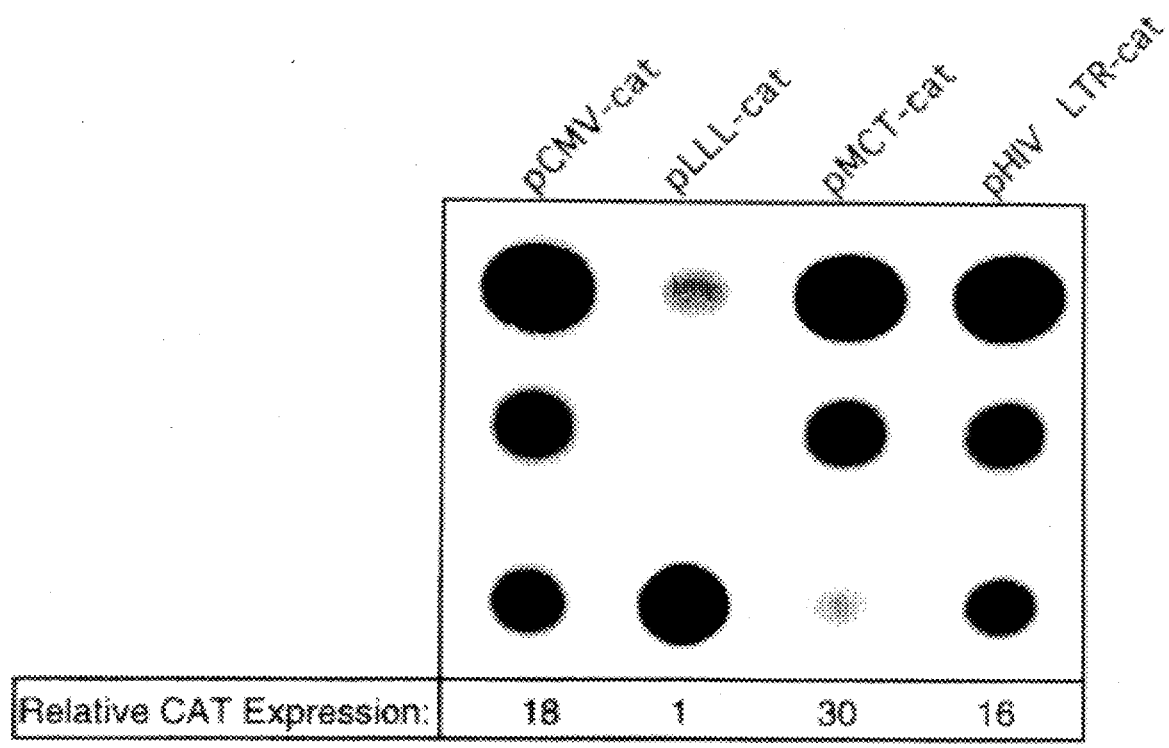
FIG. 12 shows an autoradiograph of a CAT assay depicting the relative levels of CAT expression in CEM-TART cells.

FIG. 12 shows the relative levels of CAT expression in CEM-TART cells. These results indicate that the pMCT promoter exhibited the highest activity among M-MuLV LTR, CMV-IE, and HIV-1 LTR promoters. Therefore, for the purpose of targeting HIV-1 infected cells, the pMCT construct appears to be ideal, since it exhibits high activity in the absence of Tat, and is strongly activated in the presence of Tat (i.e., during HIV-1 infection).

EXAMPLE 5

Transcription Initiates from Both TATA Boxes in the pMCT LTR Construct

The pMCT LTR construct contains both the M-MuLV TATA box and the HIV-1 TATA box. To determine whether transcription initiated from one or both of these TATA boxes the following experiments were performed. HepG2 cells were transfected with pMCT-cat plasmid and the RNA transcripts were analyzed by Northern blot analysis and RNase mapping.

HepG2 cells were transfected with plasmid DNA [10 µg/T25 flask (Falcon)] in the presence or absence of pCEPtat (2 µg/T25 flask) by the calcium phosphate method as described in Example 1 except that all reagents were scaled up 2.5 times. Cells were washed with cold PBS two times 24 hr after DNA removal and scraped into 1 ml of PBS in a 1.5 ml microcentrifuge tube. The cells were pelleted by centrifugation for 1 min at 3000 rpm. The cells were resuspended in 250 µl of Solution I (10 mM Tris, pH 7.4, 10 mM NaCl and 3 mM MgCl$_2$, RNase-free) containing 25 µl of VRC (BRL) and incubated on ice for 5 min. Twelve and one-half microliters of 10% NP40 was added and the tube was vortexed briefly and centrifuged in a microcentrifuge at 4000 rpm for 3 min. 250 µl of the supernatant was transferred into a second tube containing 250 µl of 2 X proteinase K buffer (200 mM Tris, pH 7.5, 40 mM EDTA and 300 mM NaCl), and 25 µl of 10% SDS, 10 µl of 5 mg/ml proteinase K were added. The solution was incubated at 37° C. for 30 min to 1 hr. To isolate the polyA$^+$ RNA, the solution was brought to 0.5M NaCl, 1% SDS and approximately 30 p.1 of oligo-dT cellulose powder (CRI) was added and the tube was rotated at room temperature for 1 hr. The oligo-dT cellulose was pelleted and washed twice with 650 µl of high-TEN-SDS (20 mM Tris, pH 7.5, 10 mM EDTA and 0.5M NaCl, 1% SDS) and once with 650 µl of low TEN-SDS (as above but using 0.1M NaCl instead of 0.5 M NaCl). The RNA was eluted with 200 µl TE (10 mM Tris, pH 7.5, 1 mM EDTA) twice and precipitated with 40 µl of 5M ammonium acetate and 1 ml of 95% ethanol.

For Northern blot analysis, polyA$^+$ RNA isolated from HepG2 cells transfected with pMCT-cat in the presence or absence of pCEPtat as described above. The RNA was electrophoresed on a 1.6% formaldehyde agarose gel. The RNA was transferred to a nylon membrane [Genescreen (DuPont)] and probed using the cat gene present in pMCT-cat. pMCT-cat was radiolabeled using the Prime-a-Gene labelling system (Promega). In order to control for the amount of RNA loaded in each lane, the blot was stripped of the cat probe and rehybridized with a β-actin probe [pβ-actin; Karlsson, R. et al. (1991) Mol. Cell. Biol. 11:213].

Figure 13:
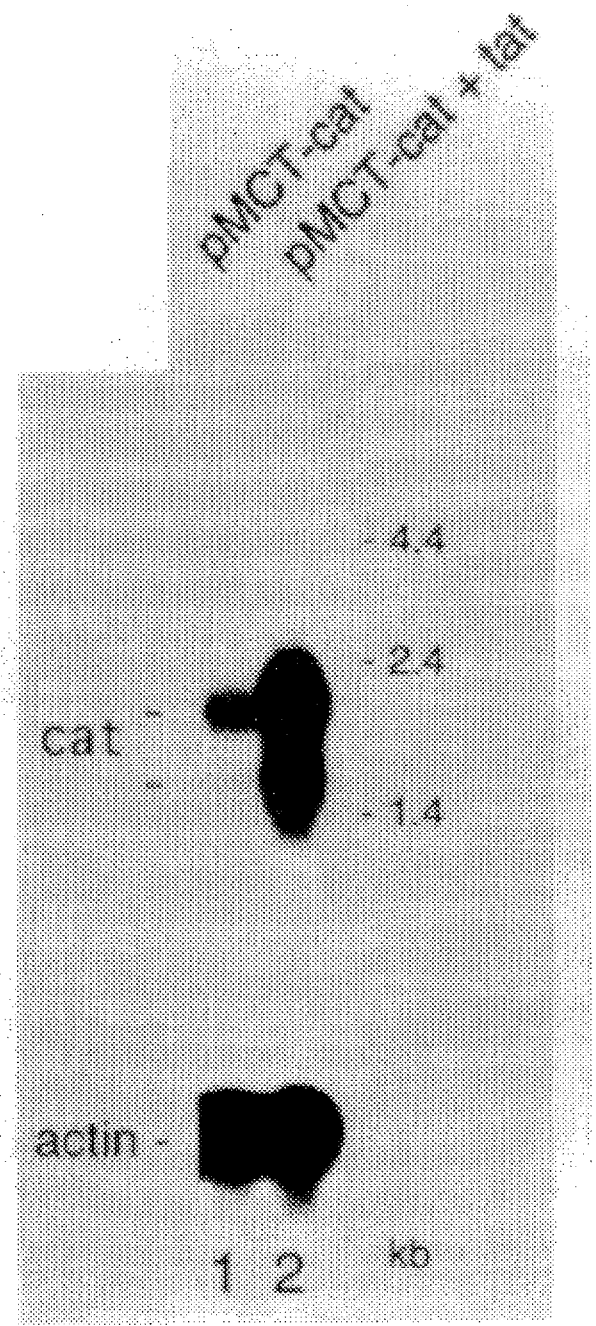
FIG. 13 shows an autoradiograph of a Northern blot depicting the results of a trans-activation initiation experiment.

FIG. 13 shows the autoradiograph of the Northern blot. The radioactivity on the membrane (i.e., the Northern blot) was quantitated using a phosphoimager (Fuji Bio-imaging analyzer BAS 2000). Comparison of lane 1 (pMCT-cat alone) with lane two (pMCT-cat plus pCEPtat) shows that Tat trans-activated synthesis of CAT RNA from the pMCT promoter up to 16 fold.

For RNase mapping, the probe was made using pU3CMV5'CAT. pU3CMV5'CAT was constructed by inserting the NheI to EcoRI fragment (approximately 930 bp) of pMCT-cat (Example 3) into pSP72 (Promega) digested with XbaI and NheI. pU3CMV5'CAT was digested with SalI and 0.5 µg of linear DNA was transcribed with phage T7 polymerase (Promega) using the according to the manufacturer's protocol. The reaction contained 4 µl of 5x in vitro transcription buffer (Promega), 2 µl of 0.1M DTT, 0.5 µl of RNasin (20 units), 1 µl each of 10 mM ATP, GTP and CTP, 2 µl of 100 µM UTP, 1 µl of linear DNA (0.5 µg), 5 µl (50 µCi) of α32P-UTP (DuPont NEN catalog #NEG-007H), 5.5 µl of ddH$_2$O and 1 µl of T7 polymerase (10 units) and incubated at 37° C. for 1 hr. The DNA template was digested with 1 µl of RNase-free DNase (1 unit/µl) at 37° C. for 10 min in the presence of 20 µg of yeast tRNA (in 2 µM). The labeled RNA was precipitated with 80 µl of TE, 20 µl of 5M ammonium acetate, and 360 µl of ethanol. After pelleting, the RNA was resuspended in 50 µl of formamide and stored at −20° C. until used.

RNase mapping was performed by mixing 25% of the polyA$^+$ RNA isolated from the transfected HepG2 cells with 2 µl of the RNA probe in 30 µl of 1 X hybridization buffer containing 80% formamide (5X hybridization buffer comprises: 2M NaCl, 5 mMEDTA and 0.2M MOPS, pH 7.0) at 90° C. for 5 min. The temperature was then decreased to 40° C. overnight. To the hybridization solution, 300 µl of RNase digestion buffer (10 mM Tris, pH 7.5, 5 mM EDTA, 0.3M NaCl, 40 µg/ml RNase A, 2 µg/ml RNase T1) was added and the tube was incubated at 30° C. for 1 hr. After RNase digestion, 10 µl of 20% SDS and 5 µl of proteinase K (10 mg/ml) were added and the tube was incubated at 37° C. for 15 min. The final product was extracted with phenol-chloroform followed by extraction with chloroform and precipitated with 20 µg of yeast tRNA carrier by adding 1 ml cold ethanol and incubation at 70° C. for at least 3 hr.

The RNA-RNA hybrids were resolved on a 5% neutral polyacrylamide gel. BstEII-digested lambda DNA (BRL) was run on the gel to provide a marker. The gel was dried and exposed to X-ray film and quantified using a phosphoimager (Fuji) as described in Example 1.

Figure 14:
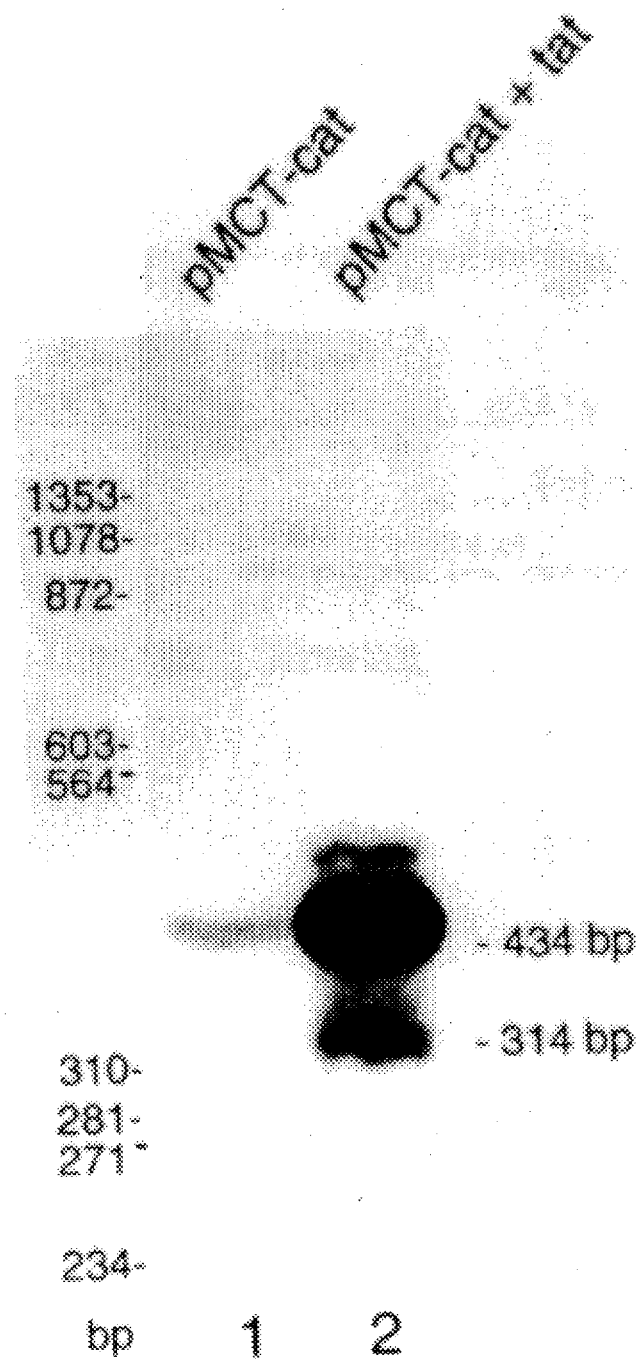
FIG. 14 shows an autoradiograph of a RNA protection assay depicting the results of a trans-activation initiation experiment.
Figure 15:
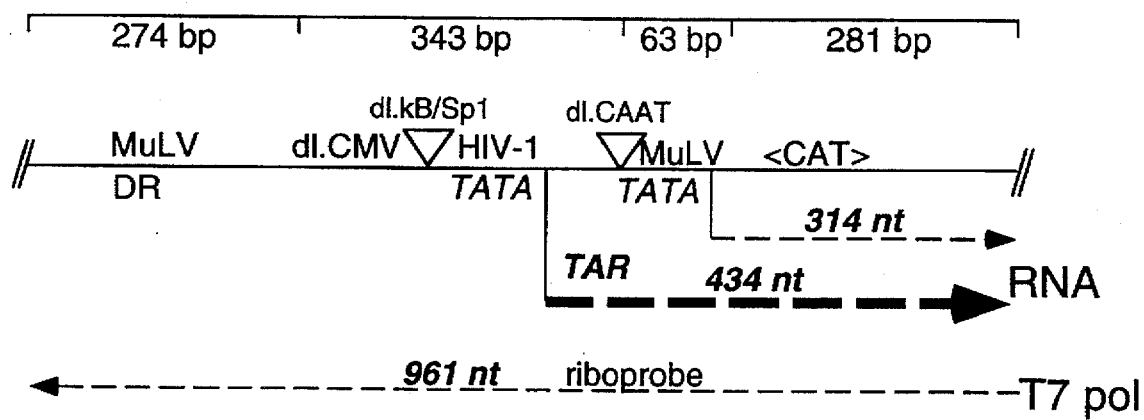
FIG. 15 schematically depicts the probe used in the experiment shown in FIG. 14.

FIG. 14 shows the results of the RNase mapping. FIG. 15 is a schematic showing the probe and the location of the TATA boxes in pMCT. If both transcription initiation sites are used two species of RNA will be protected generating bands of 434 and 314 nucleotides in length. The data show that both the HIV and the M-MuLV transcription initiation sites were used in HepG2 cells transfected with the pMCT-cat plasmid (FIG. 12B). The upstream HIV initiation site was preferred 8–10 fold over the downstream M-MuLV site (FIG. 12B). Tat up-regulated the synthesis of both species of RNA (17-fold from the HIV promoter and 22-fold from the M-MuLV promoter) suggesting that although TAR is not present on the M-MuLV transcript, the rate of transcription from the downstream M-MuLV transcription unit was still mediated by upstream Tat-TAR interaction.

The results shown in this Example demonstrate that the LTR present in pMCT is inducible by the Tat protein. The amount of RNA produced from the pMCT promoter increased 16 to 22 fold over basal levels when Tat was present (16 fold as judged by Northern blot analysis; 17 to 22-fold as judged by RNase mapping).

EXAMPLE 6

Generation of Improved Retroviral Vectors Containing Modified 3' LTRs With or Without Extended Packaging and Splicing Signals pMT and pMCT are single LTR plasmids. In order to generate a retroviral vector containing these improved promoters, the construct must contain both a 5' and a 3' LTR. Retroviral vectors containing these modified LTRs were constructed.

In order to increase the level of expression of genes inserted into retroviral vectors, the amphotropic M-MuLV vector, pLNL6, was modified. The pLNL6 vector was used as the starting point for the creation of improved retroviral vectors because pLNL6 has been approved for use in clinical therapy protocols.

Specifically, the M-MuLV LTR was reconstructed to produce a retroviral vector containing the CMV-IE enhancer and a HIV-1 trans-activation response (TAR) element (the pMCT promoter). This novel recombinant M-MuLV LTR contains MLV and CMV enhancer elements, two TATA promoters (from HIV and MLV) and the HIV-1 TAR element. These modifications were carefully designed so that important M-MuLV functions such as reverse transcription, packaging and polyadenylation of viral RNA would not be disrupted. The CMV-IE enhancer was chosen as it functions as a strong enhancer in a wide variety of cell types. The TAR element directs very high levels of expression in cells which are expressing the HIV-1 trans-activator Tat (i.e., HIV-1 infected cells). The TAR element also competes for the HIV-1 protein Tat which induces the production of HIV-1 in the infected cells. These features result in high levels of anti-HIV genes to be expressed and prevent the spread of the HIV virus in the body's immune system, both by limiting production of HIV from cells already infected, and by allowing the immune system to be gradually re-populated with immune cells which can no longer be infected. The combination of the CMV-IE enhancer and TAR increases the level of expression of inserted genes in HIV infected cells. Additionally, because the LTR of pLCTSN contains a very strong promoter, this vector is ideal for expression of inserted genes in a wide variety of mammalian cell types (including non-HIV infected cells). The ability to express a gene to high levels in mammalian cells will facilitate studies of gene expression, lineage mapping studies, etc.

This improved retroviral vector (pLCTSN) was further modified to include extended packaging and splicing signals from the M-MuLV genome (creating pLGCTSN). These modifications were designed to increase the efficiency of packaging the vector RNA into vital particles.

Figure 16:
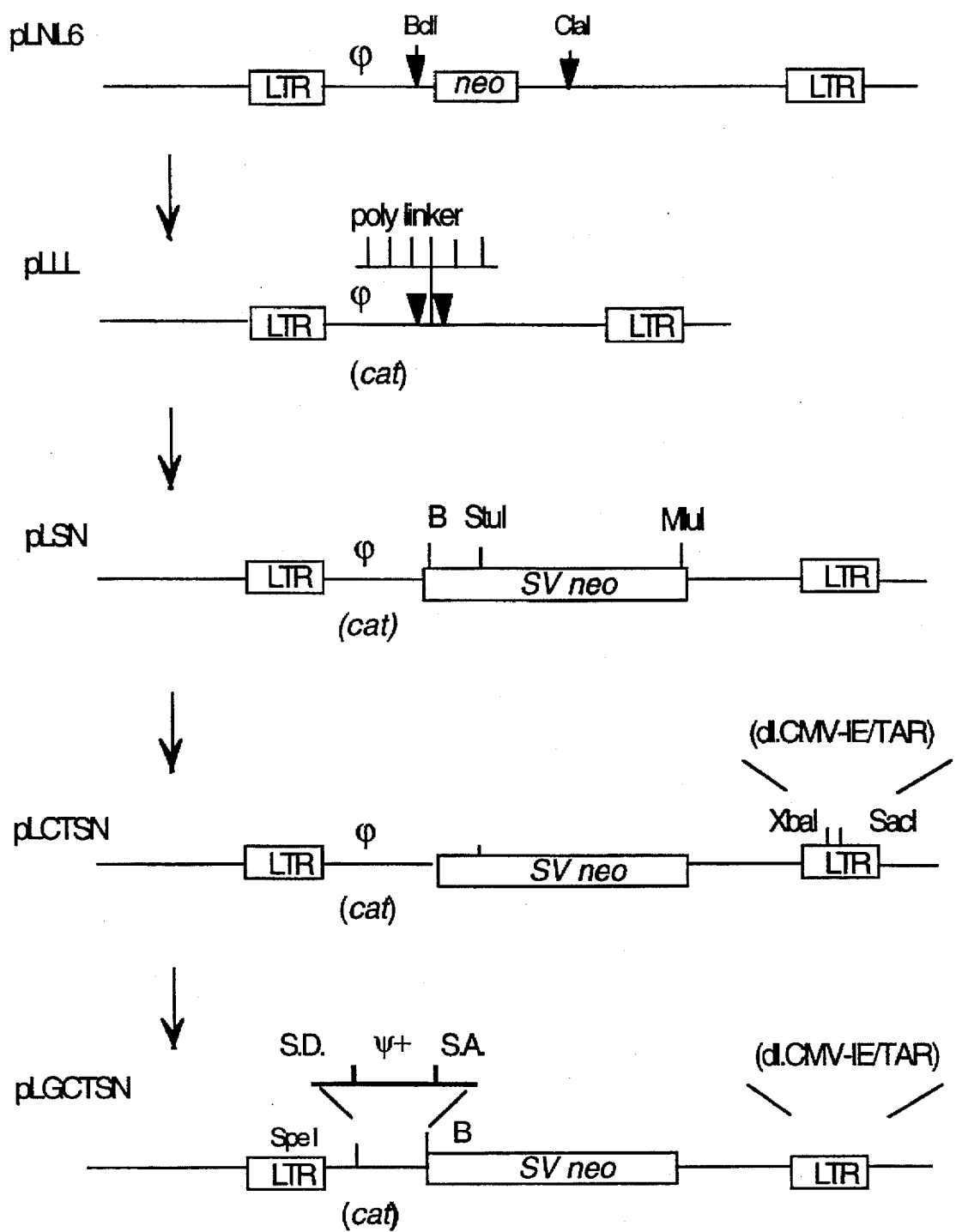
FIG. 16 is a schematic of the modifications made to produce the modified MuLV vectors.

FIG. 16 depicts schematically these modified MuMLV vectors. Modifications to generate vectors containing LTRs with improved promoter function were made only to the 3' (M-MuLV) LTR. These modifications will appear in both LTRs following infection, reverse transcription and integration of the vector sequences.

a) Construction of pLLL pLLL was constructed using pLNL6 (SEQ ID NO:1) as a starting point. pLNL6 contains the M-MuLV promoter in the 3' LTR and the murine sarcoma virus (MSV) promoter in the 5' LTR. For ease in subsequent cloning steps, the few cloning sites and the internal SV-neo gene present in pLNL6 were removed and replaced with a synthetic polylinker to generate pLLL (shown schematically in FIG. 16).

To construct pLLL, 1 µg of pLNL6 was digested with 5 units of ClaI in NEB buffer #4 (50 mM potassium acetate, 20 mM Tris-acetate, 10 mM magnesium acetate and 1 mM DTT at pH 7.9), in a final volume of 20 µl at 37° C. for 1 hour. Then, 5 units (0.5 µl) of BclI were added and the reaction temperature was increased to 50° C. for 1 hour. To isolate the vector fragment, the reaction mixture was mixed with 2 µl of glycerol-dye (10% glycerol, 1 mM EDTA, 0.1% xylene cyanol FF, and 0.1% bromphenol blue) and electrophoresed on a 1% agarose gel until the dye front had move two thirds down the length of the gel. The upper band was visualized with a hand-held UV box (UVP Model UVGL-25, 366 nm) and cut out with a razor blade. This agar block was transferred to a 1.5 ml microcentrifuge tube (Eppendorf) and the DNA was isolated using GeneClean (Bio-101) according to the manufacturer's instructions. The volume of the agar block containing the ClaI digested vector was measured. Sodium iodide solution was added to the tube containing the agar block at a volume 3–5 times that of the agar block. The agar was melted by incubation at 60° C. for 5–10 minutes. To this mixture, 1 µl of glass milk (glass milk was provided in the GeneClean kit from Bio-101) was added and the mixture was incubated at room temperature for 5 min. The tube was centrifuged briefly in a microcentrifuge (Brinkmann) at 14,000 rpm for 10 sec. The pellet was washed twice with 600 µl of GeneClean wash at –20° C. The DNA was then eluted twice using 10 µl of ddH$_2$O at 60° C.

The double stranded insert containing the polylinker site was constructed using the following two oligonucleotides: 5'-GATCTAAGCTTGCGGCCGCAGATCTCGA GCCATGGATCCTAGGCCTGATCACGCGTCGACTCG-CGAT-3' (SEQ ID NO:2) and 5'-CGATCGCGAGTCGACGCGTGATCAGGCCTAGGA-TCCATGGCTCGAGAT CTGCGGCCGCAAGCTTA-3' (SEQ ID NO:3).

These oligonucleotides were mixed together in 20 µl ddH$_2$O, heated at 85° C. for 5 minutes and gradually cooled down to room temperature over a 1 hour period. To this tube, 2.3 µl of 10X kinase buffer (700 mM Tris-HCl, 100 mM MgCl$_2$ and 50 mM DTT, pH 7.6), and 1 µl of T4 polynucleotide kinase (NEB) were added. The mixture was incubated at 37° C. for 1 hour. The kinase activity was then inactivated by incubating the mixture at 65° C. for 1 hour.

Ligation of the vector and the oligonucleotide insert was performed in 10 µl of a reaction mixture comprising 1X ligation buffer (50 mM Tris-HCl, 10 mM MgCl$_2$, 10 mM DTT, 25 µg/ml bovine serum albumin, and 26 µM NAD+, and pH 7.8), 0.05 µg of the pLNL6 vector, 0.01 µg of insert, and 0.5 unit of T4 DNA ligase (IBI) at 15° C. overnight. The ligation mixture was used to transform competent DH5α cells (BRL) as follows. Two µl of the ligation mixture was added to 20 µl of competent cells and incubated at 4° C. for 30 min. The cells were then subjected to a temperature shock by incubation at 40° C. for 1 min. and placed in a 37° C. shaker (250 rpm) for 1 hour before being plated onto an ampicillin agar plate (LB plus 1.5% agar and 0.1 mg/ml ampicillin) and incubated in a 37° C. incubator overnight. On the second day of incubation, colonies (usually 12) were picked from the ampicillin agar plate and placed in 3 ml superbroth with ampicillin (100 µg/ml). The tube was incubated overnight at 37° C. with shaking.

Plasmid DNA was prepared by the boiling method [Sambrook, J. et al. (1989) *Molecular Cloning: A Laboratory Manual*, Cold Spring Harbor Press, Cold Spring Harbor, N.Y., pp. 1.34–1.35]. Approximately 1.4 ml of the overnight culture was transferred into a 1.5 ml microcentrifuge tube (Eppendorf) and the bacteria were pelleted by centrifugation in a microcentrifuge for 2 min and the supernatant was removed. The pellet was resuspended completely in 50 µl STET buffer (8% sucrose, 0.5% Triton X-100, 50 mM EDTA and 50 mM Tris-HCl, pH 8.0) by vortexing. The bacteria were lysed by the addition of 4 µl of 5–50 mg/ml lysozyme solution (Sigma, frozen stock stored at –20° C.) and the tube was boiled for exactly 1 min in a boiling water bath. The lysate was centrifuged for 10 min in a microcentrifuge, and the scum pellet was discarded with a toothpick. To the supernatant an equal volume (50 µl) of cold isopropanol (–20° C.) was added, the tube was mixed and incubated at –20° C. for 10 min to precipitate plasmid DNA. The plasmid DNA was pelleted for 5–10 min in a microcentrifuge and the pellet was resuspended in 50 µl of ddH$_2$O. For restriction enzyme mapping, 10 µl of the DNA was digested with the appropriate restriction enzymes in a final reaction volume of 20 µl.

The plasmid DNA was then mapped by SstI, SstI/HindIII, and Asp718/BamHI digestion. The clone containing the sequence of interest was grown in a large preparation as described in Example 1.

The site of insertion was confirmed by DNA sequencing using the following primers 5'-GAACCTCCTCGTTCGACC-3' (SEQ ID NO:18), and 5'-AACTAGAGCC TGGACCAC-3' (SEQ ID NO:19). These primers contain sequences which correspond to sequences located 5' and 3' to the insertion. The sequencing reagents and methods used were those provided by USB in the Sequenase kit. Briefly, 5 µl of plasmid (containing about 4 μg DNA) was mixed with 1 μl of primer (10 ng), 1 μl of 1N NaOH and incubated at 37° C. for 10 min. To the mixture, 1 μl of 1N HCl and 2 μl of 5 X Reaction buffer (200 mM Tris-HCl pH 7.5, 100 mM MgCl$_2$, 250 mM NaCl) were added and incubated at 37° C. for 5 min. To the tube, the following reagents were added in order: 1 μl 0.1M DTT, 2 μl diluted labeling mix (diluted 5 to 1 dilution of 7.5 μM dGTP, 7.5 μM dCTP, and 7.5 μM dTTP), 0.5 μl $^{35}$S-dATP (Amersham), 2 μl diluted Sequenase (diluted 8 to 1 in enzyme dilution buffer: 20 mM Tris-HCl, pH 7.5, 2 mM DTT, 0.1 mM EDTA and 50% glycerol), and the reaction was incubated at room temperature for less than 5 min. To a 96-flex well plate (Falcon) marked with A, T, C, G, 2.5 μl of ddNTP termination mix (ddA: 80 μM dNTP, 8 μM ddATP, 50 mM NaCl; ddT: 80 μM dNTP, 8 μM ddTTP, 50 mM NaCl; ddC: 80 μM dNTP, 8 μM ddCTP, 50 mM NaCl; ddG: 80 μM dNTP, 8 μM ddGTP, 50 mM NaCl) was added to the designated well on the side of the wall and the plate was incubated at 37° C. for 1 min. To the bottom of the flex well plate, 3.5 μl of the Sequenase reaction mix was added, and the reaction was started by hiring the plate gently to mix all the reagents simultaneously. The reaction was incubated at 37° C. for 5 min. To stop the reaction, 4 μl of stop solution (95% formamide, 20 mM EDTA, 0.05% of bromphenol blue and 0.05% xylene cyanol FF) was added to each well, on the side, and hit to stop all reactions simultaneously. The 96-well was heated to 75° C. for 2 min before loading onto a sequencing gel. The gel was electrophoresed at 2000 volt for a period of time depending on the length of the readable sequences. The gel was transferred to a piece of 3MM paper (Whatman) and dried under vacuum. The sequence was determined by exposing the dried gel to a XAR5-OMAT film (Eastman Kodak Co.).

pLLL is shown schematically in FIG. 16. DH5α bacterial cells harboring pLLL were deposited with the American Type Culture Collection.

pLLL was then used to construct a series of two-LTR retroviral vectors: pLSN, pLCTSN and pLGCTSN, all of which contain a CAT reporter gene. The CAT gene was isolated from pCAT3M as a BglII/Sau3AI fragment; this fragment was cloned into the BamHI site located in the polylinker of the above plasmids. CAT gene sequences are available from a variety of commercial sources including pCAT-Control vector (Promega). pLSN, pLCTSN and pLGCTSN all contain a SV40 promoter driving the selectable marker neo (shown schematically in FIG. 16).

b) Construction of pLSN

To generate a vector containing a selectable marker which allows for the isolation of cells which have incorporated the vector DNA, pLSN was created. pLSN contains the neo gene under the transcriptional control of the SV40 enhancer/promoter; pLSN also contains the CAT reporter gene (shown schematically in FIG. 16). pLSN functions as the wild type vector control in subsequent transfection experiments.

To create pLSN, a BamHI/StuI fragment containing SV40 enhancer/promoter was isolated from pLNSX [Miller, A. D. and Rosman, G. J. (1989) BioTechniques 7:980]. pLNSX and pLLL were digested with BamHI and StuI in NEB buffer #2 (50 mM NaCl, 10 mM Tris-HCl, 10 mM MgCl$_2$, 1 mM DTT, pH 7.9). The digestion products were purified by agarose gel electrophoresis as described above for the construction of pLLL. A small fragment of approximately 350 bp which contained the SV40 promoter from pLNSX was cloned into the pLLL vector. The final product, designated pLLL/SV40, was confirmed by restriction enzyme digestion using BamHI and ClaI.

In order to insert a better translation initiation codon at the beginning of the neo gene, the neo gene was isolated from pLNSX using PCR. Pfu polymerase (Stratagene) was used to amplify the gene. This amplification was conducted in 5 μl of 10x Pfu reaction buffer, 0.5 μl of dNTP (15 mM), 0.5 mM of each of the following primers: 5'-AAGCTTGATCACCACCATGATTGAACAAGATGG-3' (SEQ ID NO:4) and 5'-CCGGATCC-GTCGACCCCAGAGTCCCGCTCAGAAG-3' (SEQ ID NO:5), 0.5 μl of pLNSX (0.01 μg) and 38 μl of ddH$_2$O. These primers contain the modified translation initiation control sequence (-CCACC<u>ATG</u>-), as this modification was found to greatly increase the strength of the neo gene in tissue culture cells [Kozak, M. (1986) Cell 44:283].

The mixture was heated at 95° C. for 5 minutes and 1 μl of Pfu polymerase was added. This reaction mixture was cycled through 30 cycles at 94° C. for 1 minute, 55° C. for 1 minute, and 72° C. for 3 minutes. After amplification, the DNA was precipitated with a 0.1 volume of 3M sodium acetate and 2 volumes of ethanol and then separated on a 1% agarose gel, as described above for the construction of pLLL. Purification of the DNA band from the agarose gel, ligation of the fragment with the BclI-digested pLLL/SV40 vector, screening, purification and confirming of plasmid pLSN was conducted as described above.

c) Construction of pLCTSN pLCTSN contains the modified M-MuLV LTR present in the pMCT construct. pLCTSN was generated by the following four-fragment ligation. The vector pLSN was digested with SacII and KpnI. The three inserts were SacII to XhoI of pLSN, XhoI to NheI of pLSN, and NheI to KpnI of pMCT. Isolation of DNA fragments, ligation, transformation of competent DH5α, screening of colonies, and mapping of the positive clones were performed as described above for the construction of pLSN.

pLCTSN is shown schematically in FIG. 16. DH5α bacterial cells harboring pLCTSN were deposited with the American Type Culture Collection.

d) Construction of pLGCTSN pLGCTSN contains the modified M-MuLV LTR present in the pMCT construct and contains extended packaging signals and a 3' splice acceptor site from the M-MuLV genome. The addition of these sequences were made to improve the packaging efficiency of the vector RNA and to avoid interference by the native 5' splice donor site. The 5' splice donor site does not have a corresponding splice acceptor in the pLCTSN vector. This modification stabilized transcripts expressed by the vector and enhanced the packaging efficiency of vector genomes.

pLGCTSN was cloned by inserting an SpeI-BamHI fragment of pDGLtax/rex [Akagi, T. et al. Gene 106:255 (1991)] into the same sites of pLCTSN. This SpeI/BamHI fragment contains the extended packaging signal and a 3' splice acceptor site from the HIV-1 genome. The positive clones were confirmed with SpeI, BamHI, KpnI and BglII digestions. pLGCTSN is shown schematically in FIG. 16.

DH5α bacterial cells harboring pLGCTSN were deposited with the American Type Culture Collections.

EXAMPLE 7

Packaging Efficiency of the Improved M-MuLV Vectors

In addition to providing more efficient promoters, increasing the vector titer of the packaging cells is yet another key issue in retroviral gene therapy and a goal of the invention. The modifications made to create the new retroviral vectors pLSN, pLCTSN or pLGCTSN were examined to determine the effect upon the packaging efficiency of vector sequences. The packaging cell line, PA317 [Miller, A. D. and Buttimore, C. (1986) Mol. Cell. Biol. 6:2895 and Miller, A. D. (1990) Hum. Gene Ther. 1:5], was transfected with pLSN, pLCTSN or pLGCTSN using lipofectamine (BRL). Lipofection was carried out according to the manufacturer's protocol.

PA317 cells were grown in DMEM containing 10% FBS and penicillin and streptomycin in an atmosphere containing 10% $CO_2$ at 37° C. Twenty hours prior to lipofection, PA317 cells were placed into a T25 flask (Falcon) at 50% confluency (approximately $1 \times 10^6$ cells/flask). To transfect the cells, DNA (4 µg) was added to 300 µl serum-free DMEM not containing antibiotics in a microcentrifuge tube (Eppendorf), and mixed gently. In a 15 ml polycarbonate tube (Falcon), 300 µl serum-free DMEM and 12 µl of lipofectamine were mixed gently. The two solutions were combined by adding the DNA-containing solution dropwise into the lipofectamine tube, and the mixture was incubated at RT for 45 min. Following this incubation, 2 ml of serum-free DMEM was added and mixed gently. The cells were washed with serum-free DMEM and the DNA/lipofectamine mixture was gently added to the cells. The cells were incubated at 37° C. in a 10% $CO_2$ incubator for 5 hr. After the 5 hr incubation, 2.5 ml of DMEM containing 20% FBS and antibiotics was added to the T25 flask and the cells were incubated overnight. Twenty hours after the 5 hr incubation, the medium was replaced with fresh DMEM containing 20% FBS and antibiotics. For vector titration, the medium was changed at 24 hr after the medium was replaced with fresh DMEM and virus was harvested 24 hr later. When cells were to be cloned, the transfected PA317 cells were split at a 1:10 ratio into the appropriate selective medium.

Packaging efficiency was determined by infecting HeLa and HuH-7 cells using the virus stocks generated from transfected or selected PA317 cells. Duplicate plates of PA317 cells were transiently transfected with equimolar amounts of the retroviral vector DNAs using the lipofection protocol above. Supernatants were harvested 24 hr after transfection and assayed for the presence of viral particles. The recombinant viruses were titered by retroviral transduction of HeLa and HuH-7 cells and quantitation of the resulting G418-resistant colonies.

Infections were carried out as follows. HeLa and HuH-7 cells were split into 6-well plates at a density of $5 \times 10^5$ cells per well 17–20 hr prior to infection. Cells were infected with virus stock (prepared as described above) at dilutions of 1:100, 1:1000 and 1:10,000 in 500 µl of growth medium (DMEM containing 10% FBS and antibiotics) containing 4 µg/ml polybrene (Sigma) for 2 hr. The plates were fed with 2 ml of growth media. Twenty-four hr after adding the growth medium, the cells were split at a ratio of 1:20 into selective medium [DMEM containing 10% FBS, penicillin, streptomycin and 5 mg/ml G418 (Geneticin™, BRL)]. G418-resistant colonies were counted about 8–10 days later by coomassie brilliant blue G staining (1 g/liter in 40% methanol and 10% acetic acid; Miller, A. D. et al. (1993) Methods in Enzymology 217:581). The results were calculated based on 2–3 sets of repeats.

Table 2 shows the results of the packaging assays performed by infection of HeLa and HuH-7 cells. The packaging efficiency is judged by the number of viral particles per ml of culture supernatant removed from the transfected PA317 packaging cells. Only those viral particles containing the vector sequences, and therefore the neo gene, give rise to G418-resistant HeLa or HuH-7 cells upon infection.

The LTR-modified vectors, pLCTSN and pLGCTSN, were packaged 3–10 times more efficiently than the parental pLNL6 or pLSN vectors (as judged by a comparison of the resulting titers; the titer is expressed as colony forming units (i.e., G418-resistant colonies) per milliliter of harvested supernatant). These results show that the modifications made to the M-MuLV LTR do not interfere with viral replication including RNA packaging, reverse transcription and integration. In fact, the modifications to the LTR results in the modified vectors being packaged more efficiently than the parental vectors which contain unmodified M-MuLV LTRs. Similar results were obtained using stably transformed PA317 cell lines established by selection in G418 rather than transiently transfected PA317 cells (Table 3). For the experiment depicted in Table 3, HeLa cells were transduced with supernatants obtained from PA317 cells stably transformed with the indicated vectors.

TABLE 2

Titration Of Retrovirus By G418 Selection With Transfected PA317 (HuH-7, 48 hr)

| Vector | pLNL6 | pLSN | pLCTSN | pLGCTSN |
|---|---|---|---|---|
| | Titer × $10^{6*}$ | | | |
| HeLa | 6.5, 0.3 | 3.8, 9.0 | 22.8, 15.3 | 35.5, 21.0 |
| HuH-7 | 2.5, 0.9, | 5.3, 0.8, | 9.0, 5.8, | 12.2, 13.8, |
| | 1.0, 3.6 | 7.3, 9.7 | 7.4, 9.7 | 12.7, 12.5 |

*The titer is expressed as G418-resistant colony forming units/ml times $10^6$. Thus, a value of 6.5 indicates that $6.5 \times 10^6$ G418-resistant colonies are produced per milliliter of harvested supernatant.

TABLE 3

Titration Of Retrovirus By G418 Selection With Infected PA317 (Producer)

| Vector | pLNL6 | pLSN | pLCTSN | pLGCTSN |
|---|---|---|---|---|
| | 8 Titer × $10^{4*}$ | | | |
| | 51.6, 134 | 1.2, 81.4 | 3.6, 5.0 | 88.8, 6.8 |

*The titer is expressed as G418-resistant colony forming units/ml times $10^4$. Thus, a value of 51.6 indicates that $51.6 \times 10^4$ G418-resistant colonies are produced per milliliter of harvested supernatant.

EXAMPLE 8

The pLCTSN Vector Directs Stable Expression of Inserted Genes

In order to assess the ability of the modified LTR to direct long-term expression of genes, the long term stability of the modified vector pLCTSN was studied in HeLa and HepG2 cells. HeLa and HepG2 cells were infected (i.e., transduced) with virus harvested from PA317 cells and selected with G418 as described in Example 7. Usually, cell colonies were pooled or single cell clones picked after two weeks of growth in selective medium. These pools or single clones were then grown in selective medium for a further 1–2 months.

After 1–2 months of growth, roughly equivalent numbers of G418-resistant cells (approximately $5 \times 10^6$ cells; typically originating from a series of different clones) were lysed and the relative CAT activity per unit protein was determined for each lysate as described in Example 1.

Figure 17:
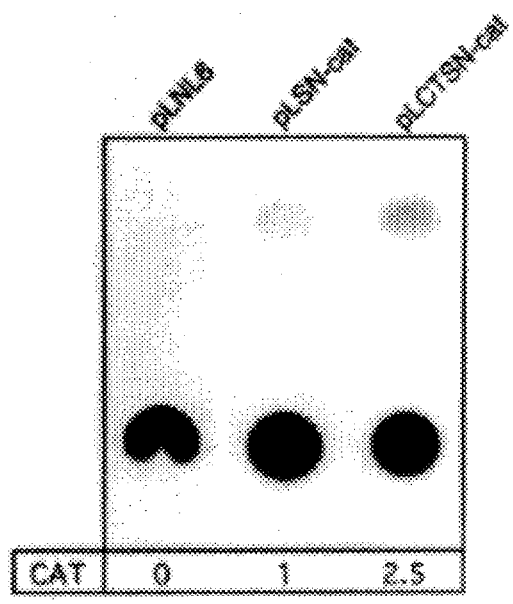
FIG. 17 shows an autoradiograph of a CAT assay depicting the long term expression of genes in the pLSN-cat and pLCTSN-cat constructs in HeLa cells.
Figure 18:
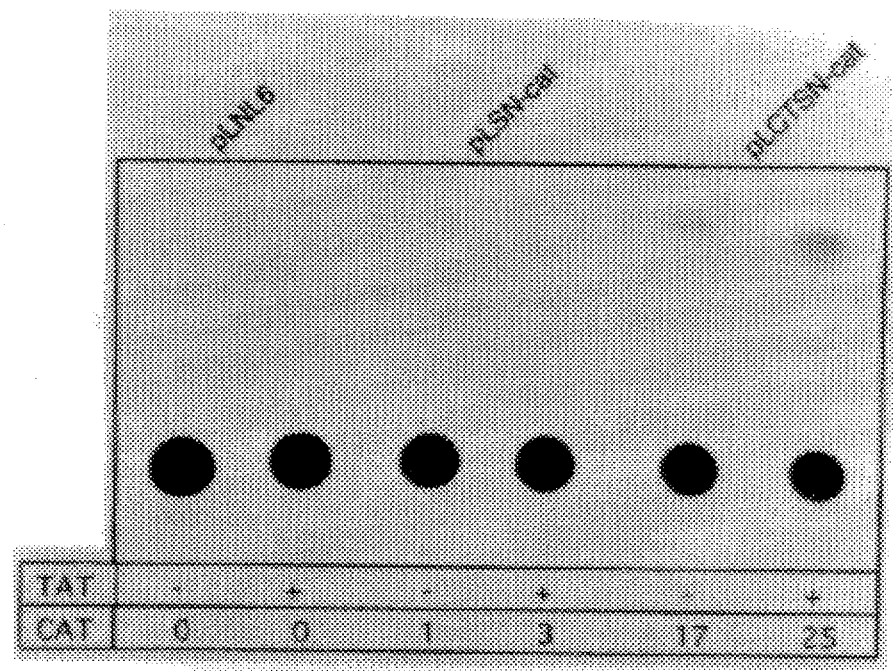
FIG. 18 shows an autoradiograph of a CAT assay depicting the long term expression of genes in the pLSN-cat and pLCTSN-cat constructs in transduced HepG2 cells in the presence or absence of Tat.

As shown in FIGS. 17 and 18, in both HeLa (FIG. 17) and HepG2 cells (FIG. 18), the pLCTSN-cat vector exhibited higher levels of CAT activity than did pLSN-cat, with a more pronounced difference seen in the HepG2 cells. The trans-activation effect of Tat was also assessed in the stably transduced HepG2 cells by transfecting the cells with a Tat plasmid (pCEP-tat). In this case a clear, but relatively modest level of trans-activation was observed (FIG. 18). Control transfections using a β-galactosidase reporter construct suggested that less than 10% of the transduced HepG2 cells would be transfected with the Tat plasmid. Therefore, trans-activation would be expected to be at least 10-fold higher if all HepG2 cells had been transfected with the Tat plasmid. Note that the pLNL6 vector does not contain the CAT gene.

Similar results were obtained using the pLGCTSN vector in long term expression studies. The pLGCTSN vector was transduced into HeLa cells as described above for the pLCTSN vector. The transduced cells were grown in the presence of medium containing G418 for two months. G418-resistant HeLa cells containing the pLGCTSN vector were fused with a stable HeLa cell line which constitutively express the Tat protein [HeLa-tat-III (available from the NIH AIDS Research and Reference Reagent Program, Bethseda, Md.; catalog number 502)] using polyethylene glycol 1500 (BM). This method of introducing the Tat protein is much more efficient than the transfection method employed above and results in the introduction of Tat into essentially all of the stably transduced HeLa cells. CAT assays were performed on extracts of cell lysates from the fused cells. The results of the CAT assay showed that the pLGCTSN vector stably expressed the inserted CAT gene and that expression from pLGCTSN was inducible by Tat (15 to 20-fold) in long term cultures.

These results demonstrate that the pLCTSN and pLGCTSN vectors are stable over a relatively long period (2 to 3 months) and continue to exhibit higher levels of promoter activity than the wild type M-MuLV construct.

EXAMPLE 9

Incorporation of HIV-1 Packaging Sequences into M-MuLV Vectors

Traditional gene therapy vectors can only infect a target cell once because the lack of M-MuLV structural proteins in the target cells precludes the packaging of vector RNA into vital particles. In some instances it would be advantageous to allow the spread of the vector genome into other cells. For example, when the vector carries genes designed to inactivate a pathogenic virus (e.g., HIV), allowing the spread of the anti-viral vector sequences would increase the therapeutic value of the vector.

To further modify the improved gene therapy vectors for anti-HIV purposes, sequences in the HIV genome that are essential to genome packaging were cloned into the pLSN and pLLLgpt vectors. Upon transduction, expression of HIV packaging proteins in the target cells (i.e., HIV-infected cells) will allow the assembly of the therapeutic M-MuLV vector into HIV particles thus the anti-HIV genes contained on the vector will gain access to the target HIV genome. This strategy would also help to overcome the physiological barrier of finding target RNA in a cell [Sullenger, B. A. and Cech, T. R. (1993) Science 262:1566]. This is particularly important when the anti-HIV genes contained on the therapeutic vector are ribozymes.

To permit the M-MuLV-based vectors to be packaged into HIV particles, packaging sequences derived from HIV-1 which span the psi site (near the gag AUG) were cloned into the pLLL and pLLLgpt vectors at the polylinker region. Two HIV-derived packaging sequences were generated. PAK100 contains approximately 100 nucleotides derived from HIV-1 and restriction recognition site for BamHI at the 3' end and a cohesive overhang at the 5' end for SalI. PAK100 contains the following sequence: 5'-TCGACGGATCCGCAGGATCGGCTTGCTGAAGC-GCGCACGGCAA GAGGCGAGGGCGGCGACTG-GCATGCACGCCAAAAATTTTGACTAGCGGAGG CTAGAAGGAGAGAAAGCTTGGATCC-3' (SEQ ID NO:10). PAK140 contains approximately 140 nucleotides derived from HIV-1 and contains the following sequence 5'-TCGACGGATCCGCAGGATCGGCTTGCTGAAGCG-CGCACGGCAAG AGGCGAGGGCGGCGACTGGCAT-GCACGCCAAAAATTTTGACTAGCGGAGGCT AGAAGGAGAGAAAGCTTGGATCCCTAGAC-CGGTGCGAGAGCGTCGGTATTAA GCGGGGGAGAATTACCTAGGTGTCGACTCGCGAT-CGAT-3' (SEQ ID NO:11).

Figure 19:
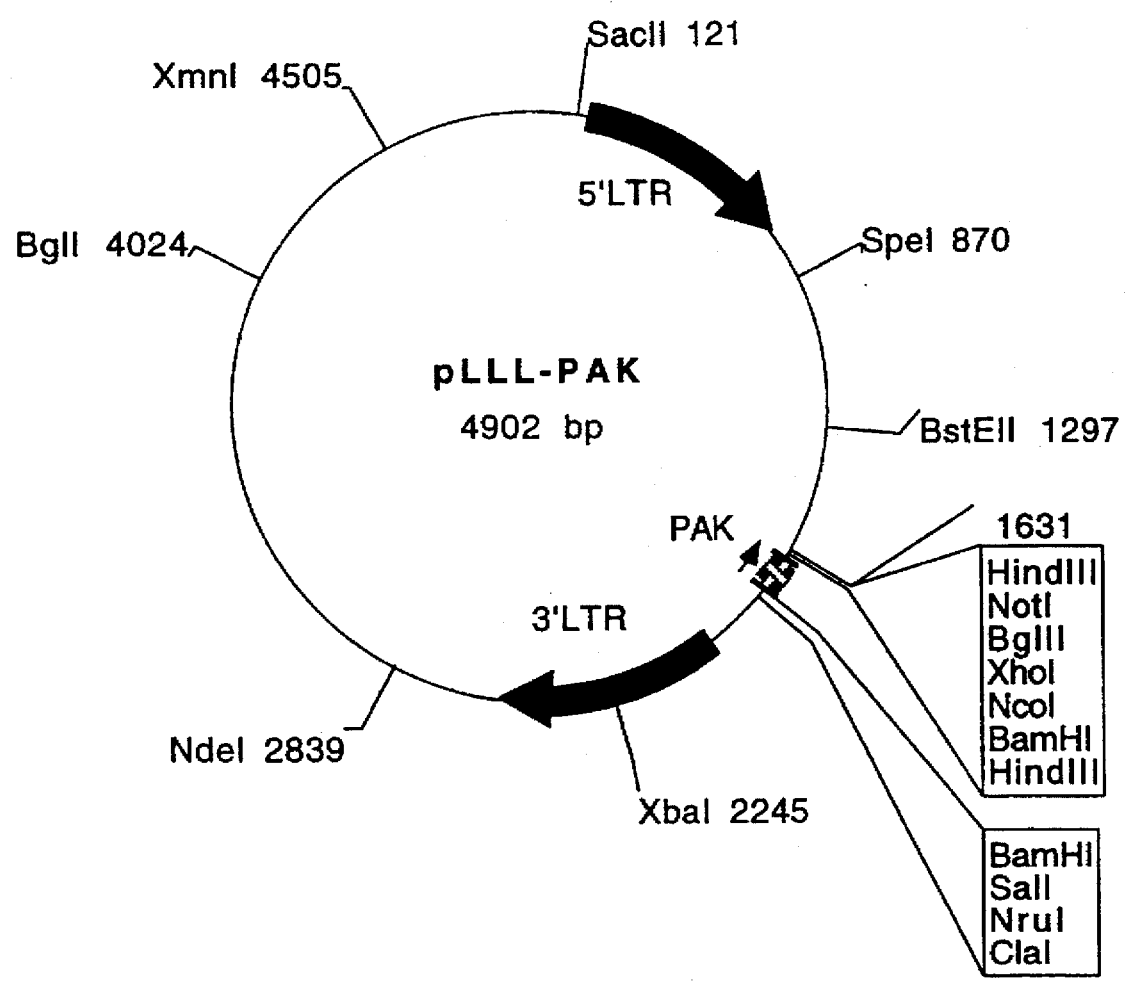
FIG. 19 shows the map of the retroviral vector pLLL-PAK100. Selected restriction enzyme sites are indicated.
Figure 20:
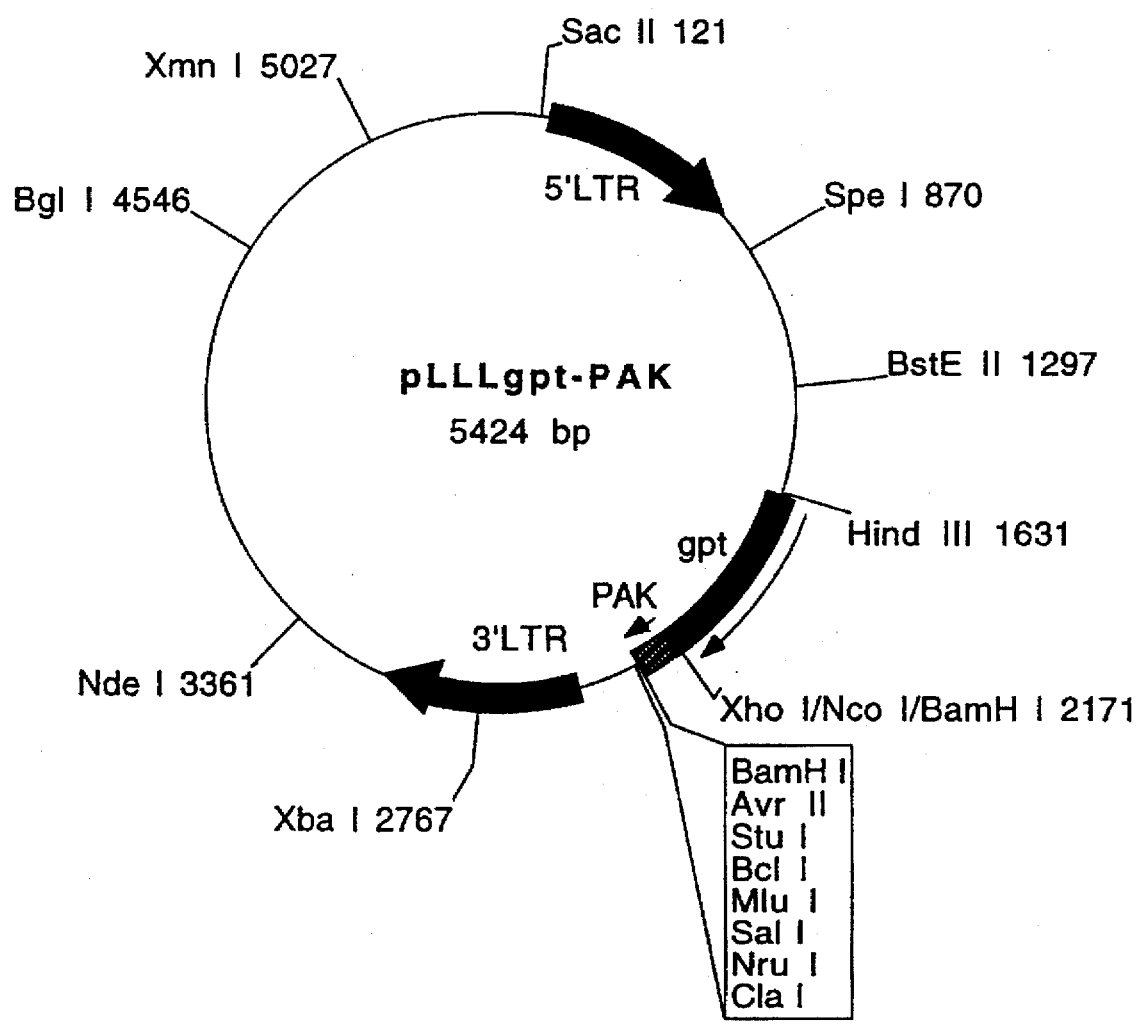
FIG. 20 shows the map of the retroviral vector pLLLgpt-PAK100. Selected restriction enzyme sites are indicated.

The PAK100 sequence was generated by annealing together the following four oligonucleotides: 5'-TCGACGGATCCGCAGGACTCGGCTTGCTGAAG-CGCGCAC GGCAAGAGGCGAGGGCGGCGACT-GGCATG-3' (SEQ ID NO:20); 5'-CCAGTCG CCGC-CCTCGCCTCTTGCCGTGCGCGCTTCAG-CAAGCCGAGTCCTGCGGAT CCG-3' (SEQ ID NO:21); 5'-CACGCCAAAAATTTTGACTAGCGGAGGCTAGAAG GAGAGAAAGCTTG-3' (SEQ ID NO:22); 5'-GATCCAAGCTTTCTCTCCTTCTAGC CTCCGCTAGTCAAAATTTTTGGCGTGCATG-3' (SEQ ID NO:23). Annealing was performed as described in Example 3. This generated a 119 bp DNA fragment containing the HIV packaging signal and created 5' SalI and 3' BamHI restriction sites for ease of cloning. The PAK100 sequence was cloned into pLLL digested with XhoI-BamHI digested pLLL to generate pLLL-PAK100. The PAK100 sequence was then removed from pLLL-PAK 100 by BamHI digestion and inserted into the BamHI site of pLLLgpt to generate pLLLgptPAK100. pLLL-PAK100 and pLLgpt-PAK100 are shown schematically in FIGS. 19 and 20, respectively.

Figure 21:
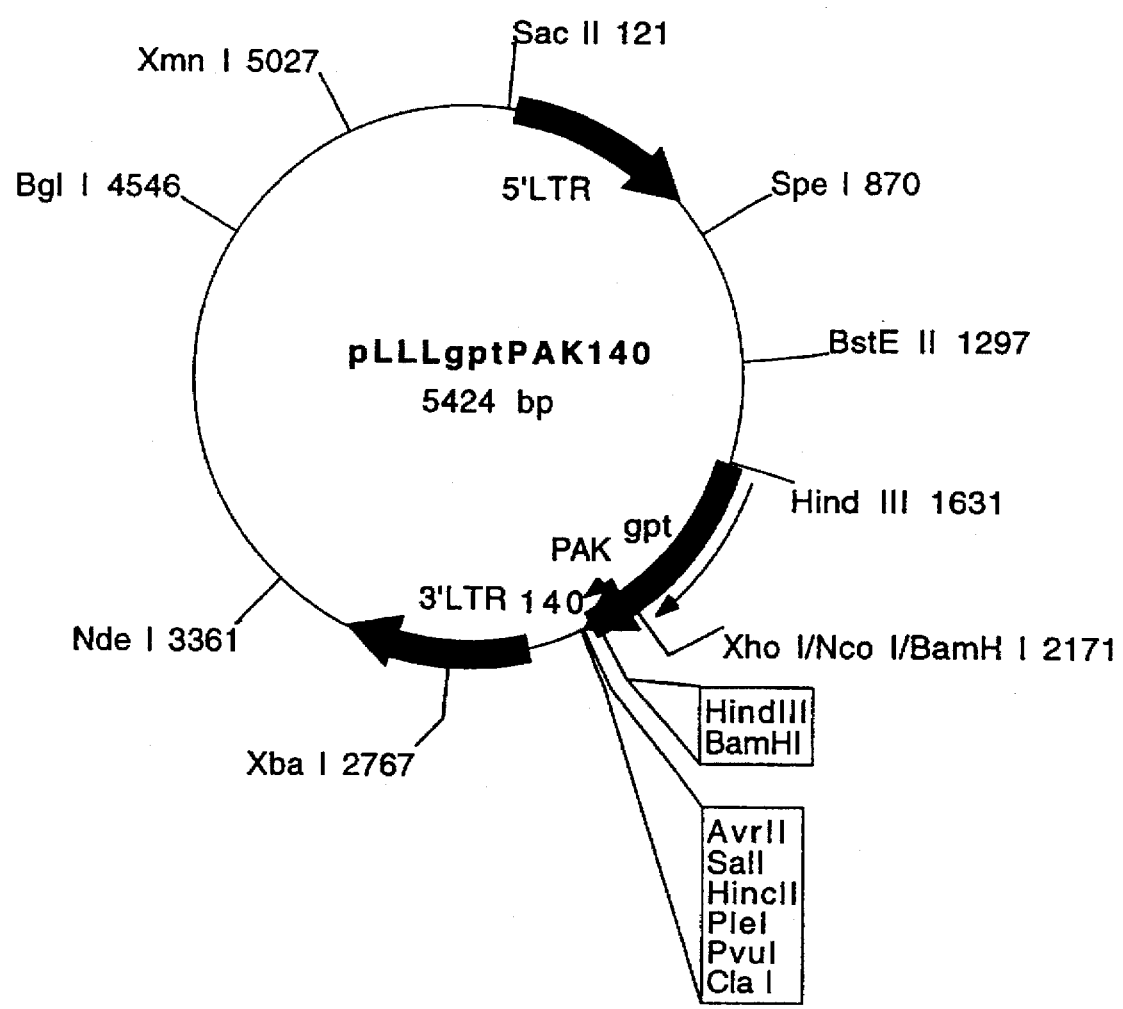
FIG. 21 shows the map of the retroviral vector pLLLgpt-PAK140. Selected restriction enzyme sites are indicated.

The PAK140 sequence (SEQ ID NO:11) was constructed by annealing together the following two oligonucleotides: 5' CTAGACCGGTGCGAGAGCGTCGGTATT AAGCGGGGGAGAATTACCTAGGTG 3' (SEQ ID NO:24) and 5' TCGACACC TAGGTAATTCTC-CCCCGCTTAATACCGACGCTCTCGCACCGG 3' (SEQ ID NO:25). Annealing was performed as described in Example 3. The resulting double stranded DNA fragment contains overhanging ends compatible with AvrII and SalI; this fragment was inserted into pLLLgpt-PAK100 digested with AvrII and SalI to generate pLLLgpt-PAK 140. pLLLgpt-PAK140 is shown schematically in FIG. 21.

The ability of the viral RNA containing the synthetic HIV psi sequences to be packaged into an HIV particle inside an HIV-infected cell was tested using the following co-transfection assay.

HeLa cells were transfected with the following three plasmids: pLLLgpt-PAK140, pHIVhyg (described below) and SV-ψ⁻-E-MLV [Landau, N. R. and Littman, D. R. (1992) J. Virol. 66:5110]. As a control, a duplicate culture of HeLa cells was transfected with pHIVhyg.

pLLLgpt-PAK140 contains the gpt gene which allows for selection of cells by growth in the presence of mycophenolic acid. pLLLgpt-PAK140 contains the wild type M-MuLV LTR and HIV packaging sequences (PAK 140).

pHIVhyg contains the hyg gene which allows for the selection of cells by growth in the presence of hygromycin. pHIVhyg contains the HIV LTR and HIV packaging sequences. pHIVhyg expresses the HIV gag and pol genes. The gag gene encodes the structural components of the viral particle; the pol gene encodes a protease, reverse transcriptase and integrase. The expression of the HIV gag and pol gene products in the transfected HeLa cell allows for the reverse transcription and integration of viral RNA containing the HIV LTR and the HIV packaging signal (i.e., pHIVhyg).

SV-ψ⁻-E-MLV is an ecotropic M-MuLV expression vector. SV-ψ⁻-E-MLV expresses the M-MuLV gag and pol gene products. The presence of the M-MuLV pol gene products in the transfected HeLa cell allows the reverse transcription and integration of the pLLLgpt-PAK140 genome.

Figure 22:
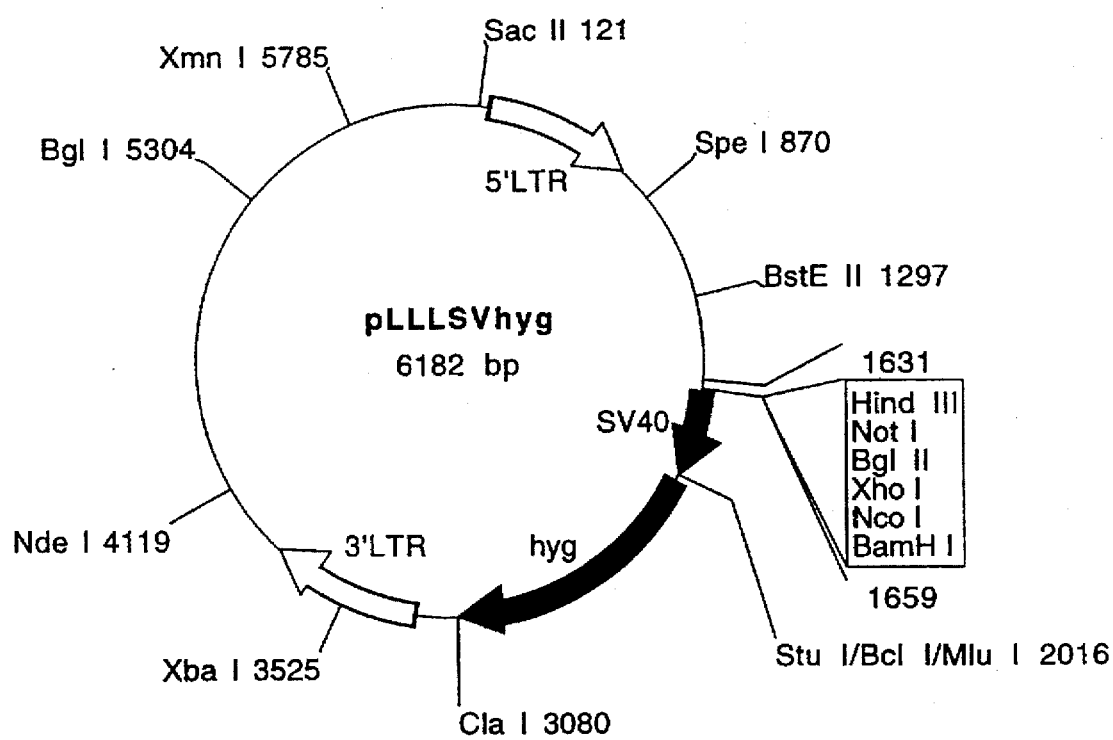
FIG. 22 shows the map of the retroviral vector pLLSVhyg Selected restriction enzyme sites are indicated.

Because the transfected HeLa cells express the gag and pol gene products from both HIV and M-MuLV, the ability of pLLLgpt-PAK140 viral RNA to be packaged inside HIV particles was examined. The rational for the assay used is as follows. If pLLLgpt-PAK140 RNA is packaged into HIV particles, then the mixed particle can infect CD4⁺ cells (i.e., the cell type infected by HIV). The packaging of pLLLgpt-PAK140 RNA into HIV particles would be expected to reduce the number of hyg-resistant colonies seen when HeLa CD4 are transduced with virus produced by HeLa cells co-transfected with pLLLgpt-PAK, pHIVhyg and SV-ψ⁻-E-MLV.

pHIVhyg was constructed as follows. The hygromycin B phosphotransferase (hyg) gene was amplified using the PCR. The PCR was performed as described in Example 2 with the exception that the following primer pair was used: 5'-GAGATATGAAAAAGCCTGAACTCAC-3' (SEQ ID NO:26) and 5'-CGCGACCGGCTGCAGAACAGCGGGC-3' (SEQ ID NO:27). The pCEP4 plasmid (Invitrogen) was used as a template for the isolation of the hyg sequences. The amplified hyg gene was inserted into pLLLSV40 digested with MluI and ClaI to generate pLLLSVhyg (shown schematically in FIG. 22).

The SV-hyg gene fragment (HindIII to SalI of pLLLSVhyg) was inserted between the AUG of the nef gene (a HindIII site was generated at the AUG-nucleotide 8787 of HIV$_{NL43}$ by site-specific mutagenesis) and the XhoI site (nucleotide 8887) of HIV$_{NL43}$ [Adachi, A. et al. (1986) J. Virol. 59:284] to generate pHIVhyg. HIV$_{NL43}$ is a plasmid containing a wild type HIV genome. The nef gene was used as the site of insertion for the selectable marker because the nef gene is not needed for the replication of the HIV in tissue culture cells. The nef gene contains a unique XhoI site located just downstream of the ATG for the nef gene product. In order to avoid having the nef ATG upstream of the ATG for the hyg gene, the ATG of the nef gene was eliminated using site-directed mutagenesis to replace the ATG with a HindIII site.

The three plasmids were grown and purified as described in Example 1. HeLa cell were transfected with an equimolar ratio of each of the plasmids using the calcium phosphate co-precipitation protocol described in Example 1.

To determine the efficiency of packaging, virus was harvested from the transfected HeLa cells and was used to infect HeLa CD4 cells [Chesebro, B. et al. (1990) J. Virol. 64:215; HeLa CD4 cells are available from the NIH AIDS Research and Reference Reagent Program, Bethseda, Md.; catalog numbers 1109 and 459]. The presence of the CD4 molecule on the surface of the cell allows for infection of the cell by virus particles containing HIV gag and env proteins. Infection was carried out as described in Example 7.

To determine whether the addition of the PAK sequences on the M-MuLV-based vector DNA interfered with the packaging of HIVhyg RNA into HIV particles, an aliquot of HeLa cells were co-transfected with pHIVhyg, pLLLgpt-PAK140 and SV-ψ⁻-E-MLV. A parallel culture of HeLa cells was co-transfected with pHIVhyg alone. Virus was harvested from the two HeLa cultures 48 hr after co-transfection. The harvested virus (1 ml of culture supernatant) was used to infect duplicate cultures of HeLa CD4 cells. Infection was carried out as described in Example 7.

The efficiency of packaging of the pHIVhyg RNA was determined by culturing the transduced HeLa CD4 cells in hygromycin-containing medium [DMEM, 10% FBS and 100 µg/ml hygromycin (Calbiochem, San Diego, Calif.)]. Hygromycin-resistant HeLa CD4 colonies were counted 10 to 12 days after infection. The results are summarized in Table 4.

TABLE 4

Presence of PAK Sequences Reduces Production Of Infections HIV Particles

| Vectors | Number of Hyg-Resistant HeLa CD4 colonies |
| --- | --- |
| pHIVhyg + pLLLgpt-PAK140 + SV-ψ-E-MLV | 14 |
| pHIVhyg | 39 |

The results shown in Table 4 show that the PAK sequences present in pLLLgpt-PAK140 interfere with the packaging of the pHIVhyg genomic RNA into HIV particles. This interference results in an almost 3-fold drop in the amount of infectious HIV particles produced by the transfected HeLa cells harboring both the HIV vector (pHIVhyg) and the PAK vector (pLLLgpt-PAK140). These results show that the inclusion of HIV packaging sequences (e.g., the PAK140 sequences) on the vector allows the vector to not only deliver genes to an HIV infected cell but also allows the vector to interfere with the packaging of the HIV genome into viral particles. Thus, the inclusion of the PAK sequences on a retroviral vector increases the therapeutic value of the vector when the vector is to be used to deliver anti-HIV genes to HIV infected cells.

Figure 23:
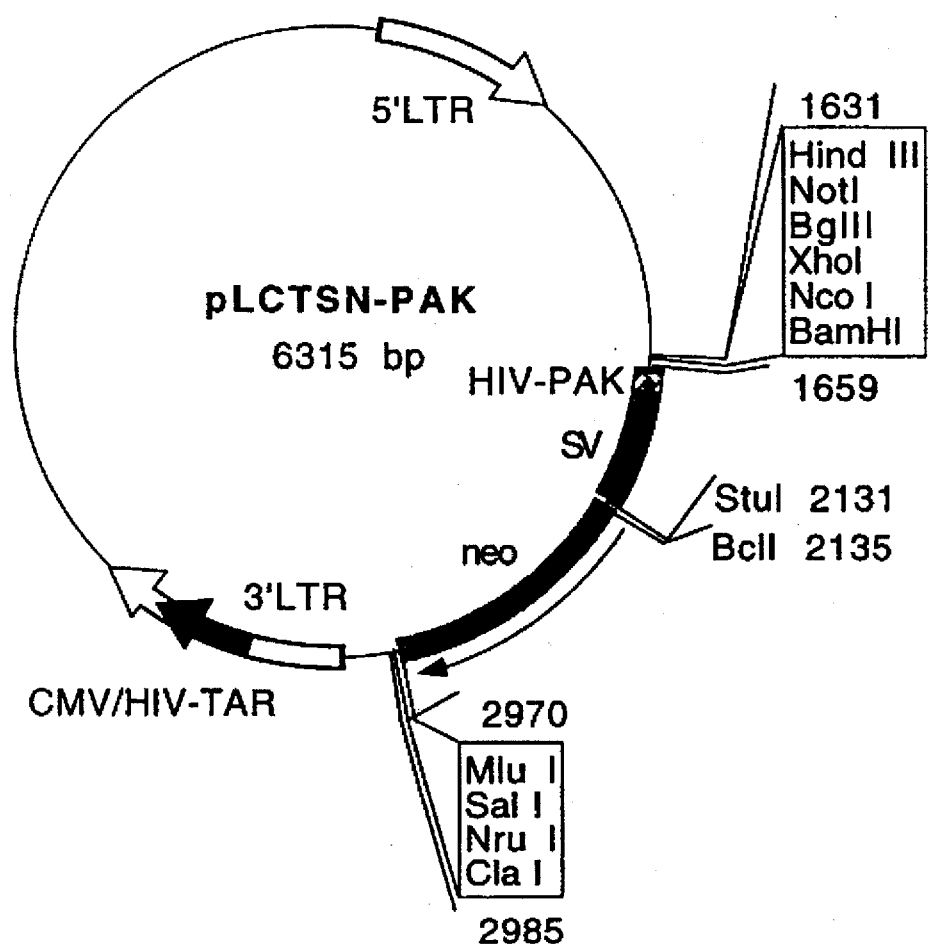
FIG. 23 shows the map of the retroviral vector pLCTSN-PAK. Selected restriction enzyme sites are indicated.

In order to determine whether any of the HIV particles contain the pLLLgpt-PAK140 RNA, HeLa cells are co-transfected with equimolar amounts of pLLLgpt-PAK140, pHIVhyg and SV-ψ⁻-E-MLV. Virus is harvested and used to transduce triplicate cultures of HeLa CD4 cells. The transduced HeLa cells are grown in either XMHAT medium [DMEM, 10% FBS, 1X HAT Supplement, 250 µg/ml xanthine and 25 µg/ml mycophenolic acid; all reagents were obtained from BRL); hygromycin-containing medium (described above) or medium containing both mycophenolic acid and hygromycin. The ratio of gpt⁺ to hyg⁺ to gpt⁺ and hyg⁺ colonies is determined. If the PAK sequences present upon pLLLgpt-PAK140 allow the vector RNA to be packaged into HIV particles and reverse transcribed then one would expect to see the same number of gpt⁺ colonies (i.e., capable of growth in mycophenolic acid) and gpt⁺ plus hyg⁺ colonies (i.e., colonies capable of growth in both mycophenolic acid and hygromycin).

pLLLgpt-PAK140 was constructed to test the efficiency of packaging of M-MuLV-based vectors containing a HIV-derived packaging signal into HIV particles. For the purpose of constructing an anti-HIV gene therapy vector, the HIV psi site (either PAK100 or PAK140) is inserted into pLCTSN, which contains the improved LTR, to create pLCTSN-PAK (shown schematically in FIG. 23). pLCTSN-PAK is constructed by insertion of the annealed HIV psi sequences (described above) into pLCTSN (Example 6c) digested with BamHI. This design will enhance the therapeutic efficacy of the improved vectors carrying anti-HIV genes (such as anti-HIV ribozymes).

EXAMPLE 10

Selection of High Titer Packaging Cell Clones

In order to increase the titer of recombinant virus produced by the packaging cell lines, the established PA317 and GP-AM12 [Markowitz, D. et al. (1988) Virol. 167:400] cell lines were subcloned to isolate those subclones which produced the highest levels of reverse transcriptase within the starting population of packaging cells. The level of reverse transcriptase produced by the cell is an indication of the efficiency of production of the structural genes by the cell line which are needed to package the transfected recombinant vectors.

PA317 and GP-AM12 cells were plated at low density in T75 flasks (Falcon). Following three to four weeks of culturing, individual cell colonies were picked up using a cotton swab dipped in trypsin (Gibco-BRL). Ten subclones were picked from the PA317 cell line and 6 subclones were picked from the GP-AM12 cell line. The single cell clones were then grown in T25 flasks (Falcon) to confluency. An identical number of cells from each clone were cultured in a T25 flask and the supernatant was harvested at 24 hr and 48 hr. Reverse transcriptase levels were measured as follows.

Figure 24:
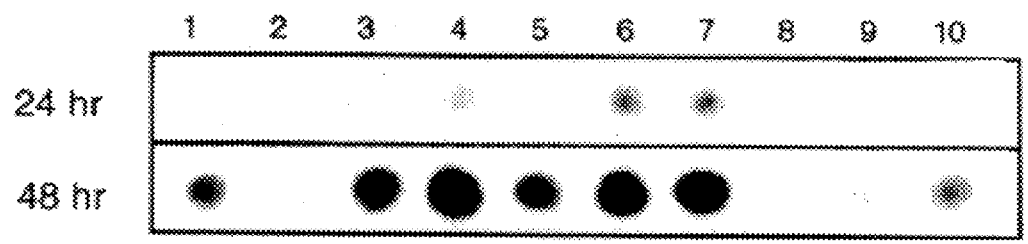
FIG. 24 shows the reverse transcriptase dot blot results of PA317 and GP-AM12 culture supernatants.
Figure 24:
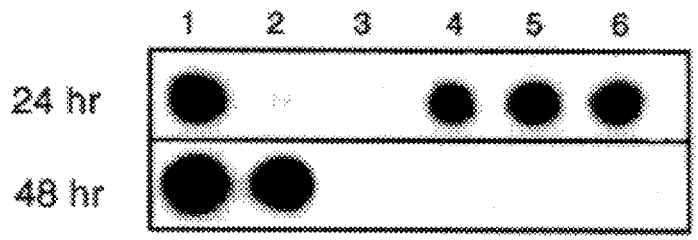

A 10 μl sample of culture medium (supernatant) was incubated with 50 μl of a reaction cocktail containing 50 mM Tris-HCl, pH 8.3, 20 mM DTT, 0.6 mM MnCl$_2$, 60 mM NaCl, 0.05% NP40, 5 μg/ml of oligodeoxythymidilic acid, 10 μg/ml of polyriboadenylic acid and 10 μM of [α-$^{32}$P] dTTP (DuPont NEN, specific activity 800 Ci/mmol). The reaction was incubated at 37° C. for 1 hr. A 3 μl aliquot was then spotted onto DE-81 paper (Whatman), and air dried. The DE-81 paper was washed 3 times in 2X SSC (20X SSC comprises: 3M NaCl, 0.3M sodium citrate, pH 7.0) and autoradiographed. These results are shown in FIG. 24. The clones expressing the highest levels of RT clones were chosen for use in retroviral packaging studies.

From the above examples it should be clear that the improved retroviral vectors of the invention, comprising novel LTRs and extended MuMLV packaging sequences, provide for the efficient packaging of vector RNA and the efficient long-term expression of genes inserted into the improved vectors. The improved promoters found in the novel LTRs obviate the need to use an internal promoter to drive the expression of inserted genes. The inserted genes are expressed at high levels which enables the study of gene expression, cell lineage analysis in a wide variety of cell lines. The improved promoters function in a wide variety of human cell types making vectors containing these promoters ideal for the delivery of genes to a variety of cell lines and tissues. The vectors containing the novel LTRs and HIV-1 packaging sequences provide an improved means of delivering anti-HIV genes.

I claim:

1. A recombinant Moloney murine leukemia virus long terminal repeat (MoMLV LTR) having the sequence set forth in SEQ ID NO.: 17, wherein the U3 region of said LTR is replaced with the human cytomegalovirus immediate-early enhancer/promoter (CMV-IE) and the human immunodeficiency virus TATA (HIV-TATA) and transactivation response (HIV-TAR) elements.

2. A retroviral expression vector containing the recombinant MoMLV LTR of claim 1.

3. The recombinant MoMLV LTR-containing expression vector of claim 2, wherein said LTR is activated by the human immunodeficiency virus type 1 (HIV-1) Tat protein.

4. A transformed or transfected bacterial host containing the recombinant MoMLV LTR-containing expression vector of claim 2.

5. A transduced or transfected human cell line containing the recombinant MoMLV LTR-containing expression vector of claim 2.

6. A recombinant murine amphotropic retroviral expression vector containing the recombinant MoMLV LTR-containing expression vector of claim 1.

7. The recombinant MoMLV LTR-containing vector of claim 6, wherein said expression vector comprises the following additional elements:
   a) a first packaging signal joined to said recombinant LTR; and,
   b) a second LTR joined to said first packaging signal.

8. The recombinant MoMLV LTR-containing expression vector of claim 7, wherein said vector further comprises a nucleotide sequence encoding a selectable marker.

9. The recombinant MoMLV LTR-containing expression vector of claim 8, wherein said selectable marker is encoded by the neomycin phosphoribosyltransferase (neo) gene.

10. The recombinant MoMLV LTR-containing expression vector of claim 9, wherein said vector has the designation pLCTSN.

11. The recombinant MoMLV LTR-containing expression vector of claim 7, wherein said first packaging signal comprises the MoMLV extended packaging signal, thereby increasing the packaging efficiency of RNAs transcribed from said vector.

12. The recombinant MoMLV LTR-containing expression vector of claim 11, wherein said expression vector has the designation pLGCTSN.

13. The recombinant MoMLV LTR-containing expression vector of claim 7, wherein said vector further comprises a second packaging signal operably linked between said first and second LTRs, said second packaging signal being derived from HIV-1.

14. The recombinant MoMLV LTR-containing expression vector of claim 13, wherein said second packaging signal has the nucleotide sequence set forth in SEQ ID NO.: 10.

15. The recombinant MoMLV LTR-containing expression vector of claim 13, wherein said second packaging signal has the nucleotide sequence set forth in SEQ ID NO.: 11.

16. A recombinant murine amphotropic retroviral expression vector comprising the following operatively linked elements:
   a) a first LTR;
   b) a packaging signal;
   c) a restriction enzyme recognition site; and,
   d) a second LTR having the sequence set forth in SEQ ID NO.: 17.

17. The recombinant murine amphotropic retroviral expression vector of claim 16, wherein said vector contains a polylinker containing two or more restriction enzyme recognition sites.

18. The recombinant murine amphotropic retroviral expression vector of claim 16, wherein said vector contains a selectable marker inserted into said polylinker.

19. The recombinant murine amphotropic retroviral expression vector of claim 18, wherein said selectable marker is encoded by the neomycin phosphoribosyltransferase (neo) gene.

20. The recombinant murine amphotropic retroviral expression vector of claim 16, wherein said packaging signal consists of the extended MoMLV packaging signal.

21. The recombinant murine amphotropic retroviral expression vector of claim 16, wherein said vector further comprises a second packaging signal operably linked between said first and second LTRs, said second packaging signal being derived from HIV-1.

22. The recombinant murine amphotropic retroviral expression vector of claim 21, wherein said second packaging signal has the nucleotide sequence set forth in SEQ ID NO.: 10.

23. The recombinant murine amphotropic retroviral expression vector of claim 21, wherein said second packaging signal has the nucleotide sequence set forth in SEQ ID NO.: 11.

24. An in vitro method for the expression of a heterologous gene product in a human cell line comprising the following steps:
   a) providing a human cell line;
   b) providing a retroviral expression vector containing a recombinant Moloney murine leukemia virus long terminal repeat (MoMLV LTR) having the sequence set forth in SEQ ID NO.: 17 operatively linked to a heterologous gene;
   c) introducing said recombinant MoMLV LTR-containing expression vector into said human cell line under conditions facilitating the expression of the gene product enocoded by said heterologous gene.

25. The in vitro method of claim 24, wherein said expression vector further contains a gene encoding a selectable marker.

26. The in vitro method of claim 25, wherein said selectable marker is encoded by the neomycin phosphoribosyltransferase (neo) gene.

27. The in vitro method of claim 25, wherein said conditions include growing the cells in a selective medium that only supports the growth of cells containing the selectable marker.

28. The in vitro method of claim 27, wherein said selective medium contains the antibiotic G418.

* * * * *

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 6145 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
GAATTCATAC  CAGATCACCG  AAAACTGTCC  TCCAAATGTG  TCCCCCTCAC  ACTCCCAAAT      60

TCGCGGGCTT  CTGCCTCTTA  GACCACTCTA  CCCTATTCCC  CACACTCACC  GGAGCCAAAG     120

CCGCGGCCCT  TCCGTTTCTT  TGCTTTTGAA  AGACCCACC   CGTAGGTGGC  AAGCTAGCTT    180

AAGTAACGCC  ACTTTGCAAG  GCATGGAAAA  ATACATAACT  GAGAATAGAA  AAGTTCAGAT    240

CAAGGTCAGG  AACAAAGAAA  CAGCTGAATA  CCAAACAGGA  TATCTGTGGT  AAGCGGTTCC    300

TGCCCCGGCT  CAGGGCCAAG  AACAGATGAG  ACAGCTGAGT  GATGGGCCAA  ACAGGATATC    360

TGTGGTAAGC  AGTTCCTGCC  CCGGCTCGGG  GCCAAGAACA  GATGGTCCCC  AGATGCGGTC    420

CAGCCCTCAG  CAGTTTCTAG  TGAATCATCA  GATGTTTCCA  GGGTGCCCCA  AGGACCTGAA    480

AATGACCCTG  TACCTTATTT  GAACTAACCA  ATCAGTTCGC  TTCTCGCTTC  TGTTCGCGCG    540

CTTCCGCTCT  CCGAGCTCAA  TAAAAGAGCC  CACAACCCCT  CACTCGGCGC  GCCAGTCTTC    600

CGATAGACTG  CGTCGCCCGG  GTACCCGTAT  TCCCAATAAA  GCCTCTTGCT  GTTTGCATCC    660
```

```
GAATCGTGGT CTCGCTGTTC CTTGGGAGGG TCTCCTCTGA GTGATTGACT ACCCACGACG    720
GGGGTCTTTC ATTTGGGGGC TCGTCCGGGA TTTGGAGACC CCTGCCCAGG GACCACCGAC    780
CCACCACCGG GAGGTAAGCT GGCCAGCAAC TTATCTGTGT CTGTCCGATT GTCTAGTGTC    840
TATGTTTGAT GTTATGCGCC TGCGTCTGTA CTAGTTAGCT AACTAGCTCT GTATCTGGCG    900
GACCCGTGGT GGAACTGACG AGTTCTGAAC ACCCGGCCGC AACCCTGGGA GACGTCCAG    960
GGACTTTGGG GGCCGTTTTT GTGGCCCGAC CTGAGGAAGG GAGTCGATGT GGAATCCGAC   1020
CCCGTCAGGA TATGTGGTTC TGGTAGGAGA CGAGAACCTA AAACAGTTCC CGCCTCCGTC   1080
TGAATTTTTG CTTTCGGTTT GGAACCGAAG CCGCGCGTCT TGTCTGCTGC AGCGCTGCAG   1140
CATCGTTCTG TGTTGTCTCT GTCTGACTGT GTTTCTGTAT TTGTCTGAAA ATTAGGGCCA   1200
GACTGTTACC ACTCCCTTAA GTTGACCTT AGGTCACTGG AAAGATGTCG AGCGGATCGC    1260
TCACAACCAG TCGGTAGATG TCAAGAAGAG ACGTTGGGTT ACCTTCTGCT CTGCAGAATG   1320
GCCAACCTTT AACGTCGGAT GGCCGCGAGA CGGCACCTTT AACCGAGACC TCATCACCCA   1380
GGTTAAGATC AAGGTCTTTT CACCTGGCCC GCATGGACAC CCAGACCAGG TCCCCTACAT   1440
CGTGACCTGG GAAGCCTTGG CTTTTGACCC CCCTCCCTGG GTCAAGCCCT TTGTACACCC   1500
TAAGCCTCCG CCTCCTCTTC CTCCATCCGC CCCGTCTCTC CCCCTTGAAC CTCCTCGTTC   1560
GACCCCGCCT CGATCCTCCC TTTATCCAGC CCTCACTCCT TCTCTAGGCG CCGGAATTCC   1620
GATCTGATCA AGAGACAGGA TGAGGATCGT TTCGCATGAT TGAACAAGAT GGATTGCACG   1680
CAGGTTCTCC GGCCGCTTGG GTGGAGAGGC TATTCGGCTA TGACTGGGCA CAACAGACAA   1740
TCGGCTGCTC TGATGCCGCC GTGTTCCGGC TGTCAGCGCA GGGGCGCCCG GTTCTTTTTG   1800
TCAAGACCGA CCTGTCCGGT GCCCTGAATG AACTGCAGGA CGAGGCAGCG CGGCTATCGT   1860
GGCTGGCCAC GACGGGCGTT CCTTGCGCAG CTGTGCTCGA CGTTGTCACT GAAGCGGGAA   1920
GGGACTGGCT GCTATTGGGC GAAGTGCCGG GGCAGGATCT CCTGTCATCT CACCTTGCTC   1980
CTGCCGAGAA AGTATCCATC ATGGCTGATG CAATGCGGCG GCTGCATACG CTTGATCCGG   2040
CTACCTGCCC ATTCGACCAC CAAGCGAAAC ATCGCATCGA GCGAGCACGT ACTCGGATGG   2100
AAGCCGGTCT TGTCGATCAG GATGATCTGG ACGAAGAGCA TCAGGGGCTC GCGCCAGCCG   2160
AACTGTTCGC CAGGCTCAAG GCGCGCATGC CCGACGGCGA GGATCTCGTC GTGACCCATG   2220
GCGATGCCTG CTTGCCGAAT ATCATGGTGG AAAATGGCCG CTTTTCTGGA TTCATCGACT   2280
GTGGCCGGCT GGGTGTGGCG GACCGCTATC AGGACATAGC GTTGGCTACC CGTGATATTG   2340
CTGAAGAGCT TGGCGGCGAA TGGGCTGACC GCTTCCTCGT GCTTTACGGT ATCGCCGCTC   2400
CCGATTCGCA GCGCATCGCC TTCTATCGCC TTCTTGACGA GTTCTTCTGA GCGGGACTCT   2460
GGGGTTCGAA ATGACCGACC AAGCGACGCC CAACCTGCCA TCACGAGATT TCGATTCCAC   2520
CGCCGCCTTC TATGAAAGGT TGGGCTTCGG AATCGTTTTC CGGGACGCCG GCTGGATGAT   2580
CCTCCAGCGC GGGGATCTCA TGCTGGAGTT CTTCGCCCAC CCCGGGCTCG ATCCCCTCGC   2640
GAGTTGGTTC AGCTGCTGCC TGAGGCTGGA CGACCTCGCG GAGTTCTACC GGCAGTGCAA   2700
ATCCGTCGGC ATCCAGGAAA CCAGCAGCGG CTATCCGCGC ATCCATGCCC CGAACTGCA   2760
GGAGTGGGGA GGCACGATGG CCGCTTTGGT CGACCCGGAC GGGACGCTCC TGCGCCTGAT   2820
ACAGAACGAA TTGCTTGCAG GCATCTCATG AGTGTGTCTT CCCGTTTTCC GCCTGAGGTC   2880
ACTGCGTGGA TGGAGCGCTG GCGCCTGCTG CGCGACGGCG AGCTGCTCAC CACCCACTCG   2940
AGGGCGTGCA GCGCTGCAGA GGCCGAGTGC AGAACTGCTC CAAAGGGACC TCAAGGCTTT   3000
CCGAGGGACA CTAGGCTGAC TCCATCGAGC CAGTGTAGAG ATAAGCTTAT CGATTAGTCC   3060
```

```
AATTTGTTAA AGACAGGATA TCAGTGGTCC AGGCTCTAGT TTTGACTCAA CAATATCACC    3120
AGCTGAAGCC TATAGAGTAC GAGCCATAGA TAAAATAAAA GATTTTATTT AGTCTCCAGA    3180
AAAAGGGGGG AATGAAAGAC CCCACCTGTA GGTTTGGCAA GCTAGCTTAA GTAACGCCAT    3240
TTTGCAAGGC ATGGAAAAAT ACATAACTGA GAATAGAGAA GTTCAGATCA AGGTCAGGAA    3300
CAGATGGAAC AGCTGAATAT GGGCCAAACA GGATATCTGT GGTAAGCAGT TCCTGCCCCG    3360
GCTCAGGGCC AAGAACAGAT GGAACAGCTG AATATGGGCC AAACAGGATA TCTGTGGTAA    3420
GCAGTTCCTG CCCCGGCTCA GGGCCAAGAA CAGATGGTCC CCAGATGCGG TCCAGCCCTC    3480
AGCAGTTTCT AGAGAACCAT CAGATGTTTC CAGGGTGCCC CAAGGACCTG AAATGACCCT    3540
GTGCCTTATT TGAACTAACC AATCAGTTCG CTTCTCGCTT CTGTTCGCGC GCTTCTGCTC    3600
CCCGAGCTCA ATAAAGAGC CCACAACCCC TCACTCGGGG CGCCAGTCCT CCGATTGACT    3660
GAGTCGCCCG GGTACCCGTG TATCCAATAA ACCCTCTTGC AGTTGCATCC GACTTGTGGT    3720
CTCGCTGTTC CTTGGGAGGG TCTCCTCTGA GTGATTGACT ACCCGTCAGC GGGGGTCTTT    3780
CATTTGGGGG CTCGTCCGGG ATCGGAGAC CCCTGCCCAG GGACCACCGA CCCACCACCG    3840
GGAGGTAAGC TGGCTGCCTC GCGCGTTTCG GTGATGACGG TGAAAACCTC TGACACATGC    3900
AGCTCCCGGA GACGGTCACA GCTTGTCTGT AAGCGGATGC CGGGAGCAGA CAAGCCCGTC    3960
AGGGCGCGTC AGCGGGTGTT GGCGGGTGTC GGGGCGCAGC CATGACCCAG TCACGTAGCG    4020
ATAGCGGAGT GTATACTGGC TTAACTATGC GGCATCAGAG CAGATTGTAC TGAGAGTGCA    4080
CCATATGCGG TGTGAAATAC CGCACAGATG CGTAAGGAGA AAATACCGCA TCAGGCGCTC    4140
TTCCGCTTCC TCGCTCACTG ACTCGCTGCG CTCGGTCGTT CGGCTGCGGC GAGCGGTATC    4200
AGCTCACTCA AAGGCGGTAA TACGGTTATC CACAGAATCA GGGGATAACG CAGGAAAGAA    4260
CATGTGAGCA AAAGGCCAGC AAAAGGCCAG GAACCGTAAA AAGGCCGCGT TGCTGGCGTT    4320
TTTCCATAGG CTCCGCCCCC CTGACGAGCA TCACAAAAAT CGACGCTCAA GTCAGAGGTG    4380
GCGAAACCCG ACAGGACTAT AAAGATACCA GGCGTTTCCC CCTGGAAGCT CCCTCGTGCG    4440
CTCTCCTGTT CCGACCCTGC CGCTTACCGG ATACCTGTCC GCCTTTCTCC CTTCGGGAAG    4500
CGTGGCGCTT TCTCATAGCT CACGCTGTAG GTATCTCAGT TCGGTGTAGG TCGTTCGCTC    4560
CAAGCTGGGC TGTGTGCACG AACCCCCCGT TCAGCCCGAC CGCTGCGCCT TATCCGGTAA    4620
CTATCGTCTT GAGTCCAACC CGGTAAGACA CGACTTATCG CCACTGGCAG CAGCCACTGG    4680
TAACAGGATT AGCAGAGCGA GGTATGTAGG CGGTGCTACA GAGTTCTTGA AGTGGTGGCC    4740
TAACTACGGC TACACTAGAA GGACAGTATT TGGTATCTGC GCTCTGCTGA AGCCAGTTAC    4800
CTTCGGAAAA AGAGTTGGTA GCTCTTGATC CGGCAAACAA ACCACCGCTG GTAGCGGTGG    4860
TTTTTTTGTT TGCAAGCAGC AGATTACGCG CAGAAAAAAA GGATCTCAAG AAGATCCTTT    4920
GATCTTTTCT ACGGGGTCTG ACGCTCAGTG GAACGAAAAC TCACGTTAAG GGATTTTGGT    4980
CATGAGATTA TCAAAAAGGA TCTTCACCTA GATCCTTTTA AATTAAAAAT GAAGTTTTAA    5040
ATCAATCTAA AGTATATATG AGTAAACTTG GTCTGACAGT TACCAATGCT TAATCAGTGA    5100
GGCACCTATC TCAGCGATCT GTCTATTTCG TTCATCCATA GTTGCCTGAC TCCCCGTCGT    5160
GTAGATAACT ACGATACGGG AGGGCTTACC ATCTGGCCCC AGTGCTGCAA TGATACCGCG    5220
AGACCCACGC TCACCGGCTC CAGATTTATC AGCAATAAAC CAGCCAGCCG GAAGGGCCGA    5280
GCGCAGAAGT GGTCCTGCAA CTTTATCCGC CTCCATCCAG TCTATTAATT GTTGCCGGGA    5340
AGCTAGAGTA AGTAGTTCGC CAGTTAATAG TTTGCGCAAC GTTGTTGCCA TTGCTGCAGG    5400
CATCGTGGTG TCACGCTCGT CGTTTGGTAT GGCTTCATTC AGCTCCGGTT CCCAACGATC    5460
```

```
AAGGCGAGTT  ACATGATCCC  CCATGTTGTG  CAAAAAAGCG  GTTAGCTCCT  TCGGTCCTCC      5520

GATCGTTGTC  AGAAGTAAGT  TGGCCGCAGT  GTTATCACTC  ATGGTTATGG  CAGCACTGCA      5580

TAATTCTCTT  ACTGTCATGC  CATCCGTAAG  ATGCTTTTCT  GTGACTGGTG  AGTACTCAAC      5640

CAAGTCATTC  TGAGAATAGT  GTATGCGGCG  ACCGAGTTGC  TCTTGCCCGG  CGTCAACACG      5700

GGATAATACC  GCGCCACATA  GCAGAACTTT  AAAAGTGCTC  ATCATTGGAA  AACGTTCTTC      5760

GGGGCGAAAA  CTCTCAAGGA  TCTTACCGCT  GTTGAGATCC  AGTTCGATGT  AACCCACTCG      5820

TGCACCCAAC  TGATCTTCAG  CATCTTTTAC  TTTCACCAGC  GTTTCTGGGT  GAGCAAAAAC      5880

AGGAAGGCAA  AATGCCGCAA  AAAAGGGAAT  AAGGGCGACA  CGGAAATGTT  GAATACTCAT      5940

ACTCTTCCTT  TTTCAATATT  ATTGAAGCAT  TTATCAGGGT  TATTGTCTCA  TGAGCGGATA      6000

CATATTTGAA  TGTATTTAGA  AAAATAAACA  AATAGGGGTT  CCGCGCACAT  TTCCCCGAAA      6060

AGTGCCACCT  GACGTCTAAG  AAACCATTAT  TATCATGACA  TTAACCTATA  AAAATAGGCG      6120

TATCACGAGG  CCCTTTCGTC  TTCAA                                               6145
```

( 2 ) INFORMATION FOR SEQ ID NO:2:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
GATCTAAGCT  TGCGGCCGCA  GATCTCGAGC  CATGGATCCT  AGGCCTGATC  ACGCGTCGAC      60

TCGCGAT                                                                    67
```

( 2 ) INFORMATION FOR SEQ ID NO:3:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
CGATCGCGAG  TCGACGCGTG  ATCAGGCCTA  GGATCCATGG  CTCGAGATCT  GCGGCCGCAA      60

GCTTA                                                                      65
```

( 2 ) INFORMATION FOR SEQ ID NO:4:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
AAGCTTGATC  ACCACCATGA  TTGAACAAGA  TGG                                     33
```

( 2 ) INFORMATION FOR SEQ ID NO:5:

( i ) SEQUENCE CHARACTERISTICS:
        ( A ) LENGTH: 34 base pairs
        ( B ) TYPE: nucleic acid ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

CCGGATCCGT CGACCCCAGA GTCCCGCTCA GAAG 34

( 2 ) INFORMATION FOR SEQ ID NO:6:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GCATCTAGAG TACTTCAAGA ACTGC 25

( 2 ) INFORMATION FOR SEQ ID NO:7:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GGGAATTCGA GGCTTAAGCA GTGGGTTCC 29

( 2 ) INFORMATION FOR SEQ ID NO:8:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

CCGGAGTAGC TAGCTGGAGT TCCGC 25

( 2 ) INFORMATION FOR SEQ ID NO:9:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GCTAGCGGTA CC 12

( 2 ) INFORMATION FOR SEQ ID NO:10:

( i ) SEQUENCE CHARACTERISTICS:
        ( A ) LENGTH: 119 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

TCGACGGATC CGCAGGATCG GCTTGCTGAA GCGCGCACGG CAAGAGGCGA GGGCGGCGAC    60

TGGCATGCAC GCCAAAAATT TTGACTAGCG GAGGCTAGAA GGAGAGAAAG CTTGGATCC    119

( 2 ) INFORMATION FOR SEQ ID NO:11:

( i ) SEQUENCE CHARACTERISTICS:
        ( A ) LENGTH: 185 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

TCGACGGATC CGCAGGATCG GCTTGCTGAA GCGCGCACGG CAAGAGGCGA GGGCGGCGAC    60

TGGCATGCAC GCCAAAAATT TTGACTAGCG GAGGCTAGAA GGAGAGAAAG CTTGGATCCT   120

AGACCGGTGC GAGAGCGTCG GTATTAAGCG GGGAGAATT ACCTAGGTGT CGACTCGCGA    180

TCGAT                                                                185

( 2 ) INFORMATION FOR SEQ ID NO:12:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

AAGGATCCTC GAGCCACCAT GGAGCCAGTA GATCCT     36

( 2 ) INFORMATION FOR SEQ ID NO:13:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

CAAGATCTGC ATGCTAATCG AACGGATCTG TC     32

( 2 ) INFORMATION FOR SEQ ID NO:14:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

ATCTAGAAGC TTAGTGCGCC AGATCTCTAT AATC     34

( 2 ) INFORMATION FOR SEQ ID NO:15:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

| ATCTAGACTC | GAGTTAGCGA | CCGGAGATTG | GC | | | 32 |

( 2 ) INFORMATION FOR SEQ ID NO:16:

( i ) SEQUENCE CHARACTERISTICS:
        ( A ) LENGTH: 702 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:16:

| AATGAAAGAC | CCCACCTGTA | GGTTTGGCAA | GCTAGCTTAA | GTAACGCCAT | TTTGCAAGGC | 60 |
| ATGGAAAAAT | ACATAACTGA | GAATAGAGAA | GTTCAGATCA | AGGTCAGGAA | CAGATGGAAC | 120 |
| AGCTGAATAT | GGGCCAAACA | GGATATCTGT | GGTAAGCAGT | TCCTGCCCCG | GCTCAGGGCC | 180 |
| AAGAACAGAT | GGAACAGCTG | AATATGGGCC | AAACAGGATA | TCTGTGGTAA | GCAGTTCCTG | 240 |
| CCCCGGCTCA | GGGCCAAGAA | CAGATGGTCC | CCAGATGCGG | TCCAGCCCTC | AGCAGTTTCT | 300 |
| AGAGTACTTC | AAGAACTGCT | GACATCGAGC | TTGCTACAAG | GACTTTCCG | CTGGGGACTT | 360 |
| TCCAGGGAGG | CGTGGCCTGG | GCGGGACTGG | GGAGTGGCGA | GCCCTCAGAT | GCTGCATATA | 420 |
| AGCAGCTGCT | TTTTGCCTGT | ACTGGGTCTC | TCTGGTTAGA | CCAGATCTGA | GCCTGGGAGC | 480 |
| TCTCTGGCTA | ACTAGGGAAC | CCACTGCTTA | AGCCTCGAAT | TCAGCTCAAT | AAAAGAGCCC | 540 |
| ACAACCCTC | ACTCGGGGCG | CCAGTCCTCC | GATTGACTGA | GTCGCCCGGG | TACCCGTGTA | 600 |
| TCCAATAAAC | CCTCTTGCAG | TTGCATCCGA | CTTGTGGTCT | CGCTGTTCCT | TGGGAGGGTC | 660 |
| TCCTCTGAGT | GATTGACTAC | CCGTCAGCGG | GGGTCTTTCA | TT | | 702 |

( 2 ) INFORMATION FOR SEQ ID NO:17:

( i ) SEQUENCE CHARACTERISTICS:
        ( A ) LENGTH: 825 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:17:

| AATGAAAGAC | CCCACCTGTA | GGTTTGGCAA | GCTAGCTTAA | GTAACGCCAT | TTTGCAAGGC | 60 |
| ATGGAAAAAT | ACATAACTGA | GAATAGAGAA | GTTCAGATCA | AGGTCAGGAA | CAGATGGAAC | 120 |
| AGCTGAATAT | GGGCCAAACA | GGATATCTGT | GGTAAGCAGT | TCCTGCCCCG | GCTCAGGGCC | 180 |
| AAGAACAGAT | GGAACAGCTG | AATATGGGCC | AAACAGGATA | TCTGTGGTAA | GCAGTTCCTG | 240 |
| CCCCGGCTCA | GGGCCAAGAA | CAGATGGTCC | CCAGATGCGG | TCCAGCCCTC | AGCAGTTTCT | 300 |
| AGCTGGAGTT | CCGCGTTACA | TAACTTACGG | TAAATGGCCC | GCCTGGCTGA | CCGCCCAACG | 360 |
| ACCCCCGCCC | ATTGACGTCA | ATAATGACGT | ATGTTCCCAT | AGTAACGCCA | ATAGGGACTT | 420 |
| TCCATTGACG | TCAATGGGAG | TTTGTTTTGG | CACCAAAATC | AACGGGACTT | TCCAAAATGT | 480 |
| CGTAATAACC | CCGCCCCGTT | GACGCAAATG | GGCGGTAGGC | GTGTACTCTA | GATGCTACAT | 540 |
| ATAAGCAGCT | GCTTTTTGCC | TGTACTGGGT | CTCTCTGGTT | AGACCAGATC | TGAGCCTGGG | 600 |
| AGCTCTCTGG | CTAACTAGGG | AACCCACTGC | TTAAGCCTCG | AATTCAGCTC | AATAAAAGAG | 660 |
| CCCACAACCC | CTCACTCGGG | GCGCCAGTCC | TCCGATTGAC | TGAGTCGCCC | GGGTACCCGT | 720 |

GTATCCAATA AACCCTCTTG CAGTTGCATC CGACTTGTGG TCTCGCTGTT CCTTGGGAGG    780

GTCTCCTCTG AGTGATTGAC TACCCGTCAG CGGGGGTCTT TCATT    825

( 2 ) INFORMATION FOR SEQ ID NO:18:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

GAACCTCCTC GTTCGACC    18

( 2 ) INFORMATION FOR SEQ ID NO:19:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

AACTAGAGCC TGGACCAC    18

( 2 ) INFORMATION FOR SEQ ID NO:20:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

TCGACGGATC CGCAGGACTC GGCTTGCTGA AGCGCGCACG GCAAGAGGCG AGGGCGGCGA    60

CTGGCATG    68

( 2 ) INFORMATION FOR SEQ ID NO:21:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

CCAGTCGCCG CCCTCGCCTC TTGCCGTGCG CGCTTCAGCA AGCCGAGTCC TGCGGATCCG    60

( 2 ) INFORMATION FOR SEQ ID NO:22:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

CACGCCAAAA ATTTTGACTA GCGGAGGCTA GAAGGAGAGA AAGCTTG 47

( 2 ) INFORMATION FOR SEQ ID NO:23:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

GATCCAAGCT TTCTCTCCTT CTAGCCTCCG CTAGTCAAAA TTTTGGCGT GCATG 55

( 2 ) INFORMATION FOR SEQ ID NO:24:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

CTAGACCGGT GCGAGAGCGT CGGTATTAAG CGGGGGAGAA TTACCTAGGT G 51

( 2 ) INFORMATION FOR SEQ ID NO:25:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

TCGACACCTA GGTAATTCTC CCCCGCTTAA TACCGACGCT CTCGCACCGG 50

( 2 ) INFORMATION FOR SEQ ID NO:26:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

GAGATATGAA AAAGCCTGAA CTCAC 25

( 2 ) INFORMATION FOR SEQ ID NO:27:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

CGCGACCGGC TGCAGAACAG CGGGC 25